US012559479B2

(12) United States Patent
Herrmann et al.

(10) Patent No.: US 12,559,479 B2
(45) Date of Patent: Feb. 24, 2026

(54) CELL PENETRATING CYANINE-COUPLED ANTIBODIES

(71) Applicant: City of Hope, Duarte, CA (US)

(72) Inventors: Andreas Herrmann, Del Mar, CA (US); Hua Yu, Glendora, CA (US); Christoph Lahtz, Duarte, CA (US)

(73) Assignee: CITY OF HOPE, Duarte, CA (US)

( * ) Notice: Subject to any disclaimer, the term of this patent is extended or adjusted under 35 U.S.C. 154(b) by 0 days.

(21) Appl. No.: 16/060,009

(22) PCT Filed: Dec. 9, 2016

(86) PCT No.: PCT/US2016/066025
§ 371 (c)(1),
(2) Date: Jun. 6, 2018

(87) PCT Pub. No.: WO2017/100714
PCT Pub. Date: Jun. 15, 2017

(65) Prior Publication Data

US 2019/0119259 A1 Apr. 25, 2019

Related U.S. Application Data

(60) Provisional application No. 62/265,727, filed on Dec. 10, 2015.

(51) Int. Cl.
*C07D 403/14* (2006.01)
*A61K 47/54* (2017.01)
(Continued)

(52) U.S. Cl.
CPC .......... *C07D 403/14* (2013.01); *A61K 47/545* (2017.08); *A61K 47/6891* (2017.08);
(Continued)

(58) Field of Classification Search
None
See application file for complete search history.

(56) References Cited

U.S. PATENT DOCUMENTS

| | | | | |
|---|---|---|---|---|
| 5,922,618 A | 7/1999 | Shigetou et al. | | |
| 2002/0172987 A1* | 11/2002 | Terstappen | B82Y 25/00 435/7.23 | |

(Continued)

FOREIGN PATENT DOCUMENTS

| | | | |
|---|---|---|---|
| JP | 2002-535655 A | 10/2002 | |
| JP | 2014-101370 A | 6/2014 | |

(Continued)

OTHER PUBLICATIONS

Ballou et al (Cancer Immunol Immunother (1995) 41:257-263) (Year: 1995).*

(Continued)

*Primary Examiner* — Karl J Puttlitz
(74) *Attorney, Agent, or Firm* — Mintz Levin Cohn Ferris Glovsky and Popeo PC

(57) ABSTRACT

Described herein are compositions relating to cell-penetrating conjugates of formula (I) or (IV). The compositions are capable of penetrating cells and recognizing intracellular targets (e.g., STAT3) and are, inter alia, useful for diagnostic and therapeutic purposes.

8 Claims, 4 Drawing Sheets

Cyanine 3 (Cy3)

Cyanine 5 (Cy5)

(51) Int. Cl.

| | |
|---|---|
| ***A61K 47/68*** | (2017.01) |
| ***C09B 23/01*** | (2006.01) |
| ***C09B 23/06*** | (2006.01) |
| ***C09B 23/08*** | (2006.01) |

(52) U.S. Cl.
CPC .......... *C09B 23/0066* (2013.01); *C09B 23/06* (2013.01); *C09B 23/083* (2013.01)

(56) References Cited

U.S. PATENT DOCUMENTS

| | | | | |
|---|---|---|---|---|
| 2006/0141531 | A1 | 6/2006 | Ebright et al. | |
| 2009/0092600 | A1* | 4/2009 | Kufe .................. | G01N 33/5008 514/1.1 |
| 2010/0143960 | A1* | 6/2010 | Bazin ................... | G01N 33/582 548/414 |
| 2011/0027190 | A1* | 2/2011 | Hasmann ................ | A61P 35/00 424/9.6 |
| 2012/0115133 | A1* | 5/2012 | Carter ...................... | C12Q 1/37 435/6.11 |
| 2013/0052731 | A1 | 2/2013 | Ma et al. | |
| 2013/0177979 | A1 | 7/2013 | Turkson | |
| 2014/0072516 | A1 | 3/2014 | Parker et al. | |
| 2015/0361090 | A1* | 12/2015 | Sun ...................... | G01N 33/582 436/547 |
| 2016/0115248 | A1* | 4/2016 | Singh ................. | C07K 16/3015 530/387.2 |

FOREIGN PATENT DOCUMENTS

| | | | |
|---|---|---|---|
| JP | 2015-526506 | A | 9/2015 |
| WO | WO-00/43780 | A1 | 7/2000 |
| WO | WO-02/26891 | A1 | 4/2002 |
| WO | WO-2009/118142 | A1 | 10/2009 |
| WO | WO-2012/050896 | A2 | 4/2012 |
| WO | WO-2012/050896 | A3 | 4/2012 |
| WO | WO-2014/035060 | A1 | 3/2014 |
| WO | 2014070686 | * | 5/2014 |
| WO | WO-2014/070686 | A1 | 5/2014 |
| WO | WO-2015/031837 | A1 | 3/2015 |

OTHER PUBLICATIONS

Database Caplus Chemical Abstracts Service, Columbus, Ohio, US; Database Accession No. 2014:756851, WO 2014070686, SRI International, USA, Swanson et al., May 8, 2014 (Year: 2014).*

Kalaitzidis et al., PLoS ONE on Nov. 21, 2008 (Year: 2008).*

Database Caplus Chemical Abstracts Service, Columbus, Ohio, US; Database Accession No. 2002:889451, Abstract of US 20020172987, Terstappen et al., (Nov. 21, 2002) (Year: 2002).*

Database Registry, Chemical Abstracts Service, Columbus, Ohio, US; Registry No. 146368-14-1, Cyanine 5, 1993 (Year: 1993).*

Walker et al., Molecular and Cellular Endocrinology 382 (2014) 616-621 (Year: 2014).*

Herceptin® Trastuzumab (1998), downloaded Jul. 27, 2022 from https://www.accessdata.fda.gov/drugsatfda_docs/label/1998/trasgen092598lb.pdf (Year: 1998).*

Database Caplus, Chemical Abstracts Service, Columbus, Ohio, US; Database Accession No. 2008:1477098, Abstract of US 20110027190, Hasmann et al., (Feb. 3, 2011) (Year: 2011).*

Database Registry, Chemical Abstracts Service, Columbus, Ohio, US; Registry No. 146368-14-1, Cy 5 NHS Ester, 1993 (Year: 1993).*

Ballou, B. et al. (Oct. 1995). "Tumor Labeling in Vivo Using Cyanine-Conjugated Monoclonal Antibodies," *Cancer Immunol Immunother* 41(4):257-263.

Extended European Search Report mailed on Jul. 8, 2019, for EP Patent Application No. 16874014.0, 9 pages.

International Search Report mailed on Mar. 27, 2017, for PCT Application No. PCT/US2016/066025, filed Dec. 9, 2016, 2 pages.

Written Opinion mailed on Mar. 27, 2017, for PCT Application No. PCT/US2016/066025, filed Dec. 9, 2016, 6 pages.

Han, Z. et al. (May 20, 2015, Apr. 15, 2015). "EDB Fibronectin Specific Peptide for Prostate Cancer Targeting," *Bioconjug Chem* 26(5):830-838.

Yang, J. et al. (Nov. 28, 2015, e-published Sep. 26, 2015). "FRET-trackable biodegradable HPMA copolymer-epirubicin conjugates for ovarian carcinoma therapy," *J Control Release* 218:36-44.

* cited by examiner

Cyanine 3 (Cy3)

Cyanine 5 (Cy5)

antiSTAT3-Cy5 antiSTAT3-sulfoCy5

BLANK

CELL PENETRATING CYANINE-COUPLED ANTIBODIES

CROSS REFERENCE TO RELATED APPLICATIONS

This application is a national stage application filed under 35 U.S.C. § 371, of International Patent Application No. PCT/US2016/066025, filed Dec. 9, 2016, which claims priority to U.S. Provisional Application No. 62/265,727, filed Dec. 10, 2015, which is hereby incorporated by reference in its entirety and for all purposes.

STATEMENT AS TO RIGHTS TO INVENTIONS MADE UNDER FEDERALLY SPONSORED RESEARCH AND DEVELOPMENT

This invention was made with government support under Grant No. RO1CA122976 awarded by the National Institutes of Health. The government has certain rights in the invention.

BACKGROUND OF THE INVENTION

With their excellent binding specificity and minimal off-target effects antibodies have proven to be an efficacious drug modality for its easy generation and bio-durability. However, numerous important targets for disease treatment and disease diagnosis are intracellular. Further, shuttling antibodies into cells is labor intensive and can also compromise the structural and functional integrity of the cell or the antibody itself. Therefore, there is a need in the art for therapeutic and diagnostic cell-penetrating antibodies. Provided herein are solutions for these and other needs in the art.

BRIEF SUMMARY OF THE INVENTION

In one aspect, a cell-penetrating conjugate having the formula:

(I)

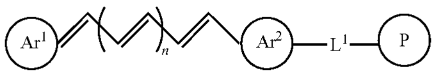

or (IV)

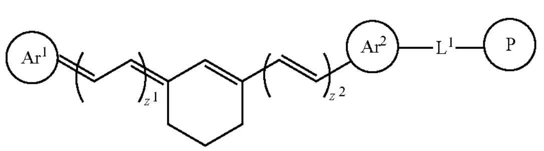

is provided. In formula (I) or (IV). $Ar^1$ is substituted or unsubstituted cycloalkyl, substituted or unsubstituted heterocycloalkyl, substituted or unsubstituted fused ring aryl or substituted or unsubstituted fused ring heteroaryl. $Ar^2$ is substituted or unsubstituted cycloalkylene, substituted or unsubstituted heterocycloalkylene, substituted or unsubstituted arylene or substituted or unsubstituted heteroarylene. $L^1$ is a bond, —C(O)—, —C(O)O—, —OC(O)—, —C(O)NH—, —NH—, —NHC(O)—, —O—, —S—, —S(O)—, —$S(O)_2$NH—, —NHS$(O)_2$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. P is a non-cell penetrating protein. The symbol n is an integer 1 or 2, and $z^1$ and $z^2$ are independently integers of 1 or 2.

In an aspect is provided a cell-penetrating conjugate having the formula:

(I)

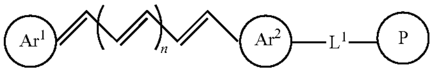

In formula (I) $Ar^1$ is substituted or unsubstituted cycloalkyl, substituted or unsubstituted heterocycloalkyl, substituted or unsubstituted fused ring aryl or substituted or unsubstituted fused ring heteroaryl. $Ar^2$ is substituted or unsubstituted cycloalkylene, substituted or unsubstituted heterocycloalkylene, substituted or unsubstituted arylene or substituted or unsubstituted heteroarylene. $L^1$ is substituted or unsubstituted alkylene or substituted or unsubstituted heteroalkylene. P is a non-cell penetrating protein and the symbol n is 1 or 2.

In an aspect is provided a cell comprising the cell penetrating conjugate as described herein including embodiments thereof.

In an aspect is provided a pharmaceutical composition comprising the cell penetrating conjugate as described herein including embodiments thereof and a pharmaceutically acceptable carrier.

In an aspect is provided is a method of delivering a non-cell penetrating protein into a cell. The method includes contacting a cell with the cell penetrating conjugate as described herein including embodiments thereof.

In an aspect is provided a method of treating a disease in a subject in need thereof. The method includes administering to a subject an effective amount of the cell penetrating conjugate as described herein including embodiments thereof, thereby treating the disease in the subject.

BRIEF DESCRIPTION OF THE DRAWINGS

FIG. 2A left panel: Cyanine5-Stat3-antibodies readily internalize into cells. Human B cell lymphoma Ly3 cells were incubated for 1 h at 10 μg/ml with cyanine- or sulfo-cyanine-Stat3-antibodies as indicated. Structure of cyanine 5: top of the left panel; structure of sulfo-cyanine 5: bottom of the left panel. FIG. 2A right panel. Confocal microscopic analysis of human B cell lymphoma Ly3 cells to assess cellular localization. Scale, 10 μm. FIG. 2B. Flow cytometric analysis showing cellular internalization efficacy of anti-Stat3-Cy5 human B cell lymphoma Ly3 cells. Neither anti-Stat3-sulfoCy5 nor any Cy3 label exerted cellular internalization indicating cellular penetration is restricted to anti-Stat3-Cy5 conjugate.

FIG. 4A shows Cy7 conjugates, Cyanine 7 and sulfo-Cyanine 7. Human B cell lymphoma Ly3 cells were incubated for times indicated at 10 μg/ml with cyanine- or sulfo-cyanine-Stat3-antibodies as indicated. Whole cell lysates were prepared and alternative immunoprecipitation was performed where protein-coupled agarose beads were added to lysates once cleared from cell debris. Target recognition was achieved exclusively by the anti-STAT3-Cy7 conjugate as shown by Western blot detection of STAT3 migration at predicted 89 kDa, shown in FIG. 4B.

DETAILED DESCRIPTION OF THE INVENTION

I. Definitions

Figure 1:
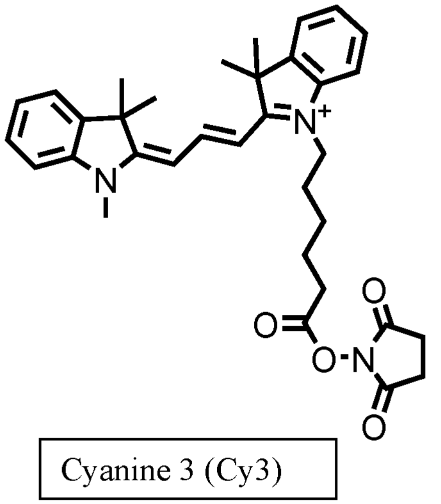
FIG. 1. Covalent linkage of cyanine 3 (Cy3) and cyanine 5 (Cy5) to anti-Stat3 antibodies via NHS ester. Cy3 (left panel, top structure) and Cy5 (left panel, bottom structure) were chosen to induce covalent ester binding to immunoglobulin anti-Stat3. Once the ester binding reaction was completed, anti-Stat3-Cy3 and anti-Stat3-Cy5 were subjected to SDS-PAGE under non-reducing conditions and an image of the SDS-PAGE gel was acquired visualizing fluorescently labeled Stat3-IgG migrating at a molecular range predicted for immunoglobulins 150 kDa (right panel).
Figure 1:
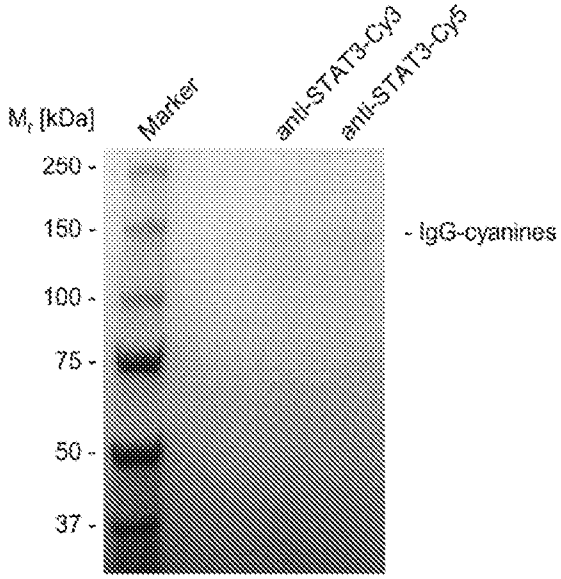
Figure 1:
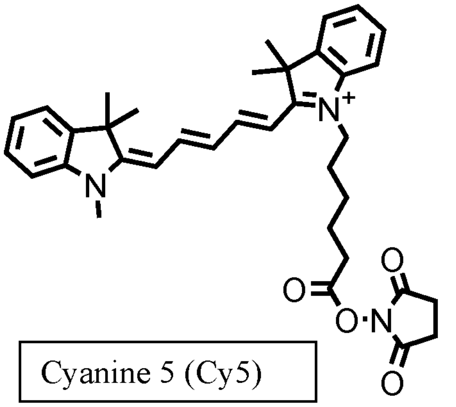

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., $—CH_2O—$ is equivalent to $—OCH_2—$.

The term "alkyl," by itself or as part of another substituent, means, unless otherwise stated, a straight (i.e., unbranched) or branched non-cyclic carbon chain (or carbon), or combination thereof, which may be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds (alkenyl) or triple bonds (alkynyl). An alkenyl may include more than one double bond and/or one or more triple bonds in addition to the one or more double bonds. An alkynyl may include more than one triple bond and/or one or more double bonds in addition to the one or more triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated.

The term "alkylene," by itself or as part of another substituent, means, unless otherwise stated, a divalent radical derived from an alkyl, as exemplified, but not limited by, $—CH_2CH_2CH_2CH_2—$. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched non-cyclic chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. Examples include, but are not limited to: $—CH_2—CH_2—O—CH_3$, $—CH_2—CH_2—NH—CH_3$, $—CH_2—CH_2—N(CH_3)—CH_3$, $—CH_2—S—CH_2—CH_3$, $—CH_2—CH_2$, $—S(O)—CH_3$, $—CH_2—CH_2—S(O)_2—CH_3$, $—CH=CHO—CH_3$, $—Si(CH_3)_3$, $—CH_2—CH=N—OCH_3$, $—CH=CH—N(CH_3)—CH_3$, $—O—CH_3$, $—O—CH_2—CH_3$, and —CN. Up to two or three heteroatoms may be consecutive, such as, for example, $—CH_2—NH—OCH_3$ and $—CH_2—O—Si(CH_3)_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds.

Similarly, the term "heteroalkylene," by itself or as part of another substituent, means, unless otherwise stated, a divalent radical derived from heteroalkyl, as exemplified, but not limited by, $—CH_2—CH_2—S—CH_2—CH_2—$ and $—CH_2—S—CH_2—CH_2—NH—CH_2—$. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —$C(O)_2R'$— represents both —$C(O)_2R'$— and —$R'C(O)_2$—. As described above, heteroalkyl groups, as used herein, include those groups that are attached to the remainder of the molecule through a heteroatom, such as —C(O)R', —C(O)NR', —NR'R", —OR', —SR', and/or —$SO_2R'$. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, non-aromatic cyclic versions of "alkyl" and "heteroalkyl," respectively, wherein the carbons making up the ring or rings do not necessarily need to be bonded to a hydrogen due to all carbon valencies participating in bonds with non-hydrogen atoms. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, 3-hydroxy-cyclobut-3-enyl-1,2, dione, 1H-1,2,4-triazolyl-5(4H)-one, 4H-1,2,4-triazolyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. A heterocycloalkyl moiety may include one ring heteroatom (e.g., O, N, S, Si, or P). A heterocycloalkyl moiety may include two optionally different ring heteroatoms (e.g., O, N, S, Si, or P). A heterocycloalkyl moiety may include three optionally different ring heteroatoms (e.g., O, N, S, Si, or P). A heterocycloalkyl moiety may include four optionally different ring heteroatoms (e.g., O, N, S, Si, or P). A heterocycloalkyl moiety may include five optionally different ring heteroatoms (e.g., O, N, S, Si, or P). A heterocycloalkyl moiety may include up to 8 optionally different ring heteroatoms (e.g., O, N, S, Si, or P). A "cycloalkylene" and a "heterocycloalkylene," alone or as part of another substituent, means a divalent radical derived from a cycloalkyl and heterocycloalkyl, respectively. The terms "cycloalkenyl" and "cycloalkynyl," by themselves or in combination with other terms, mean, unless otherwise stated, non-aromatic cyclic versions of "alkenyl" and "alkynyl," respectively. The terms "heterocycloalkenyl" and "heterocycloalkynyl," by themselves or in combination with other terms, mean, unless otherwise stated, cyclic versions of "heteroalkenyl" and "heteroalkynyl," respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Non-limiting examples of heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein.

The term "oxo," as used herein, means an oxygen that is double bonded to a carbon atom.

The term "alkylarylene" as an arylene moiety covalently bonded to an alkylene moiety (also referred to herein as an alkylene linker). In embodiments, the alkylarylene group has the formula:

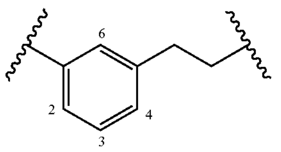

or

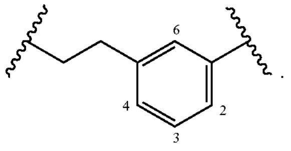

An alkylarylene moiety may be substituted (e.g. with a substituent group) on the alkylene moiety or the arylene linker (e.g. at carbons 2, 3, 4, or 6) with halogen, oxo, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2CH_3$—$SO_3H$, —$OSO_3H$, —$SO_2NH_2$, —$NHNH_2$, —$ONH_2$, —$NHC(O)NHNH_2$, substituted or unsubstituted $C_1$-$C_5$ alkyl or substituted or unsubstituted 2 to 5 membered heteroalkyl). In embodiments, the alkylarylene is unsubstituted.

The term "alkylsulfonyl," as used herein, means a moiety having the formula —$S(O_2)$—R', where R' is a substituted or unsubstituted alkyl group as defined above. R' may have a specified number of carbons (e.g., "$C_1$-$C_4$ alkylsulfonyl").

Each of the above terms (e.g., "alkyl", "heteroalkyl", "cycloalkyl", "heterocycloalkyl", "aryl", and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', ═O, ═NR', ═N—OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR" R', —NR"$C(O)_2$R', —NR—C(NR'R"R'")═NR"", —NR—C(NR'R")═NR'", —S(O)R', —$S(O)_2$R', —$S(O)_2$NR' R", —$NRSO_2$R', —NR'NR"R", —ONR'R", —NR'C═(O)NR"NR'"R"", —CN, —$NO_2$, monophosphate (or derivatives thereof), diphosphate (or derivatives thereof), triphosphate (or derivatives thereof), in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —$C(O)CH_3$, —$C(O)CF_3$, —$C(O)CH_2OCH_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR" R', —NR"$C(O)_2$R', —NR—C(NR'R"R'")═NR"", —NR—C(NR'R")═NR'", —S(O)R', —$S(O)_2$R', —$S(O)_2$NR' R", —$NRSO_2$R', —NR'NR"R", —ONR'R", —NR'C═(O)NR"NR'"R"", —CN, —$NO_2$, —R', —$N_3$, —$CH(Ph)_2$, fluoro($C_1$-$C_4$)alkoxy, and fluoro($C_1$-$C_4$)alkyl, in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R'", and R"" groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—$(CRR')_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-$(CH_2)_r$—B—, wherein A and B are independently —CRR'—, —O—, —NR—, —S—, —S(O)—, —$S(O)_2$—, —$S(O)_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —$(CRR')_s$—X'—$(C"R"R'")_d$—, where s and d are independently integers of from 0 to 3, and X' is —O—, —NR'—, —S—, —S(O)—, —$S(O)_2$—, or —$S(O)_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties:

(A) oxo, halogen, $-CF_3$, $-CCl_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC{=}(O)NHNH_2$, $-NHC{=}(O)\ NH_2$, $-NHSO_2H$, $-NHC{=}(O)H$, $-NHC(O)-OH$, $-NHOH$, $-OCF_3$, $-OCHF_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, heteroaryl, substituted with at least one substituent selected from:

(i) oxo, halogen, $-CF_3$, $-CCl_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC{=}(O)NHNH_2$, $-NHC{=}(O)\ NH_2$, $-NHSO_2H$, $-NHC{=}(O)H$, $-NHC(O)-OH$, $-NHOH$, $-OCF_3$, $-OCHF_2$, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, heteroaryl, substituted with at least one substituent selected from:

(a) oxo, halogen, $-CF_3$, $-CCl_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC{=}(O)NHNH_2$, $-NHC{=}(O)\ NH_2$, $-NHSO_2H$, $-NHC{=}(O)H$, $-NHC(O)-OH$, $-NHOH$, $-OCF_3$, $-OCHF_2$, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, heteroaryl, substituted with at least one substituent selected from: oxo, halogen, $-CF_3$, $-CCl_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC{=}(O)NHNH_2$, $-NHC{=}(O)\ NH_2$, $-NHSO_2H$, $-NHC{=}(O)H$, $-NHC(O)-OH$, $-NHOH$, $-OCF_3$, $-OCHF_2$, unsubstituted alkyl, unsubstituted heteroalkyl, unsubstituted cycloalkyl, unsubstituted heterocycloalkyl, unsubstituted aryl, unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section below.

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, NY 1994); Sambrook et al., MOLECULAR CLONING, A LABORATORY MANUAL, Cold Springs Harbor Press (Cold Springs Harbor, NY 1989). Any methods, devices and materials similar or equivalent to those described herein can be used in the practice of this invention. The following definitions are provided to facilitate understanding of certain terms used frequently herein and are not meant to limit the scope of the present disclosure.

The term "exogenous" refers to a molecule or substance (e.g., a compound, nucleic acid or protein) that originates from outside a given cell or organism. For example, an "exogenous promoter" as referred to herein is a promoter that does not originate from the plant it is expressed by. Conversely, the term "endogenous" or "endogenous promoter" refers to a molecule or substance that is native to, or originates within, a given cell or organism.

The term "isolated", when applied to a nucleic acid or protein, denotes that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified.

The terms "polypeptide," "peptide" and "protein" are used interchangeably herein to refer to a polymer of amino acid residues, wherein the polymer may In embodiments be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. A "fusion protein" refers to a chimeric protein encoding two or more separate protein sequences that are recombinantly expressed as a single moiety.

The term "peptidyl" and "peptidyl moiety" means a monovalent peptide.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, "conservatively modified variants" refers to those nucleic acids that encode identical or essentially identical amino acid sequences. Because of the degeneracy of the genetic code, a number of nucleic acid sequences will encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

(see, e.g., Creighton, *Proteins* (1984)).

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding. In some embodiments, antibodies or fragments of antibodies may be derived from different organisms, including humans, mice, rats, hamsters, camels, etc. Antibodies of the invention may include antibodies that have been modified or mutated at one or more amino acid positions to improve or modulate a desired function of the antibody (e.g. glycosylation, expression, antigen recognition, effector functions, antigen binding, specificity, etc.).

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively. The Fc (i.e. fragment crystallizable region) is the "base" or "tail" of an immunoglobulin and is typically composed of two heavy chains that contribute two or three constant domains depending on the class of the antibody. By binding to specific proteins the Fc region ensures that each antibody generates an appropriate immune response for a given antigen. The Fc region also binds to various cell receptors, such as Fc receptors, and other immune molecules, such as complement proteins.

Antibodies exist, for example, as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region, thereby converting the F(ab)'2 dimer into an Fab' monomer. The Fab' monomer is essentially the antigen dinging portion with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., Nature 348:552-554 (1990)).

A single-chain variable fragment (scFv) is typically a fusion protein of the variable regions of the heavy (VH) and light chains (VL) of immunoglobulins, connected with a short linker peptide of 10 to about 25 amino acids. The linker may usually be rich in glycine for flexibility, as well as serine or threonine for solubility. The linker can either connect the N-terminus of the VH with the C-terminus of the VL, or vice versa.

For preparation of suitable antibodies of the invention and for use according to the invention, e.g., recombinant, monoclonal, or polyclonal antibodies, many techniques known in the art can be used (see, e.g., Kohler & Milstein, Nature 256:495-497 (1975); Kozbor et al., Immunology Today 4: 72 (1983); Cole et al., pp. 77-96 in Monoclonal Antibodies and Cancer Therapy, Alan R. Liss, Inc. (1985); Coligan, Current Protocols in Immunology (1991); Harlow & Lane, Antibodies, A Laboratory Manual (1988); and Goding, Monoclonal Antibodies: Principles and Practice (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, Immunology (3rd ed. 1997)). Techniques for the production of single chain antibodies or recombinant antibodies (U.S. Pat. Nos. 4,946,778, 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., Bio/Technology 10:779-783 (1992); Lonberg et al., Nature 368:856-859 (1994); Morrison, Nature 368:812-13 (1994); Fishwild et al., Nature Biotechnology 14:845-51 (1996); Neuberger, Nature Biotechnology 14:826 (1996); and Lonberg & Huszar, Intern. Rev. Immunol. 13:65-93 (1995)). Alternatively, phage display technology can be used to identify antibodies and heteromeric Fab fragments that specifically bind to selected antigens (see, e.g., McCafferty et al., Nature 348:552-554 (1990); Marks et al., Biotechnology 10:779-783 (1992)). Antibodies can also be made bispecific, i.e., able to recognize two different antigens (see, e.g., WO 93/08829, Traunecker et al., EMBO J. 10:3655-3659 (1991); and Suresh et al., Methods in Enzymology 121:210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Methods for humanizing or primatizing non-human antibodies are well known in the art (e.g., U.S. Pat. Nos. 4,816,567; 5,530,101; 5,859,205; 5,585,089; 5,693,761; 5,693,762; 5,777,085; 6,180,370; 6,210,671; and 6,329,511; WO 87/02671; EP Patent Application 0173494; Jones et al. (1986) Nature 321:522; and Verhoyen et al. (1988) Science 239:1534). Humanized antibodies are further described in, e.g., Winter and Milstein (1991) Nature 349:293. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Morrison et al., PNAS USA, 81:6851-6855 (1984), Jones et al., Nature 321:522-525 (1986); Riechmann et al., Nature 332:323-327 (1988); Morrison and Oi, Adv. Immunol., 44:65-92 (1988), Verhoeyen et al., Science 239:1534-1536 (1988) and Presta, Curr. Op. Struct. Biol. 2:593-596 (1992), Padlan, Molec. Immun., 28:489-498 (1991); Padlan, Molec. Immun., 31(3):169-217 (1994)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies. For example, polynucleotides comprising a first sequence coding for humanized immunoglobulin framework regions and a second sequence set coding for the desired immunoglobulin complementarity determining regions can be produced synthetically or by combining appropriate cDNA and genomic DNA segments. Human constant region DNA sequences can be isolated in accordance with well known procedures from a variety of human cells.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. The preferred antibodies of, and for use according to the invention include humanized and/or chimeric monoclonal antibodies.

Techniques for conjugating therapeutic agents to antibodies are well known (see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery" in Controlled Drug Delivery ($2^{nd}$ Ed.), Robinson et al. (eds.), pp. 623-53 (Marcel Dekker, Inc. 1987); Thorpe, "Antibody Carriers Of Cytotoxic Agents In Cancer Therapy: A Review" in Monoclonal Antibodies '84: Biological And Clinical Applications, Pinchera et al. (eds.), pp. 475-506 (1985); and Thorpe et al., "The Preparation And Cytotoxic Properties Of Antibody-Toxin Conjugates", Immunol. Rev., 62:119-58 (1982)). As used herein, the term "antibody-drug conjugate" or "ADC" refers to a therapeutic agent conjugated or otherwise covalently bound to an antibody. A "therapeutic agent" as referred to herein, is a composition useful in treating or preventing a disease such as cancer.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies can be selected to obtain only a subset of antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998) for a description of immunoassay formats and conditions that can be used to determine specific immunoreactivity).

A "label" or a "detectable moiety" is a composition detectable by spectroscopic, photochemical, biochemical, immunochemical, chemical, or other physical means. For example, useful labels include 32P, fluorescent dyes (e.g. cyanine), electron-dense reagents, enzymes (e.g., as commonly used in an ELISA), biotin, digoxigenin, or haptens and proteins or other entities which can be made detectable, e.g., by incorporating a radiolabel into a peptide or antibody specifically reactive with a target peptide. Any appropriate method known in the art for conjugating an antibody to the label may be employed, e.g., using methods described in Hermanson, Bioconjugate Techniques 1996, Academic Press, Inc., San Diego.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be, for example, an antibody domain as described herein and an antibody-binding domain. In embodiments contacting includes, for example, allowing an antibody domain as described herein to interact with an antibody-binding domain.

"Patient" or "subject in need thereof" refers to a living organism suffering from or prone to a disease or condition that can be treated by administration of a composition or pharmaceutical composition as provided herein. Non-limiting examples include humans, other mammals, bovines, rats, mice, dogs, monkeys, goat, sheep, cows, deer, and other non-mammalian animals. In some embodiments, a patient is human.

The terms "disease" or "condition" refer to a state of being or health status of a patient or subject capable of being treated with a compound, pharmaceutical composition, or method provided herein. In embodiments, the disease is cancer (e.g. lung cancer, ovarian cancer, osteosarcoma, bladder cancer, cervical cancer, liver cancer, kidney cancer, skin cancer (e.g., Merkel cell carcinoma), testicular cancer, leukemia, lymphoma, head and neck cancer, colorectal cancer, prostate cancer, pancreatic cancer, melanoma, breast cancer, neuroblastoma). The disease may be an autoimmune, inflammatory, cancer, infectious, metabolic, developmental, cardiovascular, liver, intestinal, endocrine, neurological, or other disease.

As used herein, the term “cancer” refers to all types of cancer, neoplasm or malignant tumors found in mammals, including leukemias, lymphomas, melanomas, neuroendocrine tumors, carcinomas and sarcomas. Exemplary cancers that may be treated with a compound, pharmaceutical composition, or method provided herein include lymphoma, sarcoma, bladder cancer, bone cancer, brain tumor, cervical cancer, colon cancer, esophageal cancer, gastric cancer, head and neck cancer, kidney cancer, myeloma, thyroid cancer, leukemia, prostate cancer, breast cancer (e.g. triple negative, ER positive, ER negative, chemotherapy resistant, herceptin resistant, HER2 positive, doxorubicin resistant, tamoxifen resistant, ductal carcinoma, lobular carcinoma, primary, metastatic), ovarian cancer, pancreatic cancer, liver cancer (e.g. Hepatocellular carcinoma), lung cancer (e.g. non-small cell lung carcinoma, squamous cell lung carcinoma, adenocarcinoma, large cell lung carcinoma, small cell lung carcinoma, carcinoid, sarcoma), glioblastoma multiforme, glioma, melanoma, prostate cancer, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma. Additional examples include, cancer of the thyroid, endocrine system, brain, breast, cervix, colon, head & neck, esophagus, liver, kidney, lung, non-small cell lung, melanoma, mesothelioma, ovary, sarcoma, stomach, uterus or Medulloblastoma, Hodgkin’s Disease, Non-Hodgkin’s Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget’s Disease of the Nipple, Phyllodes Tumors, Lobular Carcinoma, Ductal Carcinoma, cancer of the pancreatic stellate cells, cancer of the hepatic stellate cells, or prostate cancer.

The term “leukemia” refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound, pharmaceutical composition, or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross’ leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling’s leukemia, stem cell leukemia, subleukemic leukemia, or undifferentiated cell leukemia.

The term “sarcoma” generally refers to a tumor which is made up of a substance like the embryonic connective tissue and is generally composed of closely packed cells embedded in a fibrillar or homogeneous substance. Sarcomas that may be treated with a compound, pharmaceutical composition, or method provided herein include a chondrosarcoma, fibrosarcoma, lymphosarcoma, melanosarcoma, myxosarcoma, osteosarcoma, Abemethy’s sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms’ tumor sarcoma, endometrial sarcoma, stromal sarcoma, Ewing’s sarcoma, fascial sarcoma, fibroblastic sarcoma, giant cell sarcoma, granulocytic sarcoma, Hodgkin’s sarcoma, idiopathic multiple pigmented hemorrhagic sarcoma, immunoblastic sarcoma of B cells, lymphoma, immunoblastic sarcoma of T-cells, Jensen’s sarcoma, Kaposi’s sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term “melanoma” is taken to mean a tumor arising from the melanocytic system of the skin and other organs. Melanomas that may be treated with a compound, pharmaceutical composition, or method provided herein include, for example, acral-lentiginous melanoma, amelanotic melanoma, benign juvenile melanoma, Cloudman’s melanoma, S91 melanoma, Harding-Passey melanoma, juvenile melanoma, lentigo maligna melanoma, malignant melanoma, nodular melanoma, subungal melanoma, or superficial spreading melanoma.

The term “carcinoma” refers to a malignant new growth made up of epithelial cells tending to infiltrate the surrounding tissues and give rise to metastases. Exemplary carcinomas that may be treated with a compound, pharmaceutical composition, or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, ductal carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lobular carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tubular carcinoma, tuberous carcinoma, verrucous carcinoma, or carcinoma villosum.

As used herein, the terms "metastasis," "metastatic," and "metastatic cancer" can be used interchangeably and refer to the spread of a proliferative disease or disorder, e.g., cancer, from one organ or another non-adjacent organ or body part. Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

As used herein, an "autoimmune disease" refers to a disease or disorder that arises from altered immune reactions by the immune system of a subject, e.g., against substances tissues and/or cells normally present in the body of the subject. Autoimmune diseases include, but are not limited to, arthritis, rheumatoid arthritis, psoriatic arthritis, juvenile idiopathic arthritis, scleroderma, systemic scleroderma, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, autoimmune thyroiditis, Behcet's disease, Crohn's disease, ulcerative colitis, bullous pemphigoid, sarcoidosis, psoriasis, ichthyosis, Graves ophthalmopathy, inflammatory bowel disease, Addison's disease, Vitiligo, asthma, and allergic asthma.

As used herein, an "inflammatory disease" refers to a disease or disorder associated with abnormal or altered inflammation. Inflammation is a biological response initiated by the immune system as part of the healing process in response to a pathogen, damaged cells or tissues or irritants. Chronic inflammation can lead to a variety of diseases. Inflammatory diseases include, but are not limited to, atherosclerosis, allergies, asthma, rheumatoid arthritis, transplant rejection, celiac disease, chronic prostatitis, inflammatory bowel diseases, pelvic inflammatory diseases, and inflammatory myopathies.

As used herein, "metabolic disorders" refer to diseases or disorders involving abnormal metabolism of a variety of molecules and substances including, for example, carbohydrates, amino acids, organic acids. Metabolic disorders include, but are not limited to, disorders of carbohydrate metabolism, e.g., glycogen storage disease, disorders of amino acid metabolism, e.g., phenylketonuria, maple syrup urine disease, glutaric acidemia type 1, urea cycle disorder or urea cycle defects, e.g., carbamoyl phosphate synthetase I deficiency, disorders of organic acid metabolism (organic acidurias), e.g., alcaptonuria, disorders of fatty acid oxidation and mitochondrial metabolism, e.g., medium-chain acyl-coenzyme A dehydrogenase deficiency, disorders of porphyrin metabolism, e.g., acute intermittent porphyria, disorders of purine or pyrimidine metabolism, e.g., Lesch-Nyhan syndrome, disorders of steroid metabolism, e.g., lipoid congenital adrenal hyperplasia, congenital adrenal hyperplasia, disorders of mitochondrial function, e.g., Kearns-Sayre syndrome, disorders of peroxisomal function, e.g., Zellweger syndrome, and lysosomal storage disorders, e.g., Gaucher's disease, and Niemann Pick disease.

As used herein, "developmental disorders" refer to diseases or disorders often originating in childhood associated with language disorders, learning disorders, motor disorders and neurodevelopmental disorders. Examples include, but are not limited to, autism spectrum disorders and attention deficit disorders.

As used herein, "cardiovascular diseases" refer to diseases associated with the heart, blood vessels or both. Cardiovascular diseases include, but are not limited to, coronary heart disease, cardiomyopathy, hypertensive heart disease, heart failure, cardiac dysrhythmias, inflammatory heart disease, peripheral arterial disease, cerebrovascular disease and inflammatory heart disease.

As used herein, "liver diseases" refer to diseases associated with the abnormalities in the liver and/or liver function. Liver diseases include, but are not limited to, hepatitis, alcoholic liver disease, fatty liver disease, cirrhosis, Budd-Chiari syndrome, Gilbert's syndrome and cancer.

As used herein, the term "intestinal disease" refers to diseases or disorders associated with abnormalities in the intestine (small or large). Intestinal diseases include, but are not limited to, gastroenteritis, colitis, ileitis, appendicitis, coeliac disease, Chron's disease, enteroviruses, irritable bowel syndrome, and diverticular disease.

As used herein, the term "endocrine disease" refers to diseases or disorders of the endocrine system including endocrine gland hyposecretion, endocrine gland hypersecretion and tumors. Endocrine diseases include, but are not limited to, Addison's disease, diabetes, Conn's syndrome, Cushing's syndrome, glucocorticoid remediable aldosteronism, hypoglycemia, hyperthyroidism, hypothyroidism, thyroiditis, hypopituitarism, hypogonadism and parathyroid gland disorders.

As used herein, the term "neurological disorder" refers to diseases or disorders of the bodies nervous system including structural, biochemical or electrical abnormalities. Neurological disorders include, but are not limited to, brain damage, brain dysfunction, spinal cord disorders, peripheral neuropathies, cranial nerve disorders, autonomic nervous system disorders, seizure disorders, movement disorders, e.g., Parkinson's disease and Multiple Sclerosis, and central neuropathies.

As used herein, the term "infectious disease" refers to diseases or disorders associate with infection, presence and/or growth of a pathogenic agent in a host subject. Infectious pathogenic agents include, but are not limited to, viruses, bacteria, fungi, protozoa, multicellular parasites and aberrant proteins, e.g., prions. Viruses associated with infectious disease include but are not limited to, herpes simplex viruses, cytomegalovirus, Epstein-Barr virus, Varicella-zoster virus, herpesviruses, Vesicular stomatitis virus, Hepatitis viruses, Rhinovirus, Coronavirus, Influenza viruses, Measles virus, Polyomavirus, Human Papilomavirus, Respiratory syncytial virus, Adenovirus, Coxsackie virus, Dengue virus, Mumps virus, Poliovirus, Rabies virus, Rous sarcoma virus, Yellow fever virus, Ebola virus, Simian Immunodeficiency viruses, Human Immunodeficiency viruses. Bacteria associated with infectious disease include, but are not limited to, *M. tuberculosis, Salmonella species, E. coli, Chlamydia species, Staphylococcus species, Bacillus species*, and *Pseudomonas* species.

The term "associated" or "associated with" in the context of a substance or substance activity or function associated with a disease (e.g., diabetes, cancer (e.g. prostate cancer, renal cancer, metastatic cancer, melanoma, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma)) means that the disease (e.g. lung cancer, ovarian cancer, osteosarcoma, bladder cancer, cervical cancer, liver cancer, kidney cancer, skin cancer (e.g., Merkel cell carcinoma), testicular cancer, leukemia, lymphoma, head and neck cancer, colorectal cancer, prostate cancer, pancreatic cancer, melanoma, breast cancer, neuroblastoma) is caused by (in whole or in part), or a symptom of the disease is caused by (in whole or in part) the substance or substance activity or function.

The term "aberrant" as used herein refers to different from normal. When used to describe enzymatic activity, aberrant refers to activity that is greater or less than a normal control or the average of normal non-diseased control samples. Aberrant activity may refer to an amount of activity that results in a disease, wherein returning the aberrant activity to a normal or non-disease-associated amount (e.g. by using a method as described herein), results in reduction of the disease or one or more disease symptoms.

As used herein, the terms "cell-penetrating" or "cell-penetration" refer to the ability of a molecule (e.g., a protein) to pass from the extracellular environment into a cell in a significant or effective amount. Thus, a cell-penetrating conjugate is a molecule that passes from the extracellular environment, through the membrane, and into a cell.

As used herein, the terms "non-cell penetrating" or "non-cell penetration" refers to the inability of a molecule (e.g., a protein or peptide) to pass from the extracellular environment into a cell in a significant or effective amount. Thus, non-cell penetrating peptides or proteins generally are not capable of passing from the extracellular environment, through the cell membrane, and into a cell in order to achieve a significant biological effect on a population of cells, organ or organism. The term does not exclude the possibility that one or more of the small number of peptides or proteins may enter the cell. However, the term refers to molecules that are generally not able to enter a cell from the extracellular environment to a significant degree. Examples of non-cell penetrating molecules and substances include, but are not limited to, large molecules such as, for example, high molecular weight proteins. Peptides or proteins can be determined to be non-cell penetrating using methods known to those of skill in the art. By way of example, a peptide or protein can be fluorescently labeled and the ability of the peptide or protein to pass from the extracellular environment into the cell can be determined in vitro by flow cytometric analysis or confocal microscopy.

As used herein, "molecular weight" (M.W.) or "molecular mass" refers to the sum of the atomic weights of all the atoms in a molecule. With respect to molecules, a molecule with a high molecular weight typically has a molecular weight of 25 kDa or more. By way of example, a high molecular weight protein can have a M.W. from about 25 kDa to 1000 kDa or more.

As used herein, the term "intracellular" means inside a cell. As used herein, an "intracellular target" is a target, e.g., nucleic acid, polypeptide or other molecule (e.g., carbohydrate) that is located inside of a cell and is a target to which the non-cell penetrating proteins provided herein bind. Binding can be direct or indirect. In embodiments, the non-cell penetrating protein selectively binds the intracellular target. The terms "selectively binds," "selectively binding," or "specifically binding" refer to an agent (e.g., a non-cell penetrating protein) binding one agent (e.g., intracellular target) to the partial or complete exclusion of other agents. By binding is meant a detectable binding at least about 1.5 times the background of the assay method. For selective or specific binding such a detectable binding can be detected for a given agent but not a control agent. Alternatively, or additionally, the detection of binding can be determined by assaying the presence of down-stream molecules or events.

As used herein, the term "conjugate" refers to the association between atoms or molecules. The association can be direct or indirect. For example, a conjugate between a nucleic acid and a protein or a protein and a protein, can be direct, e.g., by covalent bond, or indirect, e.g., by non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). In embodiments, conjugates are formed using conjugate chemistry including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

Useful reactive moieties including covalent reactive moieties or functional groups used for conjugate chemistries herein include, for example:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;
(b) hydroxyl groups which can be converted to esters, ethers, aldehydes, etc.
(c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;
(d) dienophile groups which are capable of participating in Diels-Alder reactions such as, for example, maleimido groups;
(e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;
(f) sulfonyl halide groups for subsequent reaction with amines, for example, to form sulfonamides;
(g) thiol groups, which can be converted to disulfides, reacted with acyl halides, or bonded to metals such as gold;
(h) amine or sulfhydryl groups, which can be, for example, acylated, alkylated or oxidized;
(i) alkenes, which can undergo, for example, cycloadditions, acylation, Michael addition, etc;
(j) epoxides, which can react with, for example, amines and hydroxyl compounds;
(k) phosphoramidites and other standard functional groups useful in nucleic acid synthesis;
(l) metal silicon oxide bonding;
(m) metal bonding to reactive phosphorus groups (e.g. phosphines) to form, for example, phosphate diester bonds; and
(n) sulfones, for example, vinyl sulfone.

The reactive functional groups can be chosen such that they do not participate in, or interfere with, the chemical stability of the proteins described herein.

A "control" or "standard control" refers to a sample, measurement, or value that serves as a reference, usually a known reference, for comparison to a test sample, measurement, or value. For example, a test sample can be taken from a patient suspected of having a given disease (e.g. an autoimmune disease, inflammatory autoimmune disease, cancer, infectious disease, immune disease, or other disease) and compared to a known normal (non-diseased) individual (e.g. a standard control subject). A standard control can also represent an average measurement or value gathered from a population of similar individuals (e.g. standard control subjects) that do not have a given disease (i.e. standard control population), e.g., healthy individuals with a similar medical background, same age, weight, etc. A standard control value can also be obtained from the same individual, e.g. from an earlier-obtained sample from the patient prior to disease onset. For example, a control can be devised to compare therapeutic benefit based on pharmacological data (e.g., half-life) or therapeutic measures (e.g., comparison of side effects). Controls are also valuable for determining the significance of data. For example, if values for a given parameter are widely variant in controls, variation in test samples will not be considered as significant. One of skill will recognize that standard controls can be designed for assessment of any number of parameters (e.g. RNA levels, protein levels, specific cell types, specific bodily fluids, specific tissues, synoviocytes, synovial fluid, synovial tissue, fibroblast-like synoviocytes, macrophagelike synoviocytes, etc).

One of skill in the art will understand which standard controls are most appropriate in a given situation and be able to analyze data based on comparisons to standard control values. Standard controls are also valuable for determining the significance (e.g. statistical significance) of data. For example, if values for a given parameter are widely variant in standard controls, variation in test samples will not be considered as significant.

The term "diagnosis" refers to a relative probability that a disease (e.g. an autoimmune, inflammatory autoimmune, cancer, infectious, immune, or other disease) is present in the subject. Similarly, the term "prognosis" refers to a relative probability that a certain future outcome may occur in the subject with respect to a disease state. For example, in the context of the present invention, prognosis can refer to the likelihood that an individual will develop a disease (e.g. an autoimmune, inflammatory autoimmune, cancer, infectious, immune, or other disease), or the likely severity of the disease (e.g., duration of disease). The terms are not intended to be absolute, as will be appreciated by any one of skill in the field of medical diagnostics.

"Biological sample" or "sample" refer to materials obtained from or derived from a subject or patient. A biological sample includes sections of tissues such as biopsy and autopsy samples, and frozen sections taken for histological purposes. Such samples include bodily fluids such as blood and blood fractions or products (e.g., serum, plasma, platelets, red blood cells, and the like), sputum, tissue, cultured cells (e.g., primary cultures, explants, and transformed cells) stool, urine, synovial fluid, joint tissue, synovial tissue, synoviocytes, fibroblast-like synoviocytes, macrophage-like synoviocytes, immune cells, hematopoietic cells, fibroblasts, macrophages, T cells, etc. A biological sample is typically obtained from a eukaryotic organism, such as a mammal such as a primate e.g., chimpanzee or human; cow; dog; cat; a rodent, e.g., guinea pig, rat, mouse; rabbit; or a bird; reptile; or fish.

A "cell" as used herein, refers to a cell carrying out metabolic or other functions sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., spodoptera) and human cells. Cells may be useful when they are naturally nonadherent or have been treated not to adhere to surfaces, for example by trypsinization.

The term "cyanine" or "cyanine moiety" as described herein refers to a compound containing two nitrogen groups separated by a polymethine chain. In embodiments, the cyanine moiety has 3 methine structures (i.e. cyanine 3). In embodiments, the cyanine moiety has 5 methine structures (i.e. cyanine 5). In embodiments, the cyanine moiety has 7 methine structures (i.e. cyanine 7). The cyanine moiety may be unsubstituted. The cyanine moiety may be substituted.

Where a moiety is substituted (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene), the moiety is substituted with at least one substituent (e.g., a substituent group, a size-limited substituent group, or lower substituent group) and each substituent is optionally different. Additionally, where multiple substituents are present on a moiety, each substituent may be optionally differently.

II. Cell-Penetrating Conjugates

Provided herein are, inter alia, cell-penetrating conjugates including a non-cell penetrating protein (e.g., antibody). The conjugates and methods provided herein provide highly effective means for delivering non-cell penetrating proteins (e.g., antibodies) into a cell for therapeutic and diagnostic purposes. The conjugates provided herein include a non-cell penetrating protein, such as an antibody, bound to a compound moiety through a linker ($L^1$). The compound moiety includes two aromatic moieties ($Ar^1$ and $Ar^2$) connected through an unsaturated alkylene (formula (I)) or alkylarylene (formula (IV)) linker. The compound moiety may be a cyanine moiety. Non-limiting examples of cyanine moieties are cyanine 5 or cyanine 7.

In one aspect, a cell-penetrating conjugate having the formula:

(I)

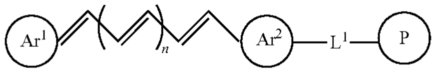

or (IV)

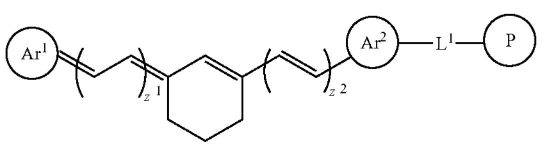

is provided. In formula (I) or (IV), $Ar^1$ is substituted or unsubstituted cycloalkyl, substituted or unsubstituted heterocycloalkyl, substituted or unsubstituted fused ring aryl or substituted or unsubstituted fused ring heteroaryl. $Ar^2$ is substituted or unsubstituted cycloalkylene, substituted or unsubstituted heterocycloalkylene, substituted or unsubstituted arylene or substituted or unsubstituted heteroarylene. $L^1$ is a bond, —C(O)—, —C(O)O—, —OC(O)—, —C(O)NH—, —NH—, —NHC(O)—, —O—, —S—, —S(O)—, —$S(O)_2$NH—, —NHS$(O)_2$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^1$ is substituted or unsubstituted (e.g., $C_1$-$C_{10}$) alkylene or substituted or unsubstituted (e.g., 1 to 10 membered) heteroalkylene substituted or unsubstituted alkylene or substituted or unsubstituted heteroalkylene. P is a non-cell penetrating protein. The symbol n is 1 or 2, and the symbols $z^1$ and $z^2$ are independently 1 or 2.

In embodiments the cell-penetrating conjugate has the formula (I)

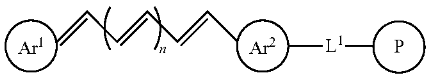

wherein $Ar^1$, n, $Ar^2$, $L^1$, and P are as defined above and herein, including embodiments thereof. In embodiments the cell-penetrating conjugate has the formula (IV)

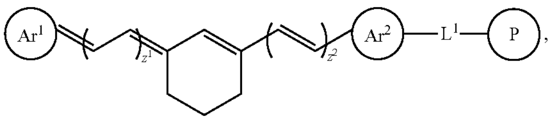

, wherein $Ar^1$, $z^1$, $z^2$, $Ar^2$, $L^1$, and P are as defined above and herein, including embodiments thereof.

In embodiments, $Ar^1$ is substituted or unsubstituted $C_4$-$C_{10}$ cycloalkyl. In embodiments, $Ar^1$ is substituted or unsubstituted $C_6$-$C_{10}$ cycloalkyl. In embodiments, $Ar^1$ is substituted or unsubstituted $C_7$-$C_{10}$ cycloalkyl. In embodiments, $Ar^1$ is substituted or unsubstituted $C_8$-$C_{10}$ cycloalkyl. In embodiments, $Ar^1$ is substituted or unsubstituted $C_9$-$C_{10}$ cycloalkyl. In embodiments, $Ar^1$ is unsubstituted $C_5$-$C_{10}$ cycloalkyl. In embodiments, $Ar^1$ is unsubstituted $C_6$-$C_{10}$ cycloalkyl. In embodiments, $Ar^1$ is unsubstituted $C_7$-$C_{10}$ cycloalkyl. In embodiments, $Ar^1$ is unsubstituted $C_8$-$C_{10}$ cycloalkyl. In embodiments, $Ar^1$ is unsubstituted $C_9$-$C_{10}$ cycloalkyl. In embodiments, $Ar^1$ is independently substituted $C_5$-$C_{10}$ cycloalkyl. In embodiments, $Ar^1$ is independently substituted $C_6$-$C_{10}$ cycloalkyl. In embodiments, $Ar^1$ is independently substituted $C_7$-$C_{10}$ cycloalkyl. In embodiments, $Ar^1$ is independently substituted $C_8$-$C_{10}$ cycloalkyl. In embodiments, $Ar^1$ is independently substituted $C_9$-$C_{10}$ cycloalkyl. In embodiments, $Ar^1$ is independently substituted $C_5$ or $C_6$ cycloalkyl.

In embodiments, $Ar^1$ is substituted or unsubstituted $C_5$-$C_{10}$ aryl. In embodiments, $Ar^1$ is substituted or unsubstituted $C_6$-$C_{10}$ aryl. In embodiments, $Ar^1$ is substituted or unsubstituted $C_7$-$C_{10}$ aryl. In embodiments, $Ar^1$ is substituted or unsubstituted $C_8$-$C_{10}$ aryl. In embodiments, $Ar^1$ is substituted or unsubstituted $C_9$-$C_{10}$ aryl. In embodiments, $Ar^1$ is unsubstituted $C_5$-$C_{10}$ aryl. In embodiments, $Ar^1$ is unsubstituted $C_6$-$C_{10}$ aryl. In embodiments, $Ar^1$ is unsubstituted $C_7$-$C_{10}$ aryl. In embodiments, $Ar^1$ is unsubstituted $C_8$-$C_{10}$ aryl. In embodiments, $Ar^1$ is unsubstituted $C_9$-$C_{10}$ aryl. In embodiments, $Ar^1$ is independently substituted phenyl. In embodiments, $Ar^1$ is independently substituted $C_5$-$C_{10}$ aryl. In embodiments, $Ar^1$ is independently substituted $C_6$-$C_{10}$ aryl. In embodiments, $Ar^1$ is independently substituted $C_7$-$C_{10}$ aryl. In embodiments, $Ar^1$ is independently substituted $C_8$-$C_{10}$ aryl. In embodiments, $Ar^1$ is independently substituted $C_9$-$C_{10}$ aryl. In embodiments, $Ar^1$ is independently substituted $C_5$ or $C_6$ aryl. In embodiments, $Ar^1$ is unsubstituted phenyl. In embodiments, $Ar^1$ is substituted or unsubstituted biphenyl. In embodiments, $Ar^1$ is substituted biphenyl. In embodiments, $Ar^1$ is unsubstituted biphenyl. In embodiments, $Ar^1$ is substituted or unsubstituted naphthyl. In embodiments, $Ar^1$ is substituted naphthyl. In embodiments, $Ar^1$ is unsubstituted naphthyl.

In embodiments, $Ar^1$ is substituted or unsubstituted 5 to 10 membered heterocycloalkyl. In embodiments, $Ar^1$ is substituted or unsubstituted 6 to 10 membered heterocycloalkyl. In embodiments, $Ar^1$ is substituted or unsubstituted 7 to 10 membered heterocycloalkyl. In embodiments, $Ar^1$ is substituted or unsubstituted 8 to 10 membered heterocycloalkyl. In embodiments, $Ar^1$ is substituted or unsubstituted 9 to 10 membered heterocycloalkyl. In embodiments, $Ar^1$ is substituted or unsubstituted 5 membered heterocycloalkyl. In embodiments, $Ar^1$ is substituted or unsubstituted 6 membered heterocycloalkyl. In embodiments, $Ar^1$ is unsubstituted 6 membered heterocycloalkyl. In embodiments, $Ar^1$ is unsubstituted 5 membered heterocycloalkyl. In embodiments, $Ar^1$ is substituted 6 membered heterocycloalkyl. In embodiments, $Ar^1$ is substituted 5 membered heterocycloalkyl. In embodiments, $Ar^1$ is substituted or unsubstituted 7 membered heterocycloalkyl. In embodiments, $Ar^1$ is substituted or unsubstituted 8 membered heterocycloalkyl. In embodiments, $Ar^1$ is unsubstituted 8 membered heterocycloalkyl. In embodiments, $Ar^1$ is unsubstituted 7 membered heterocycloalkyl. In embodiments, $Ar^1$ is substituted 8 membered heterocycloalkyl. In embodiments, $Ar^1$ is substituted 7 membered heterocycloalkyl. In embodiments, $Ar^1$ is substituted or unsubstituted 9 membered heterocycloalkyl. In embodiments, $Ar^1$ is substituted or unsubstituted 10 membered heterocycloalkyl. In embodiments, $Ar^1$ is unsubstituted 10 membered heterocycloalkyl. In embodiments, $Ar^1$ is unsubstituted 9 membered heterocycloalkyl. In embodiments, $Ar^1$ is substituted 10 membered heterocycloalkyl. In embodiments, $Ar^1$ is substituted 9 membered heterocycloalkyl.

In embodiments, $Ar^1$ is substituted or unsubstituted 5 to 10 membered heteroaryl. In embodiments, $Ar^1$ is substituted or unsubstituted 6 to 10 membered heteroaryl. In embodiments, $Ar^1$ is substituted or unsubstituted 7 to 10 membered heteroaryl. In embodiments, $Ar^1$ is substituted or unsubstituted 8 to 10 membered heteroaryl. In embodiments, $Ar^1$ is substituted or unsubstituted 9 to 10 membered heteroaryl. In embodiments, $Ar^1$ is substituted or unsubstituted 5 membered heteroaryl. In embodiments, $Ar^1$ is substituted or unsubstituted 6 membered heteroaryl. In embodiments, $Ar^1$ is unsubstituted 6 membered heteroaryl. In embodiments, $Ar^1$ is unsubstituted 5 membered heteroaryl. In embodiments, $Ar^1$ is substituted 6 membered heteroaryl. In embodiments, $Ar^1$ is substituted 5 membered heteroaryl. In embodiments, $Ar^1$ is substituted or unsubstituted 7 membered heteroaryl. In embodiments, $Ar^1$ is substituted or unsubstituted 8 membered heteroaryl. In embodiments, $Ar^1$ is unsubstituted 8 membered heteroaryl. In embodiments, $Ar^1$ is unsubstituted 7 membered heteroaryl. In embodiments, $Ar^1$ is substituted 8 membered heteroaryl. In embodiments, $Ar^1$ is substituted 7 membered heteroaryl. In embodiments, $Ar^1$ is substituted or unsubstituted 9 membered heteroaryl. In embodiments, $Ar^1$ is substituted or unsubstituted 10 membered heteroaryl. In embodiments, $Ar^1$ is unsubstituted 10 membered heteroaryl. In embodiments, $Ar^1$ is unsubstituted 9 membered heteroaryl. In embodiments, $Ar^1$ is substituted 10 membered heteroaryl. In embodiments, $Ar^1$ is substituted 9 membered heteroaryl.

In embodiments, $Ar^1$ is substituted fused (e.g., $C_5$-$C_{10}$) ring aryl. In embodiments, $Ar^1$ is unsubstituted fused (e.g., $C_5$-$C_{10}$) ring aryl. In embodiments, $Ar^1$ is substituted fused (e.g., 5-10 membered) ring heteroaryl. In embodiments, $Ar^1$ is unsubstituted fused (e.g., 5-10 membered) ring heteroaryl. In embodiments, $Ar^1$ is substituted or unsubstituted pyridyl. In embodiments, $Ar^1$ is substituted or unsubstituted furanyl. In embodiments, $Ar^1$ is substituted or unsubstituted thienyl. In embodiments, $Ar^1$ is substituted or unsubstituted indolyl. In embodiments, $Ar^1$ is substituted or unsubstituted quinolinyl. In embodiments, $Ar^1$ is substituted or unsubstituted isoquinolinyl. In embodiments, $Ar^1$ is substituted or unsubstituted thiazolyl. In embodiments, $Ar^1$ is substituted or unsubstituted pyrimidyl. In embodiments, $Ar^1$ is substituted or unsubstituted quinoxalinyl.

In embodiments, $Ar^1$ is substituted (e.g., substituted with a substituent group, a size-limited substituent group, or lower substituent group) or unsubstituted $C_4$-$C_{10}$ cycloalkyl. In embodiments, $Ar^1$ is substituted (e.g., substituted with a substituent group, a size-limited substituent group, or lower substituent group) or unsubstituted $C_6$-$C_{10}$ cycloalkyl. In embodiments, $Ar^1$ is substituted (e.g., substituted with a substituent group, a size-limited substituent group, or lower substituent group) or unsubstituted $C_7$-$C_{10}$ cycloalkyl. In embodiments, $Ar^1$ is substituted (e.g., substituted with a substituent group, a size-limited substituent group, or lower substituent group) or unsubstituted $C_8$-$C_{10}$ cycloalkyl. In embodiments, $Ar^1$ is substituted (e.g., substituted with a substituent group, a size-limited substituent group, or lower substituent group) or unsubstituted $C_9$-$C_{10}$ cycloalkyl. In embodiments, $Ar^1$ is unsubstituted $C_5$-$C_{10}$ cycloalkyl. In embodiments, $Ar^1$ is unsubstituted $C_6$-$C_{10}$ cycloalkyl. In embodiments, $Ar^1$ is unsubstituted $C_7$-$C_{10}$ cycloalkyl. In embodiments, $Ar^1$ is unsubstituted $C_8$-$C_{10}$ cycloalkyl. In embodiments, $Ar^1$ is unsubstituted $C_9$-$C_{10}$ cycloalkyl. In embodiments, $Ar^1$ is independently substituted (e.g., substituted with a substituent group, a size-limited substituent group, or lower substituent group) $C_5$-$C_{10}$ cycloalkyl. In embodiments, $Ar^1$ is independently substituted (e.g., substituted with a substituent group, a size-limited substituent group, or lower substituent group) $C_6$-$C_{10}$ cycloalkyl. In embodiments, $Ar^1$ is independently substituted (e.g., substituted with a substituent group, a size-limited substituent group, or lower substituent group) $C_7$-$C_{10}$ cycloalkyl. In embodiments, $Ar^1$ is independently substituted (e.g., substituted with a substituent group, a size-limited substituent group, or lower substituent group) $C_8$-$C_{10}$ cycloalkyl. In embodiments, $Ar^1$ is independently substituted (e.g., substituted with a substituent group, a size-limited substituent group, or lower substituent group) $C_9$-$C_{10}$ cycloalkyl. In embodiments, $Ar^1$ is independently substituted (e.g., substituted with a substituent group, a size-limited substituent group, or lower substituent group) $C_5$ or $C_6$ cycloalkyl.

In embodiments, $Ar^1$ is substituted (e.g., substituted with a substituent group, a size-limited substituent group, or lower substituent group) or unsubstituted $C_5$-$C_{10}$ aryl. In embodiments, $Ar^1$ is substituted (e.g., substituted with a substituent group, a size-limited substituent group, or lower substituent group) or unsubstituted $C_6$-$C_{10}$ aryl. In embodiments, $Ar^1$ is substituted (e.g., substituted with a substituent group, a size-limited substituent group, or lower substituent group) or unsubstituted $C_7$-$C_{10}$ aryl. In embodiments, $Ar^1$ is substituted (e.g., substituted with a substituent group, a size-limited substituent group, or lower substituent group) or unsubstituted $C_8$-$C_{10}$ aryl. In embodiments, $Ar^1$ is substituted (e.g., substituted with a substituent group, a size-limited substituent group, or lower substituent group) or unsubstituted $C_9$-$C_{10}$ aryl. In embodiments, $Ar^1$ is unsubstituted $C_5$-$C_{10}$ aryl. In embodiments, $Ar^1$ is unsubstituted $C_6$-$C_{10}$ aryl. In embodiments, $Ar^1$ is unsubstituted $C_7$-$C_{10}$ aryl. In embodiments, $Ar^1$ is unsubstituted $C_8$-$C_{10}$ aryl. In embodiments, $Ar^1$ is unsubstituted $C_9$-$C_{10}$ aryl. In embodiments, $Ar^1$ is independently substituted (e.g., substituted with a substituent group, a size-limited substituent group, or lower substituent group) phenyl. In embodiments, $Ar^1$ is independently substituted (e.g., substituted with a substituent group, a size-limited substituent group, or lower substituent group) $C_5$-$C_{10}$ aryl. In embodiments, $Ar^1$ is independently substituted (e.g., substituted with a substituent group, a size-limited substituent group, or lower substituent group) $C_6$-$C_{10}$ aryl. In embodiments, $Ar^1$ is independently substituted (e.g., substituted with a substituent group, a size-limited substituent group, or lower substituent group) $C_7$-$C_{10}$ aryl. In embodiments, $Ar^1$ is independently substituted (e.g., substituted with a substituent group, a size-limited substituent group, or lower substituent group) $C_5$-$C_{10}$ aryl. In embodiments, $Ar^1$ is independently substituted (e.g., substituted with a substituent group, a size-limited substituent group, or lower substituent group) $C_9$-$C_{10}$ aryl. In embodiments, $Ar^1$ is independently substituted (e.g., substituted with a substituent group, a size-limited substituent group, or lower substituent group) $C_5$ or $C_6$ aryl. In embodiments, $Ar^1$ is unsubstituted phenyl. In embodiments, $Ar^1$ is substituted (e.g., substituted with a substituent group, a size-limited substituent group, or lower substituent group) or unsubstituted biphenyl. In embodiments, $Ar^1$ is substituted (e.g., substituted with a substituent group, a size-limited substituent group, or lower substituent group) biphenyl. In embodiments, $Ar^1$ is unsubstituted biphenyl. In embodiments, $Ar^1$ is substituted (e.g., substituted with a substituent group, a size-limited substituent group, or lower substituent group) or unsubstituted naphthyl. In embodiments, $Ar^1$ is substituted (e.g., substituted with a substituent group, a size-limited substituent group, or lower substituent group) naphthyl. In embodiments, $Ar^1$ is unsubstituted naphthyl.

In embodiments, $Ar^1$ is substituted (e.g., substituted with a substituent group, a size-limited substituent group, or lower substituent group) or unsubstituted 5 to 10 membered heterocycloalkyl. In embodiments, $Ar^1$ is substituted (e.g., substituted with a substituent group, a size-limited substituent group, or lower substituent group) or unsubstituted 6 to 10 membered heterocycloalkyl. In embodiments, $Ar^1$ is substituted (e.g., substituted with a substituent group, a size-limited substituent group, or lower substituent group) or unsubstituted 7 to 10 membered heterocycloalkyl. In embodiments, $Ar^1$ is substituted (e.g., substituted with a substituent group, a size-limited substituent group, or lower substituent group) or unsubstituted 8 to 10 membered heterocycloalkyl. In embodiments, $Ar^1$ is substituted (e.g., substituted with a substituent group, a size-limited substituent group, or lower substituent group) or unsubstituted 9 to 10 membered heterocycloalkyl. In embodiments, $Ar^1$ is substituted (e.g., substituted with a substituent group, a size-limited substituent group, or lower substituent group) or unsubstituted 5 membered heterocycloalkyl. In embodiments, $Ar^1$ is substituted (e.g., substituted with a substituent group, a size-limited substituent group, or lower substituent group) or unsubstituted 6 membered heterocycloalkyl. In embodiments, $Ar^1$ is unsubstituted 6 membered heterocycloalkyl. In embodiments, $Ar^1$ is unsubstituted 5 membered heterocycloalkyl. In embodiments, $Ar^1$ is substituted (e.g., substituted with a substituent group, a size-limited substituent group, or lower substituent group) 6 membered heterocycloalkyl. In embodiments, $Ar^1$ is substituted (e.g., substituted with a substituent group, a size-limited substituent group, or lower substituent group) 5 membered heterocycloalkyl. In embodiments, $Ar^1$ is substituted (e.g., substituted with a substituent group, a size-limited substituent group, or lower substituent group) or unsubstituted 7 membered heterocycloalkyl. In embodiments, $Ar^1$ is substituted (e.g., substituted with a substituent group, a size-limited substituent group, or lower substituent group) or unsubstituted 8 membered heterocycloalkyl. In embodiments, $Ar^1$ is unsubstituted 8 membered heterocycloalkyl. In embodiments, $Ar^1$ is unsubstituted 7 membered heterocycloalkyl. In embodiments, $Ar^1$ is substituted (e.g., substituted with a substituent group, a size-limited substituent group, or lower substituent group) 8 membered heterocycloalkyl. In embodiments, $Ar^1$ is substituted (e.g., substituted with a substituent group, a size-limited substituent group, or lower substituent group) 7 membered heterocycloalkyl. In embodiments, $Ar^1$ is substituted (e.g., substituted with a substituent group, a size-limited substituent group, or lower substituent group) or unsubstituted 9 membered heterocycloalkyl. In embodiments, $Ar^1$ is substituted (e.g., substituted with a substituent group, a size-limited substituent group, or lower substituent group) or unsubstituted 10 membered heterocycloalkyl. In embodiments, $Ar^1$ is unsubstituted 10 membered heterocycloalkyl. In embodiments, $Ar^1$ is unsubstituted 9 membered heterocycloalkyl. In embodiments, $Ar^1$ is substituted (e.g., substituted with a substituent group, a size-limited substituent group, or lower substituent group) 10 membered heterocycloalkyl. In embodiments, $Ar^1$ is substituted (e.g., substituted with a substituent group, a size-limited substituent group, or lower substituent group) 9 membered heterocycloalkyl.

In embodiments, $Ar^1$ is substituted (e.g., substituted with a substituent group, a size-limited substituent group, or lower substituent group) or unsubstituted 5 to 10 membered heteroaryl. In embodiments, $Ar^1$ is substituted (e.g., substituted with a substituent group, a size-limited substituent group, or lower substituent group) or unsubstituted 6 to 10 membered heteroaryl. In embodiments, $Ar^1$ is substituted (e.g., substituted with a substituent group, a size-limited substituent group, or lower substituent group) or unsubstituted 7 to 10 membered heteroaryl. In embodiments, $Ar^1$ is substituted (e.g., substituted with a substituent group, a size-limited substituent group, or lower substituent group) or unsubstituted 8 to 10 membered heteroaryl. In embodiments, $Ar^1$ is substituted (e.g., substituted with a substituent group, a size-limited substituent group, or lower substituent group) or unsubstituted 9 to 10 membered heteroaryl. In embodiments, $Ar^1$ is substituted (e.g., substituted with a substituent group, a size-limited substituent group, or lower substituent group) or unsubstituted 5 membered heteroaryl. In embodiments, $Ar^1$ is substituted (e.g., substituted with a substituent group, a size-limited substituent group, or lower substituent group) or unsubstituted 6 membered heteroaryl. In embodiments, $Ar^1$ is unsubstituted 6 membered heteroaryl. In embodiments, $Ar^1$ is unsubstituted 5 membered heteroaryl. In embodiments, $Ar^1$ is substituted (e.g., substituted with a substituent group, a size-limited substituent group, or lower substituent group) 6 membered heteroaryl. In embodiments, $Ar^1$ is substituted (e.g., substituted with a substituent group, a size-limited substituent group, or lower substituent group) 5 membered heteroaryl. In embodiments, $Ar^1$ is substituted (e.g., substituted with a substituent group, a size-limited substituent group, or lower substituent group) or unsubstituted 7 membered heteroaryl. In embodiments, $Ar^1$ is substituted (e.g., substituted with a substituent group, a size-limited substituent group, or lower substituent group) or unsubstituted 8 membered heteroaryl. In embodiments, $Ar^1$ is unsubstituted 8 membered heteroaryl. In embodiments, $Ar^1$ is unsubstituted 7 membered heteroaryl. In embodiments, $Ar^1$ is substituted (e.g., substituted with a substituent group, a size-limited substituent group, or lower substituent group) 8 membered heteroaryl. In embodiments, $Ar^1$ is substituted (e.g., substituted with a substituent group, a size-limited substituent group, or lower substituent group) 7 membered heteroaryl. In embodiments, $Ar^1$ is substituted (e.g., substituted with a substituent group, a size-limited substituent group, or lower substituent group) or unsubstituted 9 membered heteroaryl. In embodiments, $Ar^1$ is substituted (e.g., substituted with a substituent group, a size-limited substituent group, or lower substituent group) or unsubstituted 10 membered heteroaryl. In embodiments, $Ar^1$ is unsubstituted 10 membered heteroaryl. In embodiments, $Ar^1$ is unsubstituted 9 membered heteroaryl. In embodiments, $Ar^1$ is substituted (e.g., substituted with a substituent group, a size-limited substituent group, or lower substituent group) 10 membered heteroaryl. In embodiments, $Ar^1$ is substituted (e.g., substituted with a substituent group, a size-limited substituent group, or lower substituent group) 9 membered heteroaryl.

In embodiments, $Ar^1$ is substituted (e.g., substituted with a substituent group, a size-limited substituent group, or lower substituent group) fused (e.g., $C_5$-$C_{10}$) ring aryl. In embodiments, $Ar^1$ is unsubstituted fused (e.g., $C_5$-$C_{10}$) ring aryl. In embodiments, $Ar^1$ is substituted (e.g., substituted with a substituent group, a size-limited substituent group, or lower substituent group) fused (e.g., 5-10 membered) ring heteroaryl. In embodiments, $Ar^1$ is unsubstituted fused (e.g., 5-10 membered) ring heteroaryl. In embodiments, $Ar^1$ is substituted (e.g., substituted with a substituent group, a size-limited substituent group, or lower substituent group) or unsubstituted pyridyl. In embodiments, $Ar^1$ is substituted (e.g., substituted with a substituent group, a size-limited substituent group, or lower substituent group) or unsubstituted furanyl. In embodiments, $Ar^1$ is substituted (e.g., substituted with a substituent group, a size-limited substituent group, or lower substituent group) or unsubstituted thienyl. In embodiments, $Ar^1$ is substituted (e.g., substituted with a substituent group, a size-limited substituent group, or lower substituent group) or unsubstituted indolyl. In embodiments, $Ar^1$ is substituted (e.g., substituted with a substituent group, a size-limited substituent group, or lower substituent group) or unsubstituted quinolinyl. In embodiments, $Ar^1$ is substituted (e.g., substituted with a substituent group, a size-limited substituent group, or lower substituent group) or unsubstituted isoquinolinyl. In embodiments, $Ar^1$ is substituted (e.g., substituted with a substituent group, a size-limited substituent group, or lower substituent group) or unsubstituted thiazolyl. In embodiments, $Ar^1$ is substituted (e.g., substituted with a substituent group, a size-limited substituent group, or lower substituent group) or unsubstituted pyrimidyl. In embodiments, $Ar^1$ is substituted (e.g., substituted with a substituent group, a size-limited substituent group, or lower substituent group) or unsubstituted quinoxalinyl.

In embodiments, $Ar^2$ is substituted or unsubstituted $C_5$-$C_{10}$ cycloalkylene. In embodiments, $Ar^2$ is substituted or unsubstituted $C_6$-$C_{10}$ cycloalkylene. In embodiments, $Ar^2$ is substituted or unsubstituted $C_7$-$C_{10}$ cycloalkylene. In embodiments, $Ar^2$ is substituted or unsubstituted $C_5$-$C_{10}$ cycloalkylene. In embodiments, $Ar^2$ is substituted or unsubstituted $C_9$-$C_{10}$ cycloalkylene. In embodiments, $Ar^2$ is unsubstituted $C_5$-$C_{10}$ cycloalkylene. In embodiments, $Ar^2$ is unsubstituted $C_6$-$C_{10}$ cycloalkylene. In embodiments, $Ar^2$ is unsubstituted $C_7$-$C_{10}$ cycloalkylene. In embodiments, $Ar^2$ is unsubstituted $C_8$-$C_{10}$ cycloalkylene. In embodiments, $Ar^2$ is unsubstituted $C_9$-$C_{10}$ cycloalkylene. In embodiments, $Ar^2$ is unsubstituted $C_5$ or $C_6$ cycloalkylene. In embodiments, $Ar^2$ is substituted $C_5$-$C_{10}$ cycloalkylene. In embodiments, $Ar^2$ is substituted $C_6$-$C_{10}$ cycloalkylene. In embodiments, $Ar^2$ is substituted $C_7$-$C_{10}$ cycloalkylene. In embodiments, $Ar^2$ is substituted $C_8$-$C_{10}$ cycloalkylene. In embodiments, $Ar^2$ is substituted $C_9$-$C_{10}$ cycloalkylene. In embodiments, $Ar^2$ is substituted $C_5$ or $C_6$ cycloalkylene.

In embodiments, $Ar^2$ is substituted or unsubstituted $C_5$-$C_{10}$ arylene. In embodiments, $Ar^2$ is substituted or unsubstituted $C_6$-$C_{10}$ arylene. In embodiments, $Ar^2$ is substituted or unsubstituted $C_7$-$C_{10}$ arylene. In embodiments, $Ar^2$ is substituted or unsubstituted $C_8$-$C_{10}$ arylene. In embodiments, $Ar^2$ is substituted or unsubstituted $C_9$-$C_{10}$ arylene. In embodiments, $Ar^2$ is unsubstituted $C_5$-$C_{10}$ arylene. In embodiments, $Ar^2$ is unsubstituted $C_6$-$C_{10}$ arylene. In embodiments, $Ar^2$ is unsubstituted $C_7$-$C_{10}$ arylene. In embodiments, $Ar^2$ is unsubstituted $C_8$-$C_{10}$ arylene. In embodiments, $Ar^2$ is unsubstituted $C_9$-$C_{10}$ arylene. In embodiments, $Ar^2$ is unsubstituted $C_5$ or $C_6$ arylene. In embodiments, $Ar^2$ is independently substituted phenylene. In embodiments, $Ar^2$ is substituted $C_5$-$C_{10}$ arylene. In embodiments, $Ar^2$ is substituted $C_6$-$C_{10}$ arylene. In embodiments, $Ar^2$ is substituted $C_7$-$C_{10}$ arylene. In embodiments, $Ar^2$ is substituted $C_8$-$C_{10}$ arylene. In embodiments, $Ar^2$ is substituted $C_9$-$C_{10}$ arylene. In embodiments, $Ar^2$ is substituted $C_5$ or $C_6$ arylene. In embodiments, $Ar^2$ is unsubstituted phenylene. In embodiments, $Ar^2$ is substituted or unsubstituted biphenylene. In embodiments, $Ar^2$ is substituted biphenylene. In embodiments, $Ar^2$ is unsubstituted biphenylene. In embodiments, $Ar^2$ is substituted or unsubstituted naphthylene. In embodiments, $Ar^2$ is substituted naphthylene. In embodiments, $Ar^2$ is unsubstituted naphthylene.

In embodiments, $Ar^2$ is substituted or unsubstituted 5 to 10 membered heterocycloalkylene. In embodiments, $Ar^2$ is substituted or unsubstituted 6 to 10 membered heterocycloalkylene. In embodiments, $Ar^2$ is substituted or unsubstituted 7 to 10 membered heterocycloalkylene. In embodiments, $Ar^2$ is substituted or unsubstituted 8 to 10 membered heterocycloalkylene. In embodiments, $Ar^2$ is substituted or unsubstituted 9 to 10 membered heterocycloalkylene. In embodiments, $Ar^2$ is substituted or unsubstituted 5 membered heterocycloalkylene. In embodiments, $Ar^2$ is substituted or unsubstituted 6 membered heterocycloalkylene. In embodiments, $Ar^2$ is unsubstituted 6 membered heterocycloalkylene. In embodiments, $Ar^2$ is unsubstituted 5 membered heterocycloalkylene. In embodiments, $Ar^2$ is substituted 6 membered heterocycloalkylene. In embodiments, $Ar^2$ is substituted 5 membered heterocycloalkylene. In embodiments, $Ar^2$ is substituted or unsubstituted 7 membered heterocycloalkylene. In embodiments, $Ar^2$ is substituted or unsubstituted 8 membered heterocycloalkylene. In embodiments, $Ar^2$ is unsubstituted 8 membered heterocycloalkylene. In embodiments, $Ar^2$ is unsubstituted 7 membered heterocycloalkylene. In embodiments, $Ar^2$ is substituted 8 membered heterocycloalkylene. In embodiments, $Ar^2$ is substituted 7 membered heterocycloalkylene. In embodiments, $Ar^2$ is substituted or unsubstituted 9 membered heterocycloalkylene. In embodiments, $Ar^2$ is substituted or unsubstituted 10 membered heterocycloalkylene. In embodiments, $Ar^2$ is unsubstituted 10 membered heterocycloalkylene. In embodiments, $Ar^2$ is unsubstituted 9 membered heterocycloalkylene. In embodiments, $Ar^2$ is substituted 10 membered heterocycloalkylene. In embodiments, $Ar^2$ is substituted 9 membered heterocycloalkylene.

In embodiments, $Ar^2$ is substituted or unsubstituted 5 to 10 membered heteroarylene. In embodiments, $Ar^2$ is substituted or unsubstituted 6 to 10 membered heteroarylene. In embodiments, $Ar^2$ is substituted or unsubstituted 7 to 10 membered heteroarylene. In embodiments, $Ar^2$ is substituted or unsubstituted 8 to 10 membered heteroarylene. In embodiments, $Ar^2$ is substituted or unsubstituted 9 to 10 membered heteroarylene. In embodiments, $Ar^2$ is substituted or unsubstituted 5 membered heteroarylene. In embodiments, $Ar^2$ is substituted or unsubstituted 6 membered heteroarylene. In embodiments, $Ar^2$ is unsubstituted 6 membered heteroarylene. In embodiments, $Ar^2$ is unsubstituted 5 membered heteroarylene. In embodiments, $Ar^2$ is substituted 6 membered heteroarylene. In embodiments, $Ar^2$ is substituted 5 membered heteroarylene. In embodiments, $Ar^2$ is substituted or unsubstituted 7 membered heteroarylene. In embodiments, $Ar^2$ is substituted or unsubstituted 8 membered heteroarylene. In embodiments, $Ar^2$ is unsubstituted 8 membered heteroarylene. In embodiments, $Ar^2$ is unsubstituted 7 membered heteroarylene. In embodiments, $Ar^2$ is substituted 8 membered heteroarylene. In embodiments, $Ar^2$ is substituted 7 membered heteroarylene. In embodiments, $Ar^2$ is substituted or unsubstituted 9 membered heteroarylene. In embodiments, $Ar^2$ is substituted or unsubstituted 10 membered heteroarylene. In embodiments, $Ar^2$ is unsubstituted 10 membered heteroarylene. In embodiments, $Ar^2$ is unsubstituted 9 membered heteroarylene. In embodiments, $Ar^2$ is substituted 10 membered heteroarylene. In embodiments, $Ar^2$ is substituted 9 membered heteroarylene.

In embodiments, $Ar^2$ is substituted fused (e.g., $C_5$-$C_{10}$) ring arylene. In embodiments, $Ar^2$ is unsubstituted fused (e.g., $C_5$-$C_{10}$) ring arylene. In embodiments, $Ar^2$ is substituted fused (e.g., 5-10 membered) ring heteroarylene. In embodiments, $Ar^2$ is unsubstituted fused (e.g., 5-10 membered) ring heteroarylene. In embodiments, $Ar^2$ is substituted or unsubstituted pyridylene. In embodiments, $Ar^2$ is substituted or unsubstituted furanylene. In embodiments, $Ar^2$ is substituted or unsubstituted thienylene. In embodiments, $Ar^2$ is substituted or unsubstituted indolylene. In embodiments, $Ar^2$ is substituted or unsubstituted quinolinylene. In embodiments, $Ar^2$ is substituted or unsubstituted isoquinolinylene. In embodiments, $Ar^2$ is substituted or unsubstituted thiazolylene. In embodiments, $Ar^2$ is substituted or unsubstituted pyrimidylene. In embodiments, $Ar^2$ is substituted or unsubstituted quinoxalinylene.

In embodiments, $Ar^2$ is substituted (e.g., substituted with a substituent group, a size-limited substituent group, or lower substituent group) or unsubstituted $C_5$-$C_{10}$ cycloalkylene. In embodiments, $Ar^2$ is substituted (e.g., substituted with a substituent group, a size-limited substituent group, or lower substituent group) or unsubstituted $C_6$-$C_{10}$ cycloalkylene. In embodiments, $Ar^2$ is substituted (e.g., substituted with a substituent group, a size-limited substituent group, or lower substituent group) or unsubstituted $C_7$-$C_{10}$ cycloalkylene. In embodiments, $Ar^2$ is substituted (e.g., substituted with a substituent group, a size-limited substituent group, or lower substituent group) or unsubstituted $C_8$-$C_{10}$ cycloalkylene. In embodiments, $Ar^2$ is substituted (e.g., substituted with a substituent group, a size-limited substituent group, or lower substituent group) or unsubstituted $C_9$-$C_{10}$ cycloalkylene. In embodiments, $Ar^2$ is unsubstituted $C_5$-$C_{10}$ cycloalkylene. In embodiments, $Ar^2$ is unsubstituted $C_6$-$C_{10}$ cycloalkylene. In embodiments, $Ar^2$ is unsubstituted $C_7$-$C_{10}$ cycloalkylene. In embodiments, $Ar^2$ is unsubstituted $C_8$-$C_{10}$ cycloalkylene. In embodiments, $Ar^2$ is unsubstituted $C_9$-$C_{10}$ cycloalkylene. In embodiments, $Ar^2$ is unsubstituted $C_5$ or $C_6$ cycloalkylene. In embodiments, $Ar^2$ is substituted (e.g., substituted with a substituent group, a size-limited substituent group, or lower substituent group) $C_5$-$C_{10}$ cycloalkylene. In embodiments, $Ar^2$ is substituted (e.g., substituted with a substituent group, a size-limited substituent group, or lower substituent group) $C_6$-$C_{10}$ cycloalkylene. In embodiments, $Ar^2$ is substituted (e.g., substituted with a substituent group, a size-limited substituent group, or lower substituent group) $C_7$-$C_{10}$ cycloalkylene. In embodiments, $Ar^2$ is substituted (e.g., substituted with a substituent group, a size-limited substituent group, or lower substituent group) $C_8$-$C_{10}$ cycloalkylene. In embodiments, $Ar^2$ is substituted (e.g., substituted with a substituent group, a size-limited substituent group, or lower substituent group) $C_9$-$C_{10}$ cycloalkylene. In embodiments, $Ar^2$ is substituted (e.g., substituted with a substituent group, a size-limited substituent group, or lower substituent group) $C_5$ or $C_6$ cycloalkylene.

In embodiments, $Ar^2$ is substituted (e.g., substituted with a substituent group, a size-limited substituent group, or lower substituent group) or unsubstituted $C_5$-$C_{10}$ arylene. In embodiments, $Ar^2$ is substituted (e.g., substituted with a substituent group, a size-limited substituent group, or lower substituent group) or unsubstituted $C_6$-$C_{10}$ arylene. In embodiments, $Ar^2$ is substituted (e.g., substituted with a substituent group, a size-limited substituent group, or lower substituent group) or unsubstituted $C_7$-$C_{10}$ arylene. In embodiments, $Ar^2$ is substituted (e.g., substituted with a substituent group, a size-limited substituent group, or lower substituent group) or unsubstituted $C_8$-$C_{10}$ arylene. In embodiments, $Ar^2$ is substituted (e.g., substituted with a substituent group, a size-limited substituent group, or lower substituent group) or unsubstituted $C_9$-$C_{10}$ arylene. In embodiments, $Ar^2$ is unsubstituted $C_5$-$C_{10}$ arylene. In embodiments, $Ar^2$ is unsubstituted $C_6$-$C_{10}$ arylene. In embodiments, $Ar^2$ is unsubstituted $C_7$-$C_{10}$ arylene. In embodiments, $Ar^2$ is unsubstituted $C_8$-$C_{10}$ arylene. In embodiments, $Ar^2$ is unsubstituted $C_9$-$C_{10}$ arylene. In embodiments, $Ar^2$ is unsubstituted $C_5$ or $C_6$ arylene. In embodiments, $Ar^2$ is independently substituted (e.g., substituted with a substituent group, a size-limited substituent group, or lower substituent group) phenylene. In embodiments, $Ar^2$ is substituted (e.g., substituted with a substituent group, a size-limited substituent group, or lower substituent group) $C_5$-$C_{10}$ arylene. In embodiments, $Ar^2$ is substituted (e.g., substituted with a substituent group, a size-limited substituent group, or lower substituent group) $C_6$-$C_{10}$ arylene. In embodiments, $Ar^2$ is substituted (e.g., substituted with a substituent group, a size-limited substituent group, or lower substituent group) $C_7$-$C_{10}$ arylene. In embodiments, $Ar^2$ is substituted (e.g., substituted with a substituent group, a size-limited substituent group, or lower substituent group) $C_8$-$C_{10}$ arylene. In embodiments, $Ar^2$ is substituted (e.g., substituted with a substituent group, a size-limited substituent group, or lower substituent group) $C_9$-$C_{10}$ arylene. In embodiments, $Ar^2$ is substituted (e.g., substituted with a substituent group, a size-limited substituent group, or lower substituent group) $C_5$ or $C_6$ arylene. In embodiments, $Ar^2$ is unsubstituted phenylene. In embodiments, $Ar^2$ is substituted (e.g., substituted with a substituent group, a size-limited substituent group, or lower substituent group) or unsubstituted biphenylene. In embodiments, $Ar^2$ is substituted (e.g., substituted with a substituent group, a size-limited substituent group, or lower substituent group) biphenylene. In embodiments, $Ar^2$ is unsubstituted biphenylene. In embodiments, $Ar^2$ is substituted (e.g., substituted with a substituent group, a size-limited substituent group, or lower substituent group) or unsubstituted naphthylene. In embodiments, $Ar^2$ is substituted (e.g., substituted with a substituent group, a size-limited substituent group, or lower substituent group) naphthylene. In embodiments, $Ar^2$ is unsubstituted naphthylene.

In embodiments, $Ar^2$ is substituted (e.g., substituted with a substituent group, a size-limited substituent group, or lower substituent group) or unsubstituted 5 to 10 membered heterocycloalkylene. In embodiments, $Ar^2$ is substituted (e.g., substituted with a substituent group, a size-limited substituent group, or lower substituent group) or unsubstituted 6 to 10 membered heterocycloalkylene. In embodiments, $Ar^2$ is substituted (e.g., substituted with a substituent group, a size-limited substituent group, or lower substituent group) or unsubstituted 7 to 10 membered heterocycloalkylene. In embodiments, $Ar^2$ is substituted (e.g., substituted with a substituent group, a size-limited substituent group, or lower substituent group) or unsubstituted 8 to 10 membered heterocycloalkylene. In embodiments, $Ar^2$ is substituted (e.g., substituted with a substituent group, a size-limited substituent group, or lower substituent group) or unsubstituted 9 to 10 membered heterocycloalkylene. In embodiments, $Ar^2$ is substituted (e.g., substituted with a substituent group, a size-limited substituent group, or lower substituent group) or unsubstituted 5 membered heterocycloalkylene. In embodiments, $Ar^2$ is substituted (e.g., substituted with a substituent group, a size-limited substituent group, or lower substituent group) or unsubstituted 6 membered heterocycloalkylene. In embodiments, $Ar^2$ is unsubstituted 6 membered heterocycloalkylene. In embodiments, $Ar^2$ is unsubstituted 5 membered heterocycloalkylene. In embodiments, $Ar^2$ is substituted (e.g., substituted with a substituent group, a size-limited substituent group, or lower substituent group) 6 membered heterocycloalkylene. In embodiments, $Ar^2$ is substituted (e.g., substituted with a substituent group, a size-limited substituent group, or lower substituent group) 5 membered heterocycloalkylene. In embodiments, $Ar^2$ is substituted (e.g., substituted with a substituent group, a size-limited substituent group, or lower substituent group) or unsubstituted 7 membered heterocycloalkylene. In embodiments, $Ar^2$ is substituted (e.g., substituted with a substituent group, a size-limited substituent group, or lower substituent group) or unsubstituted 8 membered heterocycloalkylene. In embodiments, $Ar^2$ is unsubstituted 8 membered heterocycloalkylene. In embodiments, $Ar^2$ is unsubstituted 7 membered heterocycloalkylene. In embodiments, $Ar^2$ is substituted (e.g., substituted with a substituent group, a size-limited substituent group, or lower substituent group) 8 membered heterocycloalkylene. In embodiments, $Ar^2$ is substituted (e.g., substituted with a substituent group, a size-limited substituent group, or lower substituent group) 7 membered heterocycloalkylene. In embodiments, $Ar^2$ is substituted (e.g., substituted with a substituent group, a size-limited substituent group, or lower substituent group) or unsubstituted 9 membered heterocycloalkylene. In embodiments, $Ar^2$ is substituted (e.g., substituted with a substituent group, a size-limited substituent group, or lower substituent group) or unsubstituted 10 membered heterocycloalkylene. In embodiments, $Ar^2$ is unsubstituted 10 membered heterocycloalkylene. In embodiments, $Ar^2$ is unsubstituted 9 membered heterocycloalkylene. In embodiments, $Ar^2$ is substituted (e.g., substituted with a substituent group, a size-limited substituent group, or lower substituent group) 10 membered heterocycloalkylene. In embodiments, $Ar^2$ is substituted (e.g., substituted with a substituent group, a size-limited substituent group, or lower substituent group) 9 membered heterocycloalkylene.

In embodiments, $Ar^2$ is substituted (e.g., substituted with a substituent group, a size-limited substituent group, or lower substituent group) or unsubstituted 5 to 10 membered heteroarylene. In embodiments, $Ar^2$ is substituted (e.g., substituted with a substituent group, a size-limited substituent group, or lower substituent group) or unsubstituted 6 to 10 membered heteroarylene. In embodiments, $Ar^2$ is substituted (e.g., substituted with a substituent group, a size-limited substituent group, or lower substituent group) or unsubstituted 7 to 10 membered heteroarylene. In embodiments, $Ar^2$ is substituted (e.g., substituted with a substituent group, a size-limited substituent group, or lower substituent group) or unsubstituted 8 to 10 membered heteroarylene. In embodiments, $Ar^2$ is substituted (e.g., substituted with a substituent group, a size-limited substituent group, or lower substituent group) or unsubstituted 9 to 10 membered heteroarylene. In embodiments, $Ar^2$ is substituted (e.g., substituted with a substituent group, a size-limited substituent group, or lower substituent group) or unsubstituted 5 membered heteroarylene. In embodiments, $Ar^2$ is substituted (e.g., substituted with a substituent group, a size-limited substituent group, or lower substituent group) or unsubstituted 6 membered heteroarylene. In embodiments, $Ar^2$ is unsubstituted 6 membered heteroarylene. In embodiments, $Ar^2$ is unsubstituted 5 membered heteroarylene. In embodiments, $Ar^2$ is substituted (e.g., substituted with a substituent group, a size-limited substituent group, or lower substituent group) 6 membered heteroarylene. In embodiments, $Ar^2$ is substituted (e.g., substituted with a substituent group, a size-limited substituent group, or lower substituent group) 5 membered heteroarylene. In embodiments, $Ar^2$ is substituted (e.g., substituted with a substituent group, a size-limited substituent group, or lower substituent group) or unsubstituted 7 membered heteroarylene. In embodiments, $Ar^2$ is substituted (e.g., substituted with a substituent group, a size-limited substituent group, or lower substituent group) or unsubstituted 8 membered heteroarylene. In embodiments, $Ar^2$ is unsubstituted 8 membered heteroarylene. In embodiments, $Ar^2$ is unsubstituted 7 membered heteroarylene. In embodiments, $Ar^2$ is substituted (e.g., substituted with a substituent group, a size-limited substituent group, or lower substituent group) 8 membered heteroarylene. In embodiments, $Ar^2$ is substituted (e.g., substituted with a substituent group, a size-limited substituent group, or lower substituent group) 7 membered heteroarylene. In embodiments, $Ar^2$ is substituted (e.g., substituted with a substituent group, a size-limited substituent group, or lower substituent group) or unsubstituted 9 membered heteroarylene. In embodiments, $Ar^2$ is substituted (e.g., substituted with a substituent group, a size-limited substituent group, or lower substituent group) or unsubstituted 10 membered heteroarylene. In embodiments, $Ar^2$ is unsubstituted 10 membered heteroarylene. In embodiments, $Ar^2$ is unsubstituted 9 membered heteroarylene. In embodiments, $Ar^2$ is substituted (e.g., substituted with a substituent group, a size-limited substituent group, or lower substituent group) 10 membered heteroarylene. In embodiments, $Ar^2$ is substituted (e.g., substituted with a substituent group, a size-limited substituent group, or lower substituent group) 9 membered heteroarylene.

In embodiments, $Ar^2$ is substituted (e.g., substituted with a substituent group, a size-limited substituent group, or lower substituent group) fused (e.g., $C_5$-$C_{10}$) ring arylene. In embodiments, $Ar^2$ is unsubstituted fused (e.g., $C_5$-$C_{10}$) ring arylene. In embodiments, $Ar^2$ is substituted (e.g., substituted with a substituent group, a size-limited substituent group, or lower substituent group) fused (e.g., 5-10 membered) ring heteroarylene. In embodiments, $Ar^2$ is unsubstituted fused (e.g., 5-10 membered) ring heteroarylene. In embodiments, $Ar^2$ is substituted (e.g., substituted with a substituent group, a size-limited substituent group, or lower substituent group) or unsubstituted pyridylene. In embodiments, $Ar^2$ is substituted (e.g., substituted with a substituent group, a size-limited substituent group, or lower substituent group) or unsubstituted furanylene. In embodiments, $Ar^2$ is substituted (e.g., substituted with a substituent group, a size-limited substituent group, or lower substituent group) or unsubstituted thienylene. In embodiments, $Ar^2$ is substituted (e.g., substituted with a substituent group, a size-limited substituent group, or lower substituent group) or unsubstituted indolylene. In embodiments, $Ar^2$ is substituted (e.g., substituted with a substituent group, a size-limited substituent group, or lower substituent group) or unsubstituted quinolinylene. In embodiments, $Ar^2$ is substituted (e.g., substituted with a substituent group, a size-limited substituent group, or lower substituent group) or unsubstituted isoquinolinylene. In embodiments, $Ar^2$ is substituted (e.g., substituted with a substituent group, a size-limited substituent group, or lower substituent group) or unsubstituted thiazolylene. In embodiments, $Ar^2$ is substituted (e.g., substituted with a substituent group, a size-limited substituent group, or lower substituent group) or unsubstituted pyrimidylene. In embodiments, $Ar^2$ is substituted (e.g., substituted with a substituent group, a size-limited substituent group, or lower substituent group) or unsubstituted quinoxalinylene.

In embodiments, the cell-penetrating conjugate has the formula:

(II)

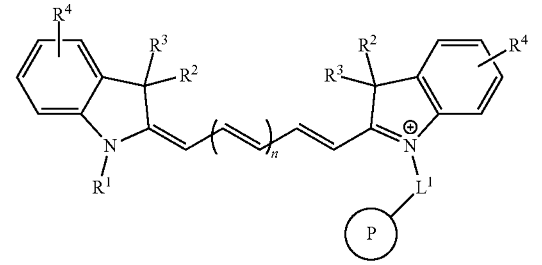

or (V)

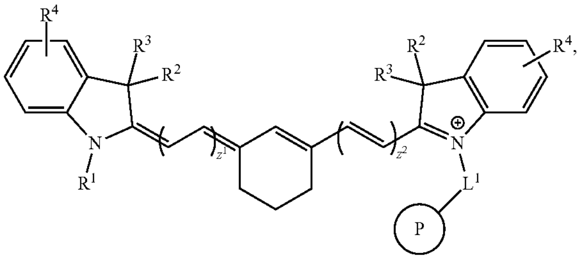

wherein $L^1$, n, P, $z^1$, and $z^2$ are as defined above and herein, including embodiments thereof. $R^1$, $R^2$, $R^3$ and $R^4$ are independently hydrogen, halogen, $—CX_3$, —CN, —C(O)OH, $—CH_2C(O)OH$, $—C(O)NH_2$, —OH, —SH, $—NO_2$, $—NH_2$, $—NHNH_2$, $—SO_3H$, $—ONH_2$, $—NHC{=}(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

In embodiments, the cell-penetrating conjugate has the formula:

(II)

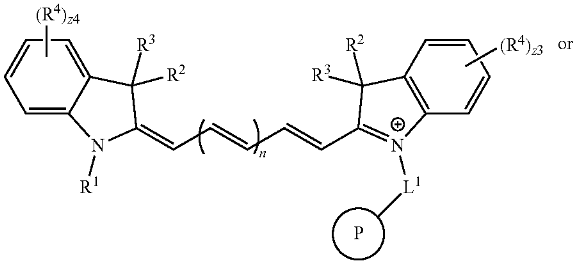

or (V)

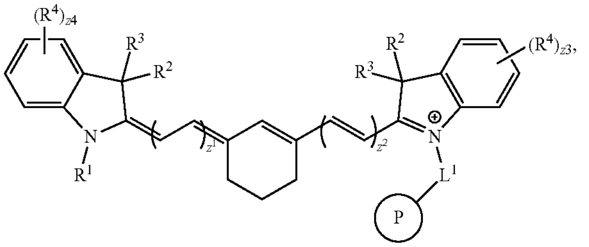

wherein $R^1$, $R^2$, $R^3$, $R^4$, $L^1$, n, P, $z^1$, and $z^2$ are as defined above and herein, including embodiments thereof. The symbols $z^3$ and $z^4$ are independently an integer from 0 to 4. In embodiments, $z^3$ is 0. In embodiments, $z^3$ is 1. In embodiments, $z^3$ is 2. In embodiments, $z^3$ is 3. In embodiments, $z^3$ is 4. In embodiments, $z^3$ is from 1 to 4. In embodiments, $z^4$ is 0. In embodiments, $z^4$ is 1. In embodiments, $z^4$ is 2. In embodiments, $z^4$ is 3. In embodiments, $z^4$ is 4. In embodiments, $z^4$ is from 1 to 4.

In embodiments, $R^1$, $R^2$, $R^3$ and $R^4$ are independently hydrogen, halogen, $—CX_3$, —CN, —C(O)OH, $—CH_2C(O)OH$, $—C(O)NH_2$, —OH, —SH, $—NO_2$, $—NH_2$, $—NHNH_2$, $—SO_3H$, $—ONH_2$, $—NHC{=}(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

In embodiments, the cell-penetrating conjugate has the formula:

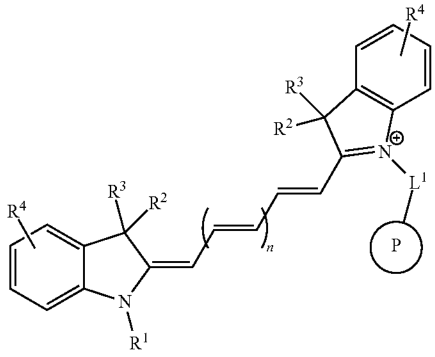

wherein $R^1$, $R^2$, $R^3$, $R^4$, $L^1$, n, P, $z^1$, and $z^2$ are as defined above and herein, including embodiments thereof. In formula (II), $R^1$, $R^2$, $R^3$ and $R^4$ are independently hydrogen, halogen, —$CX_3$, —CN, —C(O)OH, —$CH_2C(O)OH$, —$C(O)NH_2$, —OH, —SH, —$NO_2$, —$NH_2$, —$NHNH_2$, —$ONH_2$, —NHC═(O)$NHNH_2$, —$SO_3H$, substituted or unsubstituted (e.g., $C_1$-$C_{10}$) alkyl, substituted or unsubstituted (e.g., 1 to 6 membered) heteroalkyl, substituted or unsubstituted (e.g., $C_3$-$C_6$) cycloalkyl, substituted or unsubstituted (e.g., 3 to 6 membered) heterocycloalkyl, or substituted or unsubstituted (e.g., 5 to 6 membered) heteroaryl.

In embodiments, the cell-penetrating conjugate has the formula:

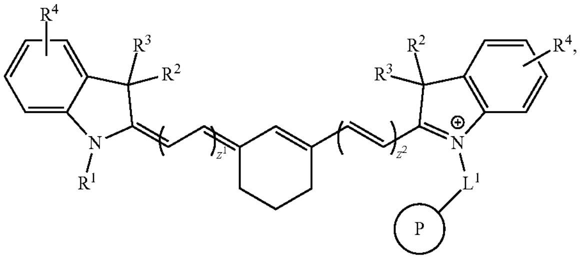

wherein $R^1$, $R^2$, $R^3$, $R^4$, $L^1$, n, P, $z^1$, and $z^2$ are as defined above and herein, including embodiments thereof.

Where the nitrogen is attached to a non-cell penetrating protein, such as an antibody, through $L^1$, a person of skill in the art will immediately understand that the nitrogen is formally positively charged. When the nitrogen is formally charged, it is understood that a counterion (e.g., anion) may be present. Any applicable anionic compound or molecule may be used as a counterion to the positively charged nitrogen, including for example chloride, bromide, sulfate, phosphate, nitrate, acetate, oxalate, citrate, carbonate, sulfide, or tartrate. In embodiments, the cell-penetrating conjugate further includes a counterion. A person of ordinary skill will immediately understand that the compounds provided herein may have a net charge (e.g. a net positive charge). In such cases, it is understood that any appropriate counterion may be present (e.g., chlorine). Additionally, the cell-penetrating conjugate provided herein may be present as a pharmaceutically acceptable salt. Thus, for example, where the compound overall or $R^1$, $R^2$, $R^3$, and $R^4$ contain a net charge (e.g., positive or negative), one of skill will immediately recognize that an appropriate counterion (e.g., cationic or anionic) will be present where the compound is in solution.

In embodiments, $R^1$, $R^2$, $R^3$ and $R^4$ are independently hydrogen or substituted or unsubstituted alkyl. In embodiments, $R^1$, $R^2$, $R^3$ and $R^4$ are independently hydrogen or methyl. In embodiments, $R^1$, $R^2$, and $R^3$ are independently methyl. In embodiments, $R^1$, $R^2$, and $R^3$ are independently unsubstituted methyl. In embodiments, $R^1$, $R^2$, $R^3$ and $R^4$ are independently hydrogen or substituted (e.g., substituted with a substituent group, a size-limited substituent group, or lower substituent group) or unsubstituted alkyl. In embodiments, $R^1$, $R^2$, $R^3$ and $R^4$ are independently hydrogen or methyl. In embodiments, $R^1$, $R^2$, and $R^3$ are independently methyl. In embodiments, $R^1$, $R^2$, and $R^3$ are independently unsubstituted methyl. In embodiments, $R^1$, $R^2$, $R^3$ and $R^4$ are independently hydrogen or methyl and $R^4$ is —$SO_3H$.

In embodiments, $R^1$ is independently hydrogen, halogen, —$CX_3$, —CN, —C(O)OH, —$CH_2C(O)OH$, —$C(O)NH_2$, —OH, —SH, —$NO_2$, —$NH_2$, —$NHNH_2$, —$ONH_2$, —NHC═(O)$NHNH_2$, or substituted or unsubstituted (e.g., $C_1$-$C_6$) alkyl. In embodiments, $R^1$ is independently halogen. In embodiments, $R^1$ is —$CX_3$. In embodiments, $R^1$ is —CN. In embodiments, $R^1$ is —C(O)OH. In embodiments, $R^1$ is —$CH_2C(O)OH$. In embodiments, $R^1$ is —$C(O)NH_2$. In embodiments, $R^1$ is —OH. In embodiments, $R^1$ is —SH. In embodiments, $R^1$ is —$NO_2$. In embodiments, $R^1$ is —$NH_2$. In embodiments, $R^1$ is —$NHNH_2$. In embodiments, $R^1$ is —$ONH_2$.

In embodiments, $R^1$ is independently hydrogen or substituted or unsubstituted (e.g., $C_1$-$C_4$) alkyl. In embodiments, $R^1$ is substituted $C_1$-$C_4$ alkyl. In embodiments, $R^1$ is unsubstituted $C_1$-$C_4$ alkyl. In embodiments, $R^1$ is substituted $C_2$-$C_4$ alkyl. In embodiments, $R^1$ is unsubstituted $C_2$-$C_4$ alkyl. In embodiments, $R^1$ is substituted $C_3$-$C_4$ alkyl. In embodiments, $R^1$ is unsubstituted $C_3$-$C_4$ alkyl. In embodiments, $R^1$ is hydrogen or —$CH_3$. In embodiments, $R^1$ is —$CH_3$. In embodiments, $R^1$ is hydrogen.

In embodiments, $R^1$ is independently hydrogen or substituted (e.g., substituted with a substituent group, a size-limited substituent group, or lower substituent group) or unsubstituted (e.g., $C_1$-$C_4$) alkyl. In embodiments, $R^1$ is substituted (e.g., substituted with a substituent group, a size-limited substituent group, or lower substituent group) $C_1$-$C_4$ alkyl. In embodiments, $R^1$ is unsubstituted $C_1$-$C_4$ alkyl. In embodiments, $R^1$ is substituted (e.g., substituted with a substituent group, a size-limited substituent group, or lower substituent group) $C_2$-$C_4$ alkyl. In embodiments, $R^1$ is unsubstituted $C_2$-$C_4$ alkyl. In embodiments, $R^1$ is substituted (e.g., substituted with a substituent group, a size-limited substituent group, or lower substituent group) $C_3$-$C_4$ alkyl. In embodiments, $R^1$ is unsubstituted $C_3$-$C_4$ alkyl. In embodiments, $R^1$ is hydrogen or —$CH_3$. In embodiments, $R^1$ is —$CH_3$. In embodiments, $R^1$ is hydrogen.

In embodiments, $R^2$ is hydrogen, halogen, —$CX_3$, —CN, —C(O)OH, —$CH_2C(O)OH$, —$C(O)NH_2$, —OH, —SH, —$NO_2$, —$NH_2$, —$NHNH_2$, —$ONH_2$, —NHC═(O)$NHNH_2$, substituted or unsubstituted $C_1$-$C_6$ alkyl. In embodiments, $R^2$ is halogen. In embodiments, $R^2$ is —$CX_3$. In embodiments, $R^2$ is —CN. In embodiments, $R^2$ is —C(O)OH. In embodiments, $R^2$ is —$CH_2C(O)OH$. In embodiments, $R^2$ is —$C(O)NH_2$. In embodiments, $R^2$ is —OH. In embodiments, $R^2$ is —SH. In embodiments, $R^2$ is —$NO_2$. In embodiments, $R^2$ is —$NH_2$. In embodiments, $R^2$ is —$NHNH_2$. In embodiments, $R^2$ is —$ONH_2$.

In embodiments, $R^2$ is hydrogen, halogen, —$CX_3$, —CN, —C(O)OH, —$CH_2C(O)OH$, —$C(O)NH_2$, —OH, —SH, —$NO_2$, —$NH_2$, —$NHNH_2$, —$ONH_2$, —NHC═(O)$NHNH_2$, substituted (e.g., substituted with a substituent group, a size-limited substituent group, or lower substituent group) or unsubstituted $C_1$-$C_6$ alkyl. In embodiments, $R^2$ is halogen. In embodiments, $R^2$ is —$CX_3$. In embodiments, $R^2$ is —CN. In embodiments, $R^2$ is —C(O)OH. In embodiments, $R^2$ is —$CH_2C(O)OH$. In embodiments, $R^2$ is —$C(O)NH_2$. In embodiments, $R^2$ is —OH. In embodiments, $R^2$ is —SH. In embodiments, $R^2$ is —$NO_2$. In embodiments, $R^2$ is —$NH_2$. In embodiments, $R^2$ is —$NHNH_2$. In embodiments, $R^2$ is —$ONH_2$.

In embodiments, $R^2$ is substituted or unsubstituted $C_1$-$C_4$ alkyl. In embodiments, $R^2$ is substituted $C_1$-$C_4$ alkyl. In embodiments, $R^2$ is unsubstituted $C_1$-$C_4$ alkyl. In embodiments, $R^2$ is substituted or unsubstituted $C_2$-$C_4$ alkyl. In embodiments, $R^2$ is unsubstituted $C_2$-$C_4$ alkyl. In embodiments, $R^2$ is substituted $C_2$-$C_4$ alkyl. In embodiments, $R^2$ is substituted or unsubstituted $C_3$-$C_4$ alkyl. In embodiments, $R^2$ is substituted $C_3$-$C_4$ alkyl. In embodiments, $R^2$ is unsubstituted $C_3$-$C_4$ alkyl. In embodiments, $R^2$ is hydrogen or —$CH_3$. In embodiments, $R^2$ is —$CH_3$. In embodiments, $R^2$ is hydrogen.

In embodiments, $R^2$ is substituted (e.g., substituted with a substituent group, a size-limited substituent group, or lower substituent group) or unsubstituted $C_1$-$C_4$ alkyl. In embodiments, $R^2$ is substituted (e.g., substituted with a substituent group, a size-limited substituent group, or lower substituent group) $C_1$-$C_4$ alkyl. In embodiments, $R^2$ is unsubstituted $C_1$-$C_4$ alkyl. In embodiments, $R^2$ is substituted (e.g., substituted with a substituent group, a size-limited substituent group, or lower substituent group) or unsubstituted $C_2$-$C_4$ alkyl. In embodiments, $R^2$ is unsubstituted $C_2$-$C_4$ alkyl. In embodiments, $R^2$ is substituted (e.g., substituted with a substituent group, a size-limited substituent group, or lower substituent group) $C_2$-$C_4$ alkyl. In embodiments, $R^2$ is substituted (e.g., substituted with a substituent group, a size-limited substituent group, or lower substituent group) or unsubstituted $C_3$-$C_4$ alkyl. In embodiments, $R^2$ is substituted (e.g., substituted with a substituent group, a size-limited substituent group, or lower substituent group) $C_3$-$C_4$ alkyl. In embodiments, $R^2$ is unsubstituted $C_3$-$C_4$ alkyl. In embodiments, $R^2$ is hydrogen or —$CH_3$. In embodiments, $R^2$ is —$CH_3$. In embodiments, $R^2$ is hydrogen.

In embodiments, $R^3$ is independently hydrogen, halogen, —$CX_3$, —CN, —C(O)OH, —$CH_2C(O)OH$, —$C(O)NH_2$, —OH, —SH, —$NO_2$, —$NH_2$, —$NHNH_2$, —$ONH_2$, —NHC═(O)$NHNH_2$, or substituted or unsubstituted (e.g., $C_1$-$C_6$) alkyl. In embodiments, $R^3$ is independently halogen. In embodiments, $R^3$ is —$CX_3$. In embodiments, $R^3$ is —CN. In embodiments, $R^3$ is —C(O)OH. In embodiments, $R^3$ is —$CH_2C(O)OH$. In embodiments, $R^3$ is —$C(O)NH_2$. In embodiments, $R^3$ is —OH. In embodiments, $R^3$ is —SH. In embodiments, $R^3$ is —$NO_2$. In embodiments, $R^3$ is —$NH_2$. In embodiments, $R^3$ is —$NHNH_2$. In embodiments, $R^3$ is —$ONH_2$.

In embodiments, $R^3$ is substituted or unsubstituted $C_1$-$C_4$ alkyl. In embodiments, $R^3$ is substituted $C_1$-$C_4$ alkyl. In embodiments, $R^3$ is unsubstituted $C_1$-$C_4$ alkyl. In embodiments, $R^3$ is substituted or unsubstituted $C_2$-$C_4$ alkyl. In embodiments, $R^3$ is unsubstituted $C_2$-$C_4$ alkyl. In embodiments, $R^3$ is substituted $C_2$-$C_4$ alkyl. In embodiments, $R^3$ is substituted or unsubstituted $C_3$-$C_4$ alkyl. In embodiments, $R^3$ is substituted $C_3$-$C_4$ alkyl. In embodiments, $R^3$ is unsubstituted $C_3$-$C_4$ alkyl. In embodiments, $R^3$ is independently hydrogen or —$CH_3$. In embodiments, $R^3$ is —$CH_3$. In embodiments, $R^3$ is hydrogen.

In embodiments, $R^3$ is independently hydrogen, halogen, —$CX_3$, —CN, —C(O)OH, —$CH_2C(O)OH$, —$C(O)NH_2$, —OH, —SH, —$NO_2$, —$NH_2$, —$NHNH_2$, —$ONH_2$, —NHC═(O)$NHNH_2$, or substituted (e.g., substituted with a substituent group, a size-limited substituent group, or lower substituent group) or unsubstituted (e.g., $C_1$-$C_6$) alkyl. In embodiments, $R^3$ is independently halogen. In embodiments, $R^3$ is —$CX_3$. In embodiments, $R^3$ is —CN. In embodiments, $R^3$ is —C(O)OH. In embodiments, $R^3$ is —$CH_2C(O)OH$. In embodiments, $R^3$ is —$C(O)NH_2$. In embodiments, $R^3$ is —OH. In embodiments, $R^3$ is —SH. In embodiments, $R^3$ is —$NO_2$. In embodiments, $R^3$ is —$NH_2$. In embodiments, $R^3$ is —$NHNH_2$. In embodiments, $R^3$ is —$ONH_2$.

In embodiments, $R^3$ is substituted (e.g., substituted with a substituent group, a size-limited substituent group, or lower substituent group) or unsubstituted $C_1$-$C_4$ alkyl. In embodiments, $R^3$ is substituted (e.g., substituted with a substituent group, a size-limited substituent group, or lower substituent group) $C_1$-$C_4$ alkyl. In embodiments, $R^3$ is unsubstituted $C_1$-$C_4$ alkyl. In embodiments, $R^3$ is substituted (e.g., substituted with a substituent group, a size-limited substituent group, or lower substituent group) or unsubstituted $C_2$-$C_4$ alkyl. In embodiments, $R^3$ is unsubstituted $C_2$-$C_4$ alkyl. In embodiments, $R^3$ is substituted (e.g., substituted with a substituent group, a size-limited substituent group, or lower substituent group) $C_2$-$C_4$ alkyl. In embodiments, $R^3$ is substituted (e.g., substituted with a substituent group, a size-limited substituent group, or lower substituent group) or unsubstituted $C_3$-$C_4$ alkyl. In embodiments, $R^3$ is substituted (e.g., substituted with a substituent group, a size-limited substituent group, or lower substituent group) $C_3$-$C_4$ alkyl. In embodiments, $R^3$ is unsubstituted $C_3$-$C_4$ alkyl. In embodiments, $R^3$ is independently hydrogen or —$CH_3$. In embodiments, $R^3$ is —$CH_3$. In embodiments, $R^3$ is hydrogen.

In embodiments, $R^4$ is independently hydrogen, halogen, —$CX_3$, —CN, —C(O)OH, —$CH_2C(O)OH$, —$C(O)NH_2$, —OH, —SH, —$NO_2$, —$NH_2$, —$NHNH_2$, —$ONH_2$, —NHC═(O)$NHNH_2$, substituted or unsubstituted (e.g., $C_1$-$C_6$ alkyl). In embodiments, $R^4$ is independently halogen. In embodiments, $R^4$ is —$CX_3$. In embodiments, $R^4$ is —CN. In embodiments, $R^4$ is —C(O)OH. In embodiments, $R^4$ is —$CH_2C(O)OH$. In embodiments, $R^4$ is —$C(O)NH_2$. In embodiments, $R^4$ is —OH. In embodiments, $R^4$ is —SH. In embodiments, $R^4$ is —$NO_2$. In embodiments, $R^4$ is —$NH_2$. In embodiments, $R^4$ is —$NHNH_2$. In embodiments, $R^4$ is —$ONH_2$.

In embodiments, $R^4$ is substituted or unsubstituted $C_1$-$C_4$ alkyl. In embodiments, $R^4$ is substituted $C_1$-$C_4$ alkyl. In embodiments, $R^4$ is unsubstituted $C_1$-$C_4$ alkyl. In embodiments, $R^4$ is substituted or unsubstituted $C_2$-$C_4$ alkyl. In embodiments, $R^4$ is unsubstituted $C_2$-$C_4$ alkyl. In embodiments, $R^4$ is substituted $C_2$-$C_4$ alkyl. In embodiments, $R^4$ is substituted or unsubstituted $C_3$-$C_4$ alkyl. In embodiments, $R^4$ is substituted $C_3$-$C_4$ alkyl. In embodiments, $R^4$ is unsubstituted $C_3$-$C_4$ alkyl. In embodiments, $R^4$ is independently hydrogen or —$CH_3$. In embodiments, $R^4$ is —$CH_3$. In embodiments, $R^4$ is hydrogen.

In embodiments, $R^4$ is independently hydrogen, halogen, —$CX_3$, —CN, —C(O)OH, —$CH_2C(O)OH$, —$C(O)NH_2$, —OH, —SH, —$NO_2$, —$NH_2$, —$NHNH_2$, —$ONH_2$, —NHC═(O)$NHNH_2$, —$SO_3H$, substituted (e.g., substituted with a substituent group, a size-limited substituent group, or lower substituent group) or unsubstituted (e.g., $C_1$-$C_6$ alkyl). In embodiments, $R^4$ is independently halogen. In embodiments, $R^4$ is —$CX_3$. In embodiments, $R^4$ is —CN. In embodiments, $R^4$ is —C(O)OH. In embodiments, $R^4$ is —$CH_2C(O)OH$. In embodiments, $R^4$ is —$C(O)NH_2$. In embodiments, $R^4$ is —OH. In embodiments, $R^4$ is —SH. In embodiments, $R^4$ is —$NO_2$. In embodiments, $R^4$ is —$NH_2$. In embodiments, $R^4$ is —$NHNH_2$. In embodiments, $R^4$ is —$ONH_2$.

In embodiments, $R^4$ is substituted (e.g., substituted with a substituent group, a size-limited substituent group, or lower substituent group) or unsubstituted $C_1$-$C_4$ alkyl. In embodiments, $R^4$ is substituted (e.g., substituted with a substituent group, a size-limited substituent group, or lower substituent group) $C_1$-$C_4$ alkyl. In embodiments, $R^4$ is unsubstituted $C_1$-$C_4$ alkyl. In embodiments, $R^4$ is substituted (e.g., substituted with a substituent group, a size-limited substituent group, or lower substituent group) or unsubstituted $C_2$-$C_4$ alkyl. In embodiments, $R^4$ is unsubstituted $C_2$-$C_4$ alkyl. In embodiments, $R^4$ is substituted (e.g., substituted with a substituent group, a size-limited substituent group, or lower substituent group) $C_2$-$C_4$ alkyl. In embodiments, $R^4$ is substituted (e.g., substituted with a substituent group, a size-limited substituent group, or lower substituent group) or unsubstituted $C_3$-$C_4$ alkyl. In embodiments, $R^4$ is substituted (e.g., substituted with a substituent group, a size-limited substituent group, or lower substituent group) $C_3$-$C_4$ alkyl.

In embodiments, $R^4$ is unsubstituted $C_3$-$C_4$ alkyl. In embodiments, $R^4$ is independently hydrogen or —$CH_3$. In embodiments, $R^4$ is —$CH_3$. In embodiments, $R^4$ is hydrogen. In embodiments, $R^4$ is —$SO_3H$.

In embodiments, X is —F. In embodiments, X is —$C_1$. In embodiments, X is —Br. In embodiments, X is —I. In embodiments, n is 1. In embodiments, n is 2. In embodiments, the symbol $z^1$ and $z^2$ are 1. In embodiments, $z^1$ is 2. In embodiments, $z^2$ is 2. In embodiments, $z^1$ is 1. In embodiments, $z^2$ is 1.

In embodiments, $L^1$ is a covalent linker. In embodiments, $L^1$ may be a bond, —O—, —S—, —C(O)—, —C(O)O—, —C(O)NH—, —$S(O)_2NH$—, —NH—, —NHC(O)NH—, substituted (e.g., substituted with a substituent group, a size-limited substituent or a lower substituent group) or unsubstituted alkylene, substituted (e.g., substituted with a substituent group, a size-limited substituent or a lower substituent group) or unsubstituted heteroalkylene, substituted (e.g., substituted with a substituent group, a size-limited substituent or a lower substituent group) or unsubstituted cycloalkylene, substituted (e.g., substituted with a substituent group, a size-limited substituent or a lower substituent group) or unsubstituted heterocycloalkylene, substituted (e.g., substituted with a substituent group, a size-limited substituent or a lower substituent group) or unsubstituted arylene or substituted (e.g., substituted with a substituent group, a size-limited substituent or a lower substituent group) or unsubstituted heteroarylene.

In embodiments, $L^1$ may be a bond, —O—, —S—, —C(O)—, —C(O)O—, —C(O)NH—, —$S(O)_2NH$—, —NH—, —NHC(O)NH—, substituted or unsubstituted (e.g., $C_1$-$C_{20}$, $C_1$-$C_{10}$, $C_1$-$C_5$) alkylene, substituted or unsubstituted (e.g., 2 to 20 membered, 2 to 10 membered, 2 to 5 membered) heteroalkylene, substituted or unsubstituted (e.g., $C_3$-$C_8$, $C_3$-$C_6$, $C_3$-$C_5$) cycloalkylene, substituted or unsubstituted (e.g., 3 to 8 membered, 3 to 6 membered, 3 to 5 membered) heterocycloalkylene, substituted or unsubstituted (e.g., $C_6$-$C_{10}$, $C_6$-$C_8$, $C_6$-$C_5$) arylene or substituted or unsubstituted (e.g., 5 to 10 membered, 5 to 8 membered, 5 to 6 membered) heteroarylene.

In embodiments, $L^1$ is substituted or unsubstituted $C_1$-$C_{10}$ alkylene. In embodiments, $L^1$ is substituted or unsubstituted $C_2$-$C_{10}$ alkylene. In embodiments, $L^1$ is substituted or unsubstituted $C_4$-$C_{10}$ alkylene. In embodiments, $L^1$ is substituted or unsubstituted $C_6$-$C_{10}$ alkylene. In embodiments, $L^1$ is substituted or unsubstituted $C_8$-$C_{10}$ alkylene. In embodiments, $L^1$ is substituted or unsubstituted $C_2$-$C_5$ alkylene. In embodiments, $L^1$ is substituted or unsubstituted $C_4$-$C_8$ alkylene. In embodiments, $L^1$ is substituted $C_1$-$C_{10}$ alkylene. In embodiments, $L^1$ is substituted $C_2$-$C_{10}$ alkylene. In embodiments, $L^1$ is substituted $C_4$-$C_{10}$ alkylene. In embodiments, $L^1$ is substituted $C_6$-$C_{10}$ alkylene. In embodiments, $L^1$ is substituted $C_8$-$C_{10}$ alkylene. In embodiments, $L^1$ is substituted $C_2$-$C_8$ alkylene. In embodiments, $L^1$ is substituted $C_4$-$C_8$ alkylene. In embodiments, $L^1$ is substituted $C_6$ alkylene.

In embodiments, $L^1$ is substituted or unsubstituted 1 to 10 membered heteroalkylene. In embodiments, $L^1$ is substituted or unsubstituted 2 to 10 membered heteroalkylene. In embodiments, $L^1$ is substituted or unsubstituted 4 to 10 membered heteroalkylene. In embodiments, $L^1$ is substituted or unsubstituted 6 to 10 membered heteroalkylene. In embodiments, $L^1$ is substituted or unsubstituted 8 to 10 membered heteroalkylene. In embodiments, $L^1$ is unsubstituted 1 to 10 membered heteroalkylene. In embodiments, $L^1$ is unsubstituted 4 to 10 membered heteroalkylene. In embodiments, $L^1$ is unsubstituted 2 to 8 membered heteroalkylene. In embodiments, $L^1$ is unsubstituted 2 to 6 membered heteroalkylene. In embodiments, $L^1$ is unsubstituted 7 membered heteroalkylene.

In embodiments, $L^1$ may be a bond, —O—, —S—, —C(O)—, —C(O)O—, —C(O)NH—, —$S(O)_2NH$—, —NH—, —NHC(O)NH—, substituted (e.g., substituted with a substituent group, a size-limited substituent group, or lower substituent group) or unsubstituted (e.g., $C_1$-$C_{20}$, $C_1$-$C_{10}$, $C_1$-$C_5$) alkylene, substituted (e.g., substituted with a substituent group, a size-limited substituent group, or lower substituent group) or unsubstituted (e.g., 2 to 20 membered, 2 to 10 membered, 2 to 5 membered) heteroalkylene, substituted (e.g., substituted with a substituent group, a size-limited substituent group, or lower substituent group) or unsubstituted (e.g., $C_3$-$C_8$, $C_3$-$C_6$, $C_3$-$C_5$) cycloalkylene, substituted (e.g., substituted with a substituent group, a size-limited substituent group, or lower substituent group) or unsubstituted (e.g., 3 to 8 membered, 3 to 6 membered, 3 to 5 membered) heterocycloalkylene, substituted (e.g., substituted with a substituent group, a size-limited substituent group, or lower substituent group) or unsubstituted (e.g., $C_6$-$C_{10}$, $C_6$-$C_8$, $C_6$-$C_5$) arylene or substituted (e.g., substituted with a substituent group, a size-limited substituent group, or lower substituent group) or unsubstituted (e.g., 5 to 10 membered, 5 to 8 membered, 5 to 6 membered) heteroarylene.

In embodiments, $L^1$ is substituted (e.g., substituted with a substituent group, a size-limited substituent group, or lower substituent group) or unsubstituted $C_1$-$C_{10}$ alkylene. In embodiments, $L^1$ is substituted (e.g., substituted with a substituent group, a size-limited substituent group, or lower substituent group) or unsubstituted $C_2$-$C_{10}$ alkylene. In embodiments, $L^1$ is substituted (e.g., substituted with a substituent group, a size-limited substituent group, or lower substituent group) or unsubstituted $C_4$-$C_{10}$ alkylene. In embodiments, $L^1$ is substituted (e.g., substituted with a substituent group, a size-limited substituent group, or lower substituent group) or unsubstituted $C_6$-$C_{10}$ alkylene. In embodiments, $L^1$ is substituted (e.g., substituted with a substituent group, a size-limited substituent group, or lower substituent group) or unsubstituted $C_8$-$C_{10}$ alkylene. In embodiments, $L^1$ is substituted (e.g., substituted with a substituent group, a size-limited substituent group, or lower substituent group) or unsubstituted $C_2$-$C_8$ alkylene. In embodiments, $L^1$ is substituted (e.g., substituted with a substituent group, a size-limited substituent group, or lower substituent group) or unsubstituted $C_4$-$C_8$ alkylene. In embodiments, $L^1$ is substituted (e.g., substituted with a substituent group, a size-limited substituent group, or lower substituent group) $C_1$-$C_{10}$ alkylene. In embodiments, $L^1$ is substituted (e.g., substituted with a substituent group, a size-limited substituent group, or lower substituent group) $C_2$-$C_{10}$ alkylene. In embodiments, $L^1$ is substituted (e.g., substituted with a substituent group, a size-limited substituent group, or lower substituent group) $C_4$-$C_{10}$ alkylene. In embodiments, $L^1$ is substituted (e.g., substituted with a substituent group, a size-limited substituent group, or lower substituent group) $C_6$-$C_{10}$ alkylene. In embodiments, $L^1$ is substituted (e.g., substituted with a substituent group, a size-limited substituent group, or lower substituent group) $C_8$-$C_{10}$ alkylene. In embodiments, $L^1$ is substituted (e.g., substituted with a substituent group, a size-limited substituent group, or lower substituent group) $C_2$-$C_8$ alkylene. In embodiments, $L^1$ is substituted (e.g., substituted with a substituent group, a size-limited substituent group, or lower substituent group) $C_4$-$C_8$ alkylene. In embodiments, $L^1$ is substituted (e.g., substituted with a substituent group, a size-limited substituent group, or lower substituent group) $C_6$ alkylene.

In embodiments, $L^1$ is substituted (e.g., substituted with a substituent group, a size-limited substituent group, or lower substituent group) or unsubstituted 1 to 10 membered heteroalkylene. In embodiments, $L^1$ is substituted (e.g., substituted with a substituent group, a size-limited substituent group, or lower substituent group) or unsubstituted 2 to 10 membered heteroalkylene. In embodiments, $L^1$ is substituted (e.g., substituted with a substituent group, a size-limited substituent group, or lower substituent group) or unsubstituted 4 to 10 membered heteroalkylene. In embodiments, $L^1$ is substituted (e.g., substituted with a substituent group, a size-limited substituent group, or lower substituent group) or unsubstituted 6 to 10 membered heteroalkylene. In embodiments, $L^1$ is substituted (e.g., substituted with a substituent group, a size-limited substituent group, or lower substituent group) or unsubstituted 8 to 10 membered heteroalkylene. In embodiments, $L^1$ is unsubstituted 1 to 10 membered heteroalkylene. In embodiments, $L^1$ is unsubstituted 4 to 10 membered heteroalkylene. In embodiments, $L^1$ is unsubstituted 2 to 8 membered heteroalkylene. In embodiments, $L^1$ is unsubstituted 2 to 6 membered heteroalkylene. In embodiments, $L^1$ is unsubstituted 7 membered heteroalkylene. In embodiments, $L^1$ is unsubstituted alkylene or unsubstituted heteroalkylene. In embodiments, $L^1$ is unsubstituted heteroalkylene.

In embodiments $L^1$ has the formula:

$$—L^{1A}—L^{2A}—. \qquad \text{(III)}$$

$L^{1A}$ is bond, —O—, —S—, —C(O)—, —C(O)O—, —C(O)NH—, —$S(O)_2$NH—, —NH—, —NHC(O)NH—, substituted (e.g., substituted with a substituent group, a size-limited substituent or a lower substituent group) or unsubstituted alkylene, substituted (e.g., substituted with a substituent group, a size-limited substituent or a lower substituent group) or unsubstituted heteroalkylene, substituted (e.g., substituted with a substituent group, a size-limited substituent or a lower substituent group) or unsubstituted cycloalkylene, substituted (e.g., substituted with a substituent group, a size-limited substituent or a lower substituent group) or unsubstituted heterocycloalkylene, substituted (e.g., substituted with a substituent group, a size-limited substituent or a lower substituent group) or unsubstituted arylene or substituted (e.g., substituted with a substituent group, a size-limited substituent or a lower substituent group) or unsubstituted heteroarylene.

$L^{2A}$ is bond, —O—, —S—, —C(O)—, —C(O)O—, —C(O)NH—, —$S(O)_2$NH—, —NH—, —NHC(O)NH—, substituted (e.g., substituted with a substituent group, a size-limited substituent or a lower substituent group) or unsubstituted alkylene, substituted (e.g., substituted with a substituent group, a size-limited substituent or a lower substituent group) or unsubstituted heteroalkylene, substituted (e.g., substituted with a substituent group, a size-limited substituent or a lower substituent group) or unsubstituted cycloalkylene, substituted (e.g., substituted with a substituent group, a size-limited substituent or a lower substituent group) or unsubstituted heterocycloalkylene, substituted (e.g., substituted with a substituent group, a size-limited substituent or a lower substituent group) or unsubstituted arylene or substituted (e.g., substituted with a substituent group, a size-limited substituent or a lower substituent group) or unsubstituted heteroarylene.

In embodiments, $L^{1A}$ is substituted or unsubstituted alkylene and $L^{2A}$ is —C(O)—, —C(O)O—, —OC(O)—, —C(O)NH—, —NH—, —NHC(O)—, —O—, —S—, —S(O)—, —$S(O)_2$NH—, —NHS$(O)_2$—, substituted or unsubstituted (e.g., $C_1$-$C_{10}$) alkylene or substituted or unsubstituted (e.g., 1 to 10 membered) heteroalkylene.

$L^{1A}$ and $L^{2A}$ may independently be a bond, —O—, —S—, —C(O)—, —C(O)O—, —C(O)NH—, —$S(O)_2$NH—, —NH—, —NHC(O)NH—, substituted or unsubstituted (e.g., $C_1$-$C_{20}$, $C_1$-$C_{10}$, $C_1$-$C_5$) alkylene, substituted or unsubstituted (e.g., 2 to 20 membered, 2 to 10 membered, 2 to 5 membered) heteroalkylene, substituted or unsubstituted (e.g., $C_3$-$C_8$, $C_3$-$C_6$, $C_3$-$C_5$) cycloalkylene, substituted or unsubstituted (e.g., 3 to 8 membered, 3 to 6 membered, 3 to 5 membered) heterocycloalkylene, substituted or unsubstituted (e.g., $C_6$-$C_{10}$, $C_6$-$C_8$, $C_6$-$C_5$) arylene or substituted or unsubstituted (e.g., 5 to 10 membered, 5 to 8 membered, 5 to 6 membered) heteroarylene.

In embodiments, $L^{1A}$ is substituted or unsubstituted $C_1$-$C_{10}$ alkylene. In embodiments, $L^{1A}$ is substituted $C_2$-$C_{10}$ alkylene. In embodiments, $L^{1A}$ is substituted $C_4$-$C_{10}$ alkylene. In embodiments, $L^{1A}$ is substituted $C_6$-$C_{10}$ alkylene. In embodiments, $L^{1A}$ is substituted $C_8$-$C_{11}$ alkylene. In embodiments, $L^{1A}$ is substituted $C_1$-$C_8$ alkylene. In embodiments, $L^{1A}$ is substituted $C_1$-$C_6$ alkylene. In embodiments, $L^{1A}$ is substituted $C_1$-$C_4$ alkylene. In embodiments, $L^{1A}$ is unsubstituted $C_2$-$C_{10}$ alkylene. In embodiments, $L^{1A}$ is unsubstituted $C_4$-$C_{10}$ alkylene. In embodiments, $L^{1A}$ is unsubstituted $C_6$-$C_{10}$ alkylene. In embodiments, $L^{1A}$ is unsubstituted $C_8$-$C_{10}$ alkylene. In embodiments, $L^{1A}$ is unsubstituted $C_1$-$C_8$ alkylene. In embodiments, $L^{1A}$ is unsubstituted $C_1$-$C_6$ alkylene. In embodiments, $L^{1A}$ is unsubstituted $C_1$-$C_4$ alkylene. In embodiments, $L^{1A}$ is unsubstituted $C_5$ alkylene.

In embodiments, $L^{1A}$ is substituted (e.g., substituted with a substituent group, a size-limited substituent group, or lower substituent group) or unsubstituted alkylene and $L^{2A}$ is —C(O)—, —C(O)O—, —OC(O)—, —C(O)NH—, —NH—, —NHC(O)—, —O—, —S—, —S(O)—, —$S(O)_2$NH—, —NHS$(O)_2$—, substituted (e.g., substituted with a substituent group, a size-limited substituent group, or lower substituent group) or unsubstituted (e.g., $C_1$-$C_{10}$) alkylene or substituted (e.g., substituted with a substituent group, a size-limited substituent group, or lower substituent group) or unsubstituted (e.g., 1 to 10 membered) heteroalkylene.

$L^{1A}$ and $L^{2A}$ may independently be a bond, —O—, —S—, —C(O)—, —C(O)O—, —C(O)NH—, —$S(O)_2$NH—, —NH—, —NHC(O)NH—, substituted (e.g., substituted with a substituent group, a size-limited substituent group, or lower substituent group) or unsubstituted (e.g., $C_1$-$C_{20}$, $C_1$-$C_{10}$, $C_1$-$C_5$) alkylene, substituted (e.g., substituted with a substituent group, a size-limited substituent group, or lower substituent group) or unsubstituted (e.g., 2 to 20 membered, 2 to 10 membered, 2 to 5 membered) heteroalkylene, substituted (e.g., substituted with a substituent group, a size-limited substituent group, or lower substituent group) or unsubstituted (e.g., $C_3$-$C_8$, $C_3$-$C_6$, $C_3$-$C_5$) cycloalkylene, substituted (e.g., substituted with a substituent group, a size-limited substituent group, or lower substituent group) or unsubstituted (e.g., 3 to 8 membered, 3 to 6 membered, 3 to 5 membered) heterocycloalkylene, substituted (e.g., substituted with a substituent group, a size-limited substituent group, or lower substituent group) or unsubstituted (e.g., $C_6$-$C_{10}$, $C_6$-$C_8$, $C_6$-$C_5$) arylene or substituted (e.g., substituted with a substituent group, a size-limited substituent group, or lower substituent group) or unsubstituted (e.g., 5 to 10 membered, 5 to 8 membered, 5 to 6 membered) heteroarylene.

In embodiments, $L^{1A}$ is substituted (e.g., substituted with a substituent group, a size-limited substituent group, or lower substituent group) or unsubstituted $C_1$-$C_{10}$ alkylene. In embodiments, $L^{1A}$ is substituted (e.g., substituted with a substituent group, a size-limited substituent group, or lower substituent group) $C_2$-$C_{10}$ alkylene. In embodiments, $L^{1A}$ is substituted (e.g., substituted with a substituent group, a size-limited substituent group, or lower substituent group) $C_4$-$C_{10}$ alkylene. In embodiments, $L^{1A}$ is substituted (e.g., substituted with a substituent group, a size-limited substituent group, or lower substituent group) $C_6$-$C_{10}$ alkylene. In embodiments, $L^{1A}$ is substituted (e.g., substituted with a substituent group, a size-limited substituent group, or lower substituent group) $C_5$-$C_{10}$ alkylene. In embodiments, $L^{1A}$ is substituted (e.g., substituted with a substituent group, a size-limited substituent group, or lower substituent group) $C_1$-$C_8$ alkylene. In embodiments, $L^{1A}$ is substituted (e.g., substituted with a substituent group, a size-limited substituent group, or lower substituent group) $C_1$-$C_6$ alkylene. In embodiments, $L^{1A}$ is substituted (e.g., substituted with a substituent group, a size-limited substituent group, or lower substituent group) $C_1$-$C_4$ alkylene. In embodiments, $L^{1A}$ is unsubstituted $C_2$-$C_{10}$ alkylene. In embodiments, $L^{1A}$ is unsubstituted $C_4$-$C_{10}$ alkylene. In embodiments, $L^{1A}$ is unsubstituted $C_6$-$C_{10}$ alkylene. In embodiments, $L^{1A}$ is unsubstituted $C_8$-$C_{10}$ alkylene. In embodiments, $L^{1A}$ is unsubstituted $C_1$-$C_8$ alkylene. In embodiments, $L^{1A}$ is unsubstituted $C_1$-$C_6$ alkylene. In embodiments, $L^{1A}$ is unsubstituted $C_1$-$C_4$ alkylene. In embodiments, $L^{1A}$ is unsubstituted $C_5$ alkylene.

In embodiments, $L^{1A}$ is a substituted or unsubstituted alkylene; and $L^{2A}$ is a bond, —C(O)—, —C(O)O—, —OC(O)—, —C(O)NH—, —NH—, —NHC(O)—, —O—, —S—, —S(O)—, —S(O)$_2$NH—, —NHS(O)$_2$—, substituted or unsubstituted alkylene or substituted or unsubstituted heteroalkylene.

In embodiments, $L^{2A}$ is —C(O)—. In embodiments, $L^{2A}$ is —C(O)O—. In embodiments, $L^{2A}$ is —OC(O)—. In embodiments, $L^{2A}$ is —C(O)NH—. In embodiments, $L^{2A}$ is —NH—. In embodiments, $L^{2A}$ is —NHC(O)—. In embodiments, $L^{2A}$ is —O—. In embodiments, $L^{2A}$ is —S—. In embodiments, $L^{2A}$ is —S(O)—. In embodiments, $L^{2A}$ is —S(O)$_2$NH—. In embodiments, $L^{2A}$ is —NHS(O)$_2$—.

In embodiments $L^1$ has the formula:

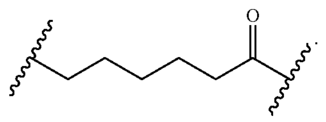 [SMILES: *CCCCCC(*)=O]

In embodiments $L^1$ has the formula:

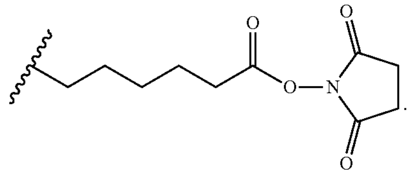 [SMILES: *CCCCCC(=O)ON1C(=O)CCC1=O]

In embodiments $L^1$ has the formula:

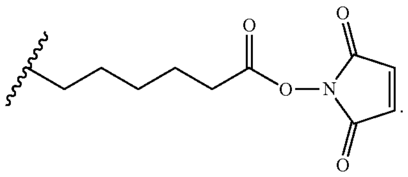 [SMILES: *CCCCCC(=O)ON1C(=O)C=CC1=O]

In embodiments -$L^{1A}$-$L^{2A}$- has the formula:

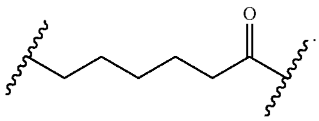 [SMILES: *CCCCCC(*)=O]

In embodiments -$L^{1A}$-$L^{2A}$- has the formula:

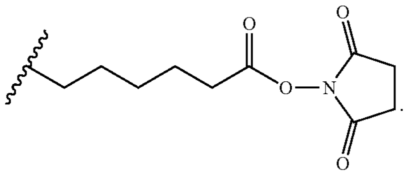 [SMILES: *CCCCCC(=O)ON1C(=O)CCC1=O]

In embodiments -$L^{1A}$-$L^{2A}$- has the formula:

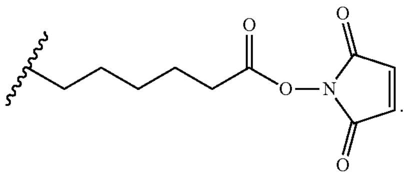 [SMILES: *CCCCCC(=O)ON1C(=O)C=CC1=O]

In embodiments $L^1$ has the formula:

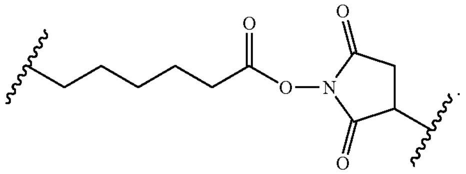 [SMILES: *CCCCCC(=O)ON1C(=O)CC(*)C1=O]

In embodiments, $L^1$ is covalently attached to an alanine of the non-cell penetrating protein. In embodiments, $L^1$ is covalently attached to an arginine of the non-cell penetrating protein. In embodiments, $L^1$ is covalently attached to an asparagine of the non-cell penetrating protein. In embodiments, $L^1$ is covalently attached to an aspartic acid of the non-cell penetrating protein. In embodiments, $L^1$ is covalently attached to a cysteine of the non-cell penetrating protein. In embodiments, $L^1$ is covalently attached to a glutamine of the non-cell penetrating protein. In embodiments, $L^1$ is covalently attached to a glutamic acid of the non-cell penetrating protein. In embodiments, $L^1$ is covalently attached to a glycine of the non-cell penetrating protein. In embodiments, $L^1$ is covalently attached to an isoleucine of the non-cell penetrating protein. In embodiments, $L^1$ is covalently attached to a leucine of the non-cell penetrating protein. In embodiments, $L^1$ is covalently attached to a lysine of the non-cell penetrating protein. In embodiments, $L^1$ is covalently attached to a methionine of the non-cell penetrating protein. In embodiments, $L^1$ is covalently attached to a phenylalanine of the non-cell penetrating protein. In embodiments, $L^1$ is covalently attached to a proline of the non-cell penetrating protein. In embodiments, $L^1$ is covalently attached to a serine of the non-cell penetrating protein. In embodiments, $L^1$ is covalently attached to a threonine of the non-cell penetrating protein. In embodiments, $L^1$ is covalently attached to a tryptophan of the non-cell penetrating protein. In embodiments, $L^1$ is covalently attached to a tyrosine of the non-cell penetrating protein. In embodiments, $L^1$ is covalently attached to a valine of the non-cell penetrating protein.

In embodiments, the cell-penetrating conjugate has the formula:

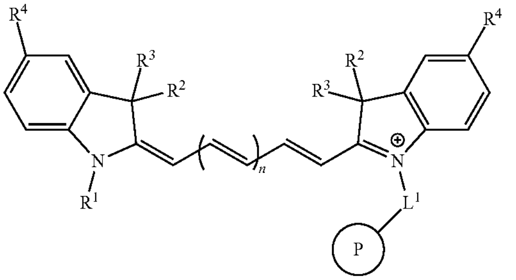

(or

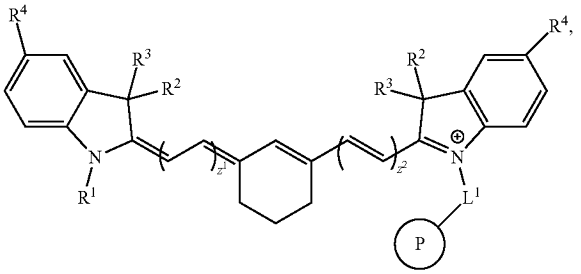

wherein $R^1$, $R^2$, $R^3$, $R^4$, $L^1$, n, P, $z^1$, and $z^2$ are as defined above and herein, including embodiments thereof.

In embodiments, the cell-penetrating conjugate has the formula:

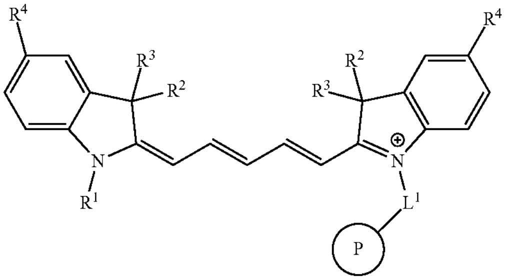

(or

-continued

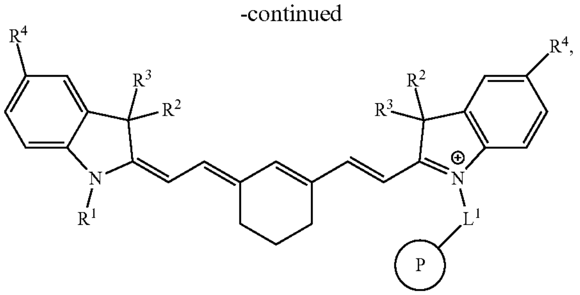

wherein $R^1$, $R^2$, $R^3$, $R^4$, $L^1$, n, P, $z^1$, and $z^2$ are as defined above and herein, including embodiments thereof.

In embodiments, the non-cell penetrating protein has a molecular weight of more than 25 kD. In embodiments, the non-cell penetrating protein has a molecular weight of about 25 kD to about 750 kD. Thus, the non-cell penetrating protein can have a molecular weight of at least about 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, or more kilodaltons (kD). In embodiments, the non-cell penetrating protein has a molecular weight from at least about 25 to 100 kD, at least about 25 to 150 kD, at least about 25 to 200 kD, at least about 25 to 250 kD, at least about 25 to 300 kD, at least about 25 to 350 kD, at least about 25 to 400 kD, at least about 25 to 450 kD, at least about 25 to 500 kD, at least about 25 to 550 kD, at least about 25 to 600 kD, at least about 25 to 650 kD, at least about 25 to 700 kD or at least above 25 to 750 kD.

In embodiments, the non-cell penetrating protein is an antibody. As discussed in more detail above, antibodies can be full length antibodies such as IgG, IgA, IgM, IgD or IgE antibodies or fragments thereof. In embodiments, the antibody is an IgG antibody or a fragment thereof. In embodiments, the antibody is an IgG antibody or a fragment thereof. In embodiments, the antibody is an Fv fragment or a humanized antibody. In embodiments, the antibody is an IgA, IgM, IgD or IgE antibody. In embodiments, the antibody is an Fv fragment. In embodiments, the antibody is a humanized antibody. In embodiments, the antibody is a chimeric antibody. In embodiments, the antibody is a therapeutic antibody, i.e., an antibody used in the treatment of disease. Thus, also provided are therapeutic antibodies attached the cell-penetrating conjugate wherein the antibody binds an intracellular target.

In embodiments, the non-cell penetrating protein binds an intracellular target. The intracellular target can be a therapeutic target or a diagnostic target or other target of interest located intracellularly, e.g., a target or structure, e.g., histone, to be imaged, e.g., by confocal microscopy. Thus, provided are cell penetrating conjugates bound to an intracellular target. In embodiments, the intracellular target is a target of a disease selected from the group consisting of autoimmune disease, inflammatory disease, metabolic disorder, developmental disorder, cardiovascular disease, liver disease, intestinal disease, infectious disease, endocrine disease, neurological disorder, and cancer. Examples of intracellular targets include without limitation oncogenic transcription factors including but not limited to STAT3, Myc, NFkB, AP1, HIF, mutant p53; oncoproteins including but not limited to Ras, Raf, MAPK, PI3 kinase, AKT, BTK, JAKs, SRC family members; immunomodulatory molecules including FOXp3, T-BET, GATA3, STAT1, 2, 3, 4, 5, 6. The target of a disease can be a diagnostic target or therapeutic target or other target of interest associated with the disease. Exemplary intracellular targets of cancer include, but are not limited to, STAT (e.g., STAT3), NFκB, PKB/Akt, Myc family members, steroid hormone receptors (e.g., estrogen receptor), ligands of steroid hormone receptors (e.g., cyclin D1), receptor tyrosine kinases (RTKs), HER2, EGFR, VEGFR, PDGFR, Src family members, Ras, Abl, BCR-Abl, NPM-Alk, Janus kinases (JAKs), Brutun's tyrosine kinase (BTK), and viral oncoproteins (e.g., an EBV protein, or an HPV protein, e.g., E6 and E7). In embodiments, the intracellular target of the infectious disease is a viral protein or viral transcript. Thus, the intracellular target can be a viral protein or viral transcript of a human immunodeficiency virus (HIV), influenza virus, herpes simplex cirus, epstein barr virus, cytomegalovirus, human papilloma virus, or hepatitis virus. In embodiments, the intracelluar target is a DNA binding protein including, but not limited to, a transcription factor, a transcriptional enhancer, a transcriptional repressor, a histone or post-translationally modified histone. In embodiments, the intracellular target is epigenetically modified DNA, e.g., methylated or hydroxymethylated cytosine (5mC or 5hmC), 5-formylcytosine (5fC) and 5-carboxylcytosine (5caC). In embodiments, the intracellular target is a nucleic acid, e.g., an RNA transcript or a nucleic acid. For example, the intracellular target may be the nucleic acid of an infectious pathogen, e.g., a parasite, virus or bacteria. In embodiments, the intracellular target is a signaling molecule or a transcription factor. In embodiments, the signaling molecule is a phosphatase or kinase. In embodiments, the intracellular target is a cancer target or located within a cancer cell. In embodiments, the intracellular target is a STAT, e.g., STAT3, Src, or exportin 7. In embodiments, the intracellular target is STAT3. In embodiments, the intracellular target is selected from the group consisting of STAT3, exportin 7 and Src. In embodiments, the intracellular target is phosphorylated Src. In embodiments, the cell penetrating conjugate is bound to an intracellular target. In embodiments, the non-cell penetrating protein further includes a detectable moiety.

III. Cell Compositions

In an aspect, a cell comprising the cell penetrating conjugate is as described herein, including embodiments (e.g. in an aspect, embodiment, example, figure, table, or claim). Provided are cells including one or more of the provided cell penetrating conjugates, e.g., the cells may include a plurality of cell penetrating conjugates. In embodiments, the conjugate is bound within the cell to an intracellular target. In embodiments, the cell is a cancer cell. In embodiments, the cell is a non-cancerous cell.

IV. Pharmaceutical Compositions

In an aspect, is provided a pharmaceutical composition including the cell penetrating conjugate as described herein, including embodiments (e.g. in an aspect, embodiment, example, figure, table, or claim) and a pharmaceutically acceptable carrier.

Provided herein are pharmaceutical compositions comprising the cell penetrating conjugates and a pharmaceutically acceptable carrier. The provided compositions are, inter alia, suitable for formulation and administration in vitro or in vivo. Suitable carriers and excipients and their formulations are described in Remington: The Science and Practice of Pharmacy, 21st Edition, David B. Troy, ed., Lippicott Williams & Wilkins (2005). By pharmaceutically acceptable carrier is meant a material that is not biologically or otherwise undesirable, i.e., the material is administered to a subject without causing undesirable biological effects or interacting in a deleterious manner with the other components of the pharmaceutical composition in which it is contained. If administered to a subject, the carrier is optionally selected to minimize degradation of the active ingredient and to minimize adverse side effects in the subject.

Pharmaceutical compositions provided by the present invention include compositions wherein the active ingredient (e.g. compositions described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, the recombinant proteins described herein will contain an amount of active ingredient effective to achieve the desired result, e.g., modulating the activity of a target molecule, and/or reducing, eliminating, or slowing the progression of disease symptoms. Determination of a therapeutically effective amount of a compound of the invention is well within the capabilities of those skilled in the art, especially in light of the detailed disclosure herein.

Provided compositions can include a single agent or more than one agent. The compositions for administration will commonly include an agent as described herein dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the subject's needs.

Solutions of the active compounds as free base or pharmacologically acceptable salt can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations can contain a preservative to prevent the growth of microorganisms.

Pharmaceutical compositions can be delivered via intranasal or inhalable solutions or sprays, aerosols or inhalants. Nasal solutions can be aqueous solutions designed to be administered to the nasal passages in drops or sprays. Nasal solutions can be prepared so that they are similar in many respects to nasal secretions. Thus, the aqueous nasal solutions usually are isotonic and slightly buffered to maintain a pH of 5.5 to 6.5. In addition, antimicrobial preservatives, similar to those used in ophthalmic preparations and appropriate drug stabilizers, if required, may be included in the formulation. Various commercial nasal preparations are known and can include, for example, antibiotics and antihistamines.

Oral formulations can include excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders. In some embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25-60%. The amount of active compounds in such compositions is such that a suitable dosage can be obtained.

For parenteral administration in an aqueous solution, for example, the solution should be suitably buffered and the liquid diluent first rendered isotonic with sufficient saline or glucose. Aqueous solutions, in particular, sterile aqueous media, are especially suitable for intravenous, intramuscular, subcutaneous and intraperitoneal administration. For example, one dosage could be dissolved in 1 ml of isotonic NaCl solution and either added to 1000 ml of hypodermoclysis fluid or injected at the proposed site of infusion.

Sterile injectable solutions can be prepared by incorporating the active compounds or constructs in the required amount in the appropriate solvent followed by filtered sterilization. Generally, dispersions are prepared by incorporating the various sterilized active ingredients into a sterile vehicle which contains the basic dispersion medium. Vacuum-drying and freeze-drying techniques, which yield a powder of the active ingredient plus any additional desired ingredients, can be used to prepare sterile powders for reconstitution of sterile injectable solutions. The preparation of more, or highly, concentrated solutions for direct injection is also contemplated. DMSO can be used as solvent for extremely rapid penetration, delivering high concentrations of the active agents to a small area.

The formulations of compounds can be presented in unit-dose or multi-dose sealed containers, such as ampules and vials. Thus, the composition can be in unit dosage form. In such form the preparation is subdivided into unit doses containing appropriate quantities of the active component. Thus, the compositions can be administered in a variety of unit dosage forms depending upon the method of administration. For example, unit dosage forms suitable for oral administration include, but are not limited to, powder, tablets, pills, capsules and lozenges.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated (e.g. symptoms of cancer and severity of such symptoms), kind of concurrent treatment, complications from the disease being treated or other health-related problems. Other therapeutic regimens or agents can be used in conjunction with the methods and compounds of the invention. Adjustment and manipulation of established dosages (e.g., frequency and duration) are well within the ability of those skilled in the art.

For any composition (e.g., the cell-penetrating conjugate provided) described herein, the therapeutically effective amount can be initially determined from cell culture assays. Target concentrations will be those concentrations of active compound(s) that are capable of achieving the methods described herein, as measured using the methods described herein or known in the art. As is well known in the art, effective amounts for use in humans can also be determined from animal models. For example, a dose for humans can be formulated to achieve a concentration that has been found to be effective in animals. The dosage in humans can be adjusted by monitoring effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to affect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred "Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "pharmaceutically acceptable salt" refers to salts derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

V. Methods of Delivery

In an aspect is provided a method of delivering a non-cell penetrating protein into a cell including contacting a cell with the cell penetrating conjugate as described herein, including embodiments (e.g. in an aspect, embodiment, example, figure, table, or claim). The method includes contacting the cell with the cell penetrating conjugate as provided herein including embodiments thereof. In embodiments, the non-cell penetrating protein binds the nuclear protein in the cytoplasm thereby forming a non-cell penetrating protein-nuclear protein complex. In embodiments, the non-cell penetrating protein-nuclear protein complex is not capable of entering the nucleus of the cell.

In embodiments, the cell penetrating conjugates are used for diagnosing a disease in a subject. Thus, provided is a method of diagnosing a disease in a subject comprising administering to the subject an effective amount of a cell penetrating conjugate or composition comprising a cell penetrating conjugate as described herein. Administration of the conjugate diagnoses the disease or one or more symptoms of the disease in the subject. The disclosed methods involve comparing the levels or activity of a biomarker, e.g., intracellular target of a disease, from a test sample to a control sample. As discussed above, a control sample or value refers to a sample that serves as a reference, usually a known reference, for comparison to a test sample. A control can also represent an average value gathered from a population of similar individuals, e.g., cancer patients or healthy individuals with a similar medical background, same age, weight, etc. A control value can also be obtained from the same individual, e.g., from an earlier-obtained sample, prior to disease, or prior to treatment. As also discussed above, diagnosis refers to a relative probability that a disease (e.g. an autoimmune, inflammatory autoimmune, cancer, infectious, immune, or other disease) is present in the subject.

The terms comparing, correlating and associated, in reference to determination of a disease risk factor, refers to comparing the presence or amount of the risk factor (e.g., amount of intracellular target of a disease) in an individual to its presence or amount in persons known to suffer from, or known to be at risk of disease, or in persons known to be free of disease, and assigning an increased or decreased probability of having/developing the disease to an individual based on the assay result(s).

VI. Methods of Detecting

In embodiments is provided a compound, or pharmaceutically acceptable salt thereof, as described herein, including embodiments (e.g. in an aspect, embodiment, example, figure, table, or claim) connected (e.g., bonded, non-covalently associated, covalently bonded) to a detectable moiety. In embodiments, the compound connected to the detectable moiety may be used in a method of detecting a protein (e.g., photoaffinity labeling). In embodiments, the detectable moiety is a photochemically reactive species covalently attached to the compound. In embodiments, the photochemically reactive species is a compound including a nitrene, carbene, ketone, cation, and/or radical. In embodiments, the photochemically reactive species is a cyanine. Among the detectable moiety are imaging agents, including fluorescent and luminescent substances, including, but not limited to, a variety of organic or inorganic small molecules commonly referred to as "dyes," "labels," or "indicators." Examples include fluorescein, rhodamine, acridine dyes, Alexa dyes, and cyanine dyes. Enzymes that may be used as imaging agents in accordance with the embodiments of the disclosure include, but are not limited to, horseradish peroxidase, alkaline phosphatase, acid phosphatase, glucose oxidase, 0-galactosidase, 0-glucoronidase or β-lactamase. Such enzymes may be used in combination with a chromogen, a fluorogenic compound or a luminogenic compound to generate a detectable signal.

Provided herein is also a method of detecting an intracellular target in a cell, including contacting the cell with a cell penetrating conjugate as provided herein including embodiments thereof and detecting binding of the cell penetrating conjugate to the intracellular target. The cell can be a fixed cell or a live cell. In embodiments, the cell is located in vitro or in vivo. Binding can be detecting directly or indirectly. It is understood and contemplated herein that numerous methods may be used to detect the binding of the cell penetrating conjugate to its intracellular target. For example, binding can be detected directly by assaying coupling between the cell penetrating conjugate and its intracellular target. Binding can be determined, for example, by selecting an assay from the group consisting of a coimmunoprecipitation assay, a colocalization assay, or a fluorescence polarizing assay, as described below. The assays are known in the art, e.g., see Sambrook et al., Molecular Cloning: A Laboratory Manual, $3^{rd}$ Ed., Cold Spring Harbor Press, Cold Spring Harbor, NY (2001); Dickson, Methods Mol. Biol. 461:735-44 (2008); Nickels, Methods 47(1):53-62 (2009); and Zinchuk et al., Acta Histochem. Cytochem. 40(4):101-11 (2007).

In embodiments, binding is determining by an imaging method or system. Thus, the cell penetrating conjugates provided herein including embodiments thereof can also be used in imaging applications or other applications for analyzing intracellular target levels and/or activities. For example, the provided cell penetrating conjugates can be used for in vitro or in vivo imaging of intracellular targets of interest. In embodiments, the cell penetrating conjugates are used for live cell imaging. For example, live cell imaging can be used to monitor intracellular target distribution and/or dynamics inside living cells and is also applicable to monitoring target interactions. For example, the cell penetrating conjugates can be used in immunoprecipitation and coimmunoprecipitation assays to study protein-protein interactions in cells, in embodiments, in living cells. In embodiments, the cell penetrating conjugates are used for analysis of intracellular targets by flow cytometry. In imaging applications, the cell penetrating conjugates are, in embodiments, labeled as appropriate to the application being used. As described above, a label or a detectable moiety is a composition detectable by spectroscopic, photochemical, biochemical, immunochemical, chemical, or other physical means. Useful labels include, but are not limited to, 32P, fluorescent dyes (e.g. cyanine), electron-dense reagents, enzymes (e.g., as commonly used in an ELISA), biotin, digoxigenin, or haptens and proteins or other entities which can be made detectable, e.g., by incorporating a radiolabel into a peptide or antibody specifically reactive with a target peptide. Any method known in the art for conjugating an antibody to the label may be employed, e.g., using methods described in Hermanson, Bioconjugate Techniques 1996, Academic Press, Inc., San Diego.

VII. Methods of Treatment

The cell penetrating conjugates provided herein including embodiments thereof and compositions including the cell penetrating conjugates as described herein including embodiments thereof are useful for both prophylactic and therapeutic treatment. For prophylactic use, a therapeutically effective amount of the agents described herein are administered to a subject prior to or during early onset (e.g., upon initial signs and symptoms of an autoimmune disease). Therapeutic treatment involves administering to a subject a therapeutically effective amount of the agents described herein after diagnosis or development of disease. Thus, in another aspect, a method of treating a disease in a subject in need thereof is provided. The method includes administering to a subject an effective amount of the cell penetrating conjugate as provided herein including embodiments thereof, thereby treating the disease in the subject.

In embodiments, the method includes administering a second therapeutic agent to the subject. In embodiments, the disease is selected from the group consisting of autoimmune disease, developmental disorder, inflammatory disease, metabolic disorder, cardiovascular disease, liver disease, intestinal disease, infectious disease, endocrine disease, neurological disorder, and cancer. In embodiments, the disease is cancer. In embodiments, the cancer is B cell lymphoma. In embodiments, the non-cell penetrating protein of the conjugate binds an intracellular target and the intracellular target is STAT3, exportin 7, or Src. In embodiments, the non-cell penetrating protein of the conjugate binds an intracellular target and the intracellular target is phosphorylated Src. In embodiments, the non-cell penetrating protein of the conjugate is an antibody that specifically binds STAT3 and the second non-cell penetrating protein is an antibody that specifically binds exportin 7. In embodiments, the non-cell penetrating protein of the conjugate is an antibody and the intracellular target is STAT3.

In the provided methods of treatment, additional therapeutic agents can be used that are suitable to the disease being treated. Thus, in some embodiments, the provided methods of treatment further comprise administering a second therapeutic agent to the subject. Suitable additional therapeutic agents include, but are not limited to, therapeutic agent is selected from the group consisting of analgesics, anesthetics, analeptics, corticosteroids, anticholinergic agents, anticholinesterases, anticonvulsants, antineoplastic agents, allosteric inhibitors, anabolic steroids, antirheumatic agents, psychotherapeutic agents, neural blocking agents, anti-inflammatory agents, antihelmintics, antibiotics, anticoagulants, antifungals, antihistamines, antimuscarinic agents, antimycobacterial agents, antiprotozoal agents, antiviral agents, dopaminergics, hematological agents, immunological agents, muscarinics, protease inhibitors, vitamins, growth factors, and hormones. The choice of agent and dosage can be determined readily by one of skill in the art based on the given disease being treated.

Combinations of agents or compositions can be administered either concomitantly (e.g., as a mixture), separately but simultaneously (e.g., via separate intravenous lines) or sequentially (e.g., one agent is administered first followed by administration of the second agent). Thus, the term combination is used to refer to concomitant, simultaneous or sequential administration of two or more agents or compositions. The course of treatment is best determined on an individual basis depending on the particular characteristics of the subject and the type of treatment selected. The treatment, such as those disclosed herein, can be administered to the subject on a daily, twice daily, bi-weekly, monthly or any applicable basis that is therapeutically effective. The treatment can be administered alone or in combination with any other treatment disclosed herein or known in the art. The additional treatment can be administered simultaneously with the first treatment, at a different time, or on an entirely different therapeutic schedule (e.g., the first treatment can be daily, while the additional treatment is weekly).

According to the methods provided herein, the subject is administered an effective amount of one or more of the agents provided herein. The terms effective amount and effective dosage are used interchangeably. The term effective amount is defined as any amount necessary to produce a desired physiologic response (e.g., reduction of inflammation). Effective amounts and schedules for administering the agent may be determined empirically by one skilled in the art. The dosage ranges for administration are those large enough to produce the desired effect in which one or more symptoms of the disease or disorder are affected (e.g., reduced or delayed). The dosage should not be so large as to cause substantial adverse side effects, such as unwanted cross-reactions, anaphylactic reactions, and the like. Generally, the dosage will vary with the age, condition, sex, type of disease, the extent of the disease or disorder, route of administration, or whether other drugs are included in the regimen, and can be determined by one of skill in the art. The dosage can be adjusted by the individual physician in the event of any contraindications. Dosages can vary and can be administered in one or more dose administrations daily, for one or several days. Guidance can be found in the literature for appropriate dosages for given classes of pharmaceutical products. For example, for the given parameter, an effective amount will show an increase or decrease of at least 5%, 10%, 15%, 20%, 25%, 40%, 50%, 60%, 75%, 80%, 90%, or at least 100%. Efficacy can also be expressed as "-fold" increase or decrease. For example, a therapeutically effective amount can have at least a 1.2-fold, 1.5-fold, 2-fold, 5-fold, or more effect over a control. The exact dose and formulation will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Remington: The Science and Practice of Pharmacy, 20th Edition, Gennaro, Editor (2003), and Pickar, Dosage Calculations (1999)).

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

The terms "subject," "patient," "individual," etc. are not intended to be limiting and can be generally interchanged. That is, an individual described as a "patient" does not necessarily have a given disease, but may be merely seeking medical advice.

As used herein, "treating" or "treatment of" a condition, disease or disorder or symptoms associated with a condition, disease or disorder refers to an approach for obtaining beneficial or desired results, including clinical results. Beneficial or desired clinical results can include, but are not limited to, alleviation or amelioration of one or more symptoms or conditions, diminishment of extent of condition, disorder or disease, stabilization of the state of condition, disorder or disease, prevention of development of condition, disorder or disease, prevention of spread of condition, disorder or disease, delay or slowing of condition, disorder or disease progression, delay or slowing of condition, disorder or disease onset, amelioration or palliation of the condition, disorder or disease state, and remission, whether partial or total. "Treating" can also mean prolonging survival of a subject beyond that expected in the absence of treatment. "Treating" can also mean inhibiting the progression of the condition, disorder or disease, slowing the progression of the condition, disorder or disease temporarily, although in some instances, it involves halting the progression of the condition, disorder or disease permanently. As used herein the terms treatment, treat, or treating refers to a method of reducing the effects of one or more symptoms of a disease or condition characterized by expression of the protease or symptom of the disease or condition characterized by expression of the protease. Thus in the disclosed method, treatment can refer to a 10%, 20%, 30%, 40%, 50%, 60%, 70%, 80%, 90%, or 100% reduction in the severity of an established disease, condition, or symptom of the disease or condition. For example, a method for treating a disease is considered to be a treatment if there is a 10% reduction in one or more symptoms of the disease in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition. Further, as used herein, references to decreasing, reducing, or inhibiting include a change of 10%, 20%, 30%, 40%, 50%, 60%, 70%, 80%, 90% or greater as compared to a control level and such terms can include but do not necessarily include complete elimination.

As used herein, the term "pharmaceutically acceptable" is used synonymously with "physiologically acceptable" and "pharmacologically acceptable". A pharmaceutical composition will generally comprise agents for buffering and preservation in storage, and can include buffers and carriers for appropriate delivery, depending on the route of administration.

An "effective amount" is an amount sufficient to accomplish a stated purpose (e.g. achieve the effect for which it is administered, treat a disease, reduce enzyme activity, reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom (s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme or protein relative to the absence of the antagonist. A "function disrupting amount," as used herein, refers to the amount of antagonist required to disrupt the function of an enzyme or protein relative to the absence of the antagonist. Guidance can be found in the literature for appropriate dosages for given classes of pharmaceutical products. For example, for the given parameter, an effective amount will show an increase or decrease of at least 5%, 10%, 15%, 20%, 25%, 40%, 50%, 60%, 75%, 80%, 90%, or at least 100%. Efficacy can also be expressed as "-fold" increase or decrease. For example, a therapeutically effective amount can have at least a 1.2-fold, 1.5-fold, 2-fold, 5-fold, or more effect over a control. The exact amounts will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins).

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies, for example cancer therapies such as chemotherapy, hormonal therapy, radiotherapy, or immunotherapy. The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols.

The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, J. Biomater Sci. Polym. Ed. 7:623-645, 1995; as biodegradable and injectable gel formulations (see, e.g., Gao Pharm. Res. 12:857-863, 1995); or, as microspheres for oral administration (see, e.g., Eyles, J. Pharm. Pharmacol. 49:669-674, 1997). In embodiments, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, J. Microencapsul. 13:293-306, 1996; Chonn, Curr. Opin. Biotechnol. 6:698-708, 1995; Ostro, Am. J. Hosp. Pharm. 46:1576-1587, 1989). The compositions of the present invention can also be delivered as nanoparticles.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

"Anti-cancer agent" is used in accordance with its plain ordinary meaning and refers to a composition (e.g. compound, drug, antagonist, inhibitor, modulator) having anti-neoplastic properties or the ability to inhibit the growth or proliferation of cells. In embodiments, an anti-cancer agent is a chemotherapeutic. In embodiments, an anti-cancer agent is an agent identified herein having utility in methods of treating cancer. In embodiments, an anti-cancer agent is an agent approved by the FDA or similar regulatory agency of a country other than the USA, for treating cancer.

EMBODIMENTS

Embodiment P1. A cell-penetrating conjugate having the formula:

(I)

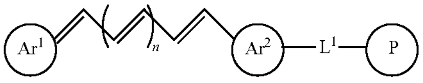

or (IV)

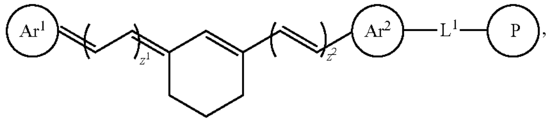

, wherein

- $Ar^1$ is substituted or unsubstituted cycloalkyl, substituted or unsubstituted heterocycloalkyl, substituted or unsubstituted fused ring aryl or substituted or unsubstituted fused ring heteroaryl;
- $Ar^2$ is substituted or unsubstituted cycloalkylene, substituted or unsubstituted heterocycloalkylene, substituted or unsubstituted arylene or substituted or unsubstituted heteroarylene;
- $L^1$ is substituted or unsubstituted alkylene or substituted or unsubstituted heteroalkylene;
- P is a non-cell penetrating protein;
- n is 1 or 2; and
- $z^1$ and $z^2$ are independently 1 or 2.

Embodiment P2. The cell-penetrating conjugate of embodiment P1, wherein $Ar^1$ is substituted or unsubstituted fused ring aryl or substituted or unsubstituted fused ring heteroaryl; and $Ar^2$ is substituted or unsubstituted fused ring arylene or substituted or unsubstituted fused ring heteroarylene.

Embodiment P3. The cell-penetrating conjugate of embodiment P1 or P2, wherein the cell-penetrating conjugate has the formula:

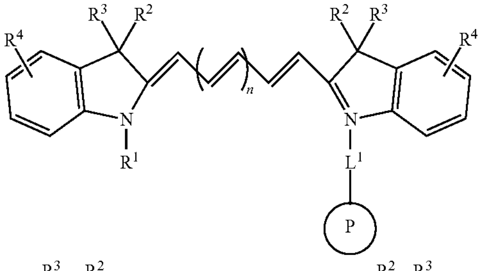

or

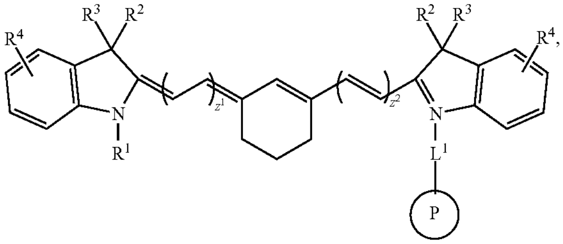

, wherein $R^1$, $R^2$, $R^3$ and $R^4$ are independently hydrogen, halogen, $CX_3$, —CN, —C(O)OH, —$CH_2$C(O)OH, —C(O)$NH_2$, —OH, —SH, —$NO_2$, —$NH_2$, —$NHNH_2$, —$ONH_2$, —NHC═(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl; and X is —F, —Cl, —Br, or —I.

Embodiment P4. The cell-penetrating conjugate of embodiment P3, wherein $R^1$, $R^2$, $R^3$ and $R^4$ are independently hydrogen or substituted or unsubstituted alkyl.

Embodiment P5. The cell-penetrating conjugate of embodiment P3 or P4, wherein $R^1$, $R^2$, $R^3$ and $R^4$ are independently hydrogen or methyl.

Embodiment P6. The cell-penetrating conjugate of one of embodiments P3-P5, wherein $R^1$, $R^2$ and $R^3$ are methyl.

Embodiment P7. The cell-penetrating conjugate of one of embodiments P3-P6, wherein $R^4$ is hydrogen.

Embodiment P8. The cell-penetrating conjugate of one of embodiments P1-P7, wherein $L^1$ is unsubstituted alkylene or unsubstituted heteroalkylene.

Embodiment P9. The cell-penetrating conjugate of one of embodiments P1-P8, wherein $L^1$ is unsubstituted heteroalkylene.

Embodiment P10. The cell-penetrating conjugate of one of embodiments P1-P7, wherein $L^1$ has the formula:

$$—L^{1A}—L^{2A}—, \quad \text{(III)}$$

wherein $L^{1A}$ is substituted or unsubstituted alkylene; and $L^{2A}$ is —C(O)—, —C(O)O—, —OC(O)—, —C(O)NH—, —NH—, —NHC(O)—, —O—, —S—, —S(O)—, —$S(O)_2$NH—, —$NHS(O)_2$—, substituted or unsubstituted alkylene or substituted or unsubstituted heteroalkylene.

Embodiment P11. The cell-penetrating conjugate of one of embodiments P1-P10, wherein $L^1$ is

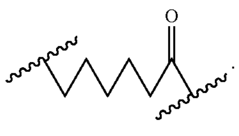 [SMILES: *CCCCCC(*)=O]

Embodiment P12. The cell penetrating conjugate of one of embodiments P1 to P11, wherein $L^1$ is covalently attached to a lysine of said non-cell penetrating protein.

Embodiment P13. The cell-penetrating conjugate of one of embodiments P1-P12, wherein n is 1.

Embodiment P14. The cell-penetrating conjugate of one of embodiments P1-P12, wherein $z^1$ and $z^2$ are 1.

Embodiment P15. The cell-penetrating conjugate of one of embodiments P1-P14, wherein said non-cell penetrating protein has a molecular weight of greater than 25 kD.

Embodiment P16. The cell-penetrating conjugate of one of embodiments P1-P15, wherein said non-cell penetrating protein has a molecular weight of 25 to 750 kD.

Embodiment P17. The cell-penetrating conjugate of one of embodiments P1-P15, wherein said non-cell penetrating protein is an antibody.

Embodiment P18. The cell-penetrating conjugate of embodiment P17, wherein said antibody is an IgG antibody.

Embodiment P19. The cell-penetrating conjugate of embodiment P17, wherein said antibody is an IgA, IgM, IgD or IgE antibody.

Embodiment P20. The cell-penetrating conjugate of embodiment P17, wherein said antibody is an Fv fragment.

Embodiment P21. The cell penetrating conjugate of one of embodiments P17 to P19, wherein said antibody is a humanized antibody.

Embodiment P22. The cell penetrating conjugate of one of embodiments P1-P21, wherein said non-cell penetrating protein binds an intracellular target.

Embodiment P23. The cell penetrating conjugate of embodiment P22, wherein said intracellular target is a target of a disease selected from the group consisting of autoimmune disease, inflammatory disease, metabolic disorder, developmental disorder, cardiovascular disease, liver disease, intestinal disease, infectious disease, endocrine disease, neurological disorder, and cancer.

Embodiment P24. The cell penetrating conjugate of embodiment P22 or P23, wherein said intracellular target is a signaling molecule or transcription factor.

Embodiment P25. The cell penetrating conjugate of embodiment P24, wherein said signaling molecule is a phosphatase or kinase.

Embodiment P26. The cell penetrating conjugate of embodiment P22, wherein said intracellular target is a cancer target.

Embodiment P27. The cell penetrating conjugate of embodiment P26, wherein said intracellular target is selected from the group consisting of STAT3, exportin 7 and Src.

Embodiment P28. The cell penetrating conjugate of embodiment P27, wherein said intracellular target is STAT3.

Embodiment P29. The cell penetrating conjugate of one of embodiments P1-P28, wherein said non-cell penetrating protein further comprises a detectable moiety.

Embodiment P30. The cell penetrating conjugate of one of embodiments P1-P29, wherein said conjugate is bound to an intracellular target.

Embodiment P31. A cell comprising the cell penetrating conjugate of one of embodiments P1-P30.

Embodiment P32. A pharmaceutical composition comprising said cell penetrating conjugate of one of embodiments P1-P30 and a pharmaceutically acceptable carrier.

Embodiment P33. A method of delivering a non-cell penetrating protein into a cell comprising contacting a cell with the cell penetrating conjugate of one of embodiments P1-P30.

Embodiment P34. The method of embodiment P33, wherein the non-cell penetrating protein binds a nuclear protein in the cytoplasm thereby forming a non-cell penetrating protein-nuclear protein complex.

Embodiment P35. The method of embodiment P34, wherein the non-cell penetrating protein-nuclear protein complex is not capable of entering the nucleus of the cell.

Embodiment P36. A method of treating a disease in a subject in need thereof, the method comprising administering to a subject an effective amount of said cell penetrating conjugate of one embodiments P1-P30, thereby treating said disease in said subject.

Embodiment P37. The method of embodiment P36, further comprising administering a second therapeutic agent to said subject.

Embodiment P38. The method of embodiment P36 or P37, wherein said disease is selected from the group consisting of autoimmune disease, developmental disorder, inflammatory disease, metabolic disorder, cardiovascular disease, liver disease, intestinal disease, infectious disease, endocrine disease, neurological disorder, and cancer.

Embodiment P39. The method of embodiment P38, wherein said disease is cancer.

Embodiment P40. The method of embodiment P39, wherein said non-cell penetrating protein of said conjugate binds an intracellular target and said intracellular target is STAT3, exportin 7 or Src.

Embodiment P41. The method of embodiment P39, wherein said non-cell penetrating protein of said conjugate binds an intracellular target and said intracellular target is phosphorylated Src.

Embodiment P42. The method of embodiment P39, wherein said non-cell penetrating protein of said conjugate is an antibody and wherein said intracellular target is STAT3.

ADDITIONAL EMBODIMENTS

Embodiment 1. A cell-penetrating conjugate having the formula:

(I)

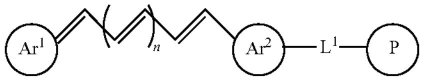

or (IV)

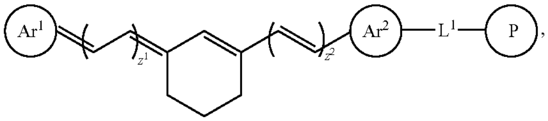

, wherein $Ar^1$ is substituted or unsubstituted cycloalkyl, substituted or unsubstituted heterocycloalkyl, substituted or unsubstituted fused ring aryl or substituted or unsubstituted fused ring heteroaryl;

$Ar^2$ is substituted or unsubstituted cycloalkylene, substituted or unsubstituted heterocycloalkylene, substituted or unsubstituted arylene or substituted or unsubstituted heteroarylene;

$L^1$ is substituted or unsubstituted alkylene or substituted or unsubstituted heteroalkylene;

P is a non-cell penetrating protein;

n is 1 or 2; and $z^1$ and $z^2$ are independently 1 or 2.

Embodiment 2. The cell-penetrating conjugate of embodiment 1, wherein $Ar^1$ is substituted or unsubstituted fused ring aryl or substituted or unsubstituted fused ring heteroaryl; and $Ar^2$ is substituted or unsubstituted fused ring arylene or substituted or unsubstituted fused ring heteroarylene.

Embodiment 3. The cell-penetrating conjugate of embodiment 1 or 2, wherein the cell-penetrating conjugate has the formula:

(II)

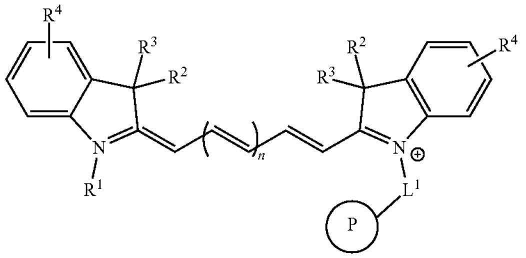

or (V)

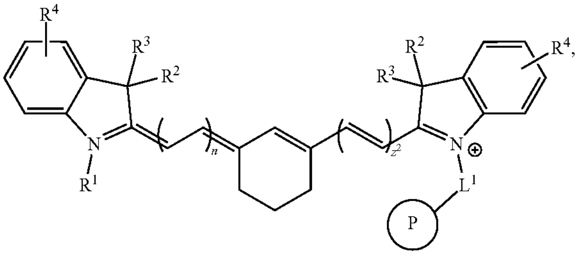

wherein $R^1$, $R^2$, $R^3$ and $R^4$ are independently hydrogen, halogen, $—CX_3$, —CN, —C(O)OH, $—CH_2C(O)OH$, $—C(O)NH_2$, —OH, —SH, $—NO_2$, $—NH_2$, $—NHNH_2$, $—ONH_2$, $—NHC{=}(O)NHNH_2$, $—SO_3H$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl; and X is —F, —Cl, —Br, or —I.

Embodiment 4. The cell-penetrating conjugate of embodiment 3, wherein $R^1$, $R^2$, $R^3$ and $R^4$ are independently hydrogen or substituted or unsubstituted alkyl.

Embodiment 5. The cell-penetrating conjugate of embodiment 3 or 4, wherein $R^1$, $R^2$, $R^3$ and $R^4$ are independently hydrogen or methyl.

Embodiment 6. The cell-penetrating conjugate of one of embodiments 3-5, wherein $R^1$, $R^2$ and $R^3$ are independently unsubstituted methyl.

Embodiment 7. The cell-penetrating conjugate of one of embodiments 3-6, wherein $R^4$ is hydrogen.

Embodiment 8. The cell-penetrating conjugate of one of embodiments 1-7, wherein $L^1$ is unsubstituted alkylene or unsubstituted heteroalkylene.

Embodiment 9. The cell-penetrating conjugate of one of embodiments 1-8, wherein $L^1$ is unsubstituted heteroalkylene.

Embodiment 10. The cell-penetrating conjugate of one of embodiments 1-7, wherein $L^1$ has the formula:

$$-L^{1A}-L^{2A}- \quad \text{(III)},$$

wherein $L^{1A}$ is a bond, substituted or unsubstituted alkylene; and $L^{2A}$ is a bond, —C(O)—, —C(O)O—, —OC(O)—, —C(O)NH—, —NH—, —NHC(O)—, —O—, —S—, —S(O)—, $—S(O)_2NH—$, $—NHS(O)_2—$, substituted or unsubstituted alkylene or substituted or unsubstituted heteroalkylene.

Embodiment 11. The cell-penetrating conjugate of one of embodiments 1-10, wherein $L^1$ is

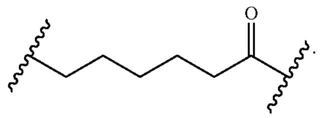 [SMILES: *CCCCCC(*)=O]

Embodiment 12. The cell penetrating conjugate of one of embodiments 1 to 11, wherein $L^1$ is covalently attached to a lysine of said non-cell penetrating protein.

Embodiment 13. The cell-penetrating conjugate of one of embodiments 1-12, wherein n is 1.

Embodiment 14. The cell-penetrating conjugate of one of embodiments 1-12, wherein $z^1$ and $z^2$ are 1.

Embodiment 15. The cell-penetrating conjugate of one of embodiments 1-14, wherein said non-cell penetrating protein has a molecular weight of greater than 25 kD.

Embodiment 16. The cell-penetrating conjugate of one of embodiments 1-15, wherein said non-cell penetrating protein has a molecular weight of 25 to 750 kD.

Embodiment 17. The cell-penetrating conjugate of one of embodiments 1-16, wherein said non-cell penetrating protein is an antibody.

Embodiment 18. The cell-penetrating conjugate of embodiment 17, wherein said antibody is an IgG antibody.

Embodiment 19. The cell-penetrating conjugate of embodiment 17, wherein said antibody is an IgA, IgM, IgD or IgE antibody.

Embodiment 20. The cell-penetrating conjugate of embodiment 17, wherein said antibody is an Fv fragment.

Embodiment 21. The cell penetrating conjugate of one of embodiments 17 to 19, wherein said antibody is a humanized antibody.

Embodiment 22. The cell penetrating conjugate of one of embodiments 1-21, wherein said non-cell penetrating protein binds an intracellular target.

Embodiment 23. The cell penetrating conjugate of embodiment 22, wherein said intracellular target is a target of a disease selected from the group consisting of autoimmune disease, inflammatory disease, metabolic disorder, developmental disorder, cardiovascular disease, liver disease, intestinal disease, infectious disease, endocrine disease, neurological disorder, and cancer.

Embodiment 24. The cell penetrating conjugate of embodiment 22 or 23, wherein said intracellular target is a signaling molecule or transcription factor.

Embodiment 25. The cell penetrating conjugate of embodiment 24, wherein said signaling molecule is a phosphatase or kinase.

Embodiment 26. The cell penetrating conjugate of embodiment 22, wherein said intracellular target is a cancer target.

Embodiment 27. The cell penetrating conjugate of embodiment 26, wherein said intracellular target is selected from the group consisting of STAT3, exportin 7 and Src.

Embodiment 28. The cell penetrating conjugate of embodiment 27, wherein said intracellular target is STAT3.

Embodiment 29. The cell penetrating conjugate of one of embodiments 1-28, wherein said non-cell penetrating protein further comprises a detectable moiety.

Embodiment 30. The cell penetrating conjugate of one of embodiments 1-29, wherein said conjugate is bound to an intracellular target.

Embodiment 31. A cell comprising the cell penetrating conjugate of one of embodiments 1-30.

Embodiment 32. A pharmaceutical composition comprising said cell penetrating conjugate of one of embodiments 1-30 and a pharmaceutically acceptable carrier.

Embodiment 33. A method of delivering a non-cell penetrating protein into a cell comprising contacting a cell with the cell penetrating conjugate of one of embodiments 1-30.

Embodiment 34. The method of embodiment 33, wherein the non-cell penetrating protein binds a nuclear protein in the cytoplasm thereby forming a non-cell penetrating protein-nuclear protein complex.

Embodiment 35. The method of embodiment 34, wherein the non-cell penetrating protein-nuclear protein complex is not capable of entering the nucleus of the cell.

Embodiment 36. A method of treating a disease in a subject in need thereof, the method comprising administering to a subject an effective amount of said cell penetrating conjugate of one embodiments 1-30, thereby treating said disease in said subject.

Embodiment 37. The method of embodiment 36, further comprising administering a second therapeutic agent to said subject.

Embodiment 38. The method of embodiment 36 or 37, wherein said disease is selected from the group consisting of autoimmune disease, developmental disorder, inflammatory disease, metabolic disorder, cardiovascular disease, liver disease, intestinal disease, infectious disease, endocrine disease, neurological disorder, and cancer.

Embodiment 39. The method of embodiment 38, wherein said disease is cancer.

Embodiment 40. The method of embodiment 39, wherein said cancer is B cell lymphoma.

Embodiment 41. The method of embodiment 39, wherein said non-cell penetrating protein of said conjugate binds an intracellular target and said intracellular target is STAT3, exportin 7 or Src.

Embodiment 42. The method of embodiment 39, wherein said non-cell penetrating protein of said conjugate binds an intracellular target and said intracellular target is phosphorylated Src.

Embodiment 43. The method of embodiment 39, wherein said non-cell penetrating protein of said conjugate is an antibody and wherein said intracellular target is STAT3.

VIII. Examples

The following examples are offered to illustrate, but not to limit the claimed invention.

A. Modifications of Anti-Stat3 Antibodies and Uses Thereof

In embodiments, the anti-Stat3 antibody is covalently bound to cyanine 3, wherein the unbound cyanine 3 has the formula:

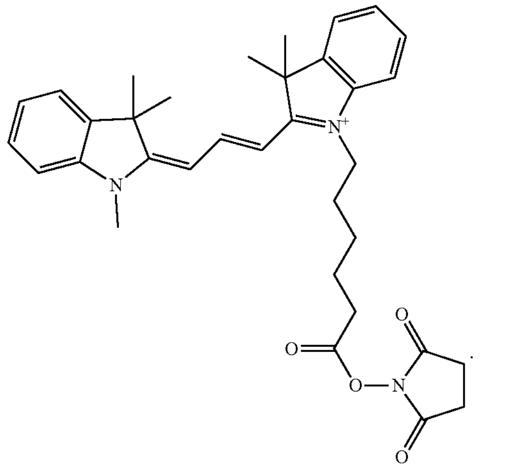 [SMILES: CN1/C(=C/C=C/C2=[N+](CCCCCC(=O)ON3C(=O)CCC3=O)c3ccccc3C2(C)C)C(C)(C)c2ccccc21]

In embodiments, the anti-Stat3 antibody is covalently bound to cyanine 5, wherein the unbound cyanine 5 has the formula:

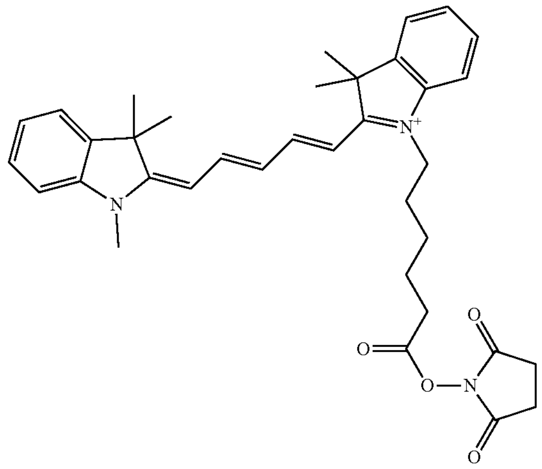

or

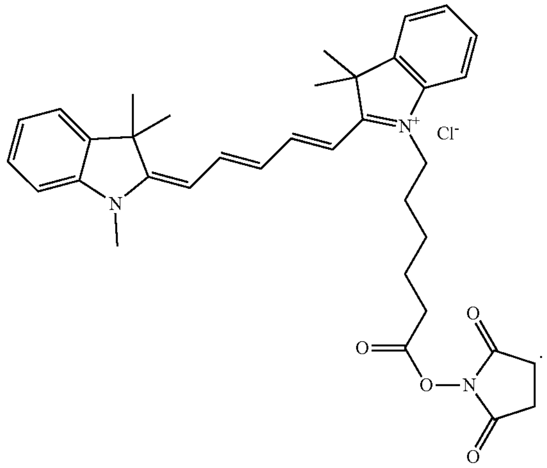

Once anti-Stat3 antibodies were covalently bound to cyanine 3 (red emission in the infrared spectrum) or cyanine 5 (“blue” emission in the infrared spectrum), cyanine modified antibodies were subjected to SDS-PAGE under non-reducing conditions to assess successful covalent conjugation of antibodies to cyanines. It is of advantage that cyanines 3 and 5 have fluorescent activity in a light spectrum visible for the human eye so that one can see fluorescent IgG proteins by visual inspection without further experimental analysis (FIG. 1).

Figure 2A:
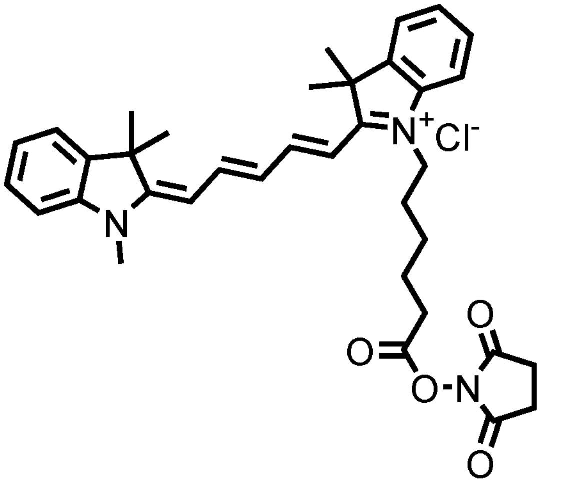
FIGS. 2A-2B.
Figure 2A:
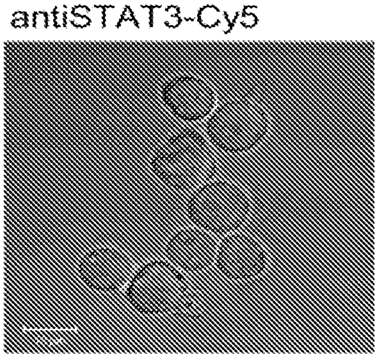
Figure 2A:
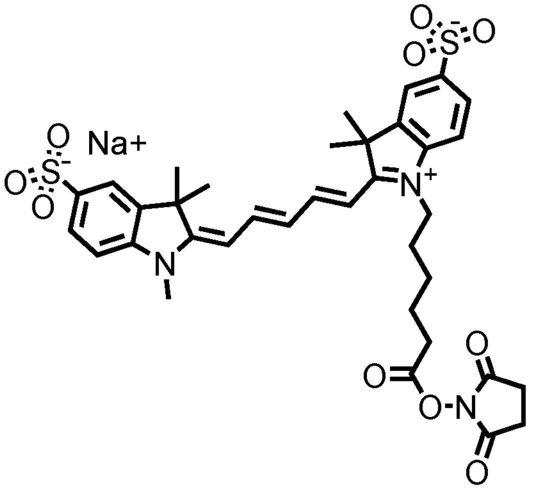
Figure 2A:
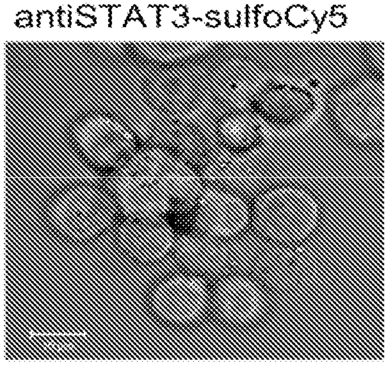
Figure 2A:
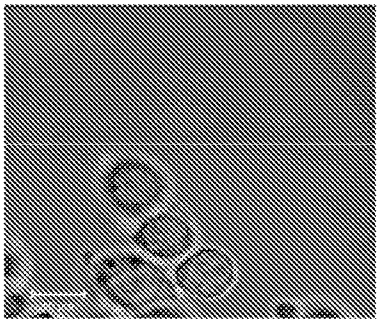
Figure 2B:
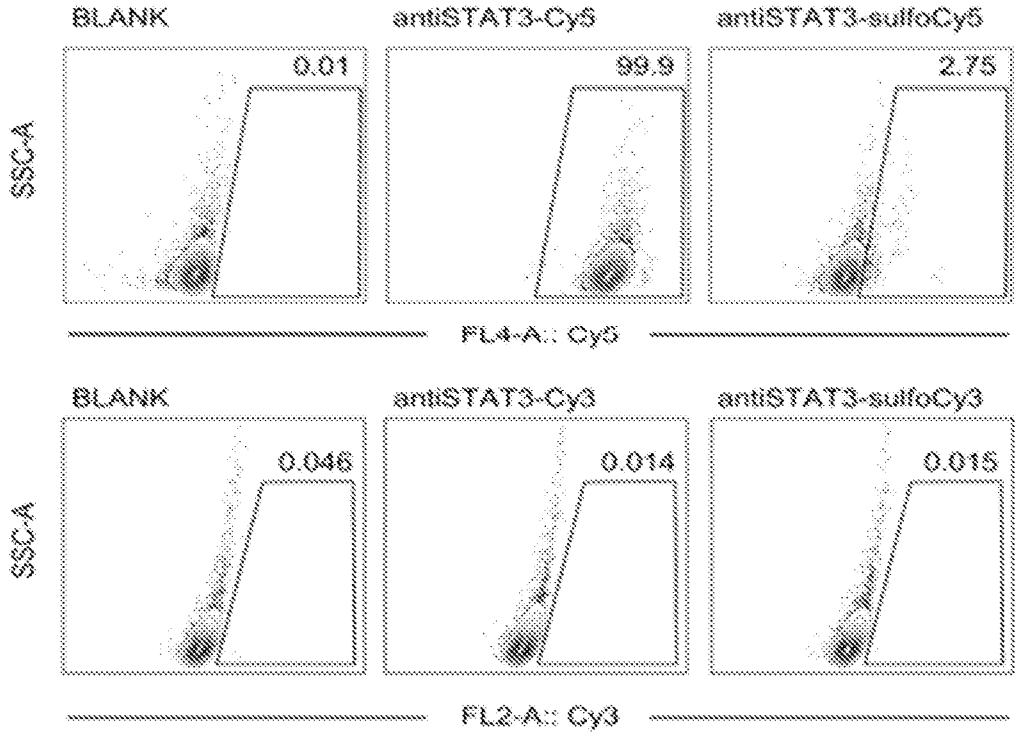

Purified anti-Stat3-Cy3 and anti-Stat3-Cy5 were subjected to cell-based assays to assess intracellular localization and cell penetration efficacy (FIGS. 2A-2B). As a negative control for anti-Stat3-Cy3, anti-Stat3 antibodies were covalently bound to sulfoCy3 to form anti-Stat3-sulfoCy3. To serve as a negative control for anti-Stat3-Cy5, anti-Stat3 antibodies were covalently bound to sulfoCy5, wherein the unbound sulfoCy5 has the formula:

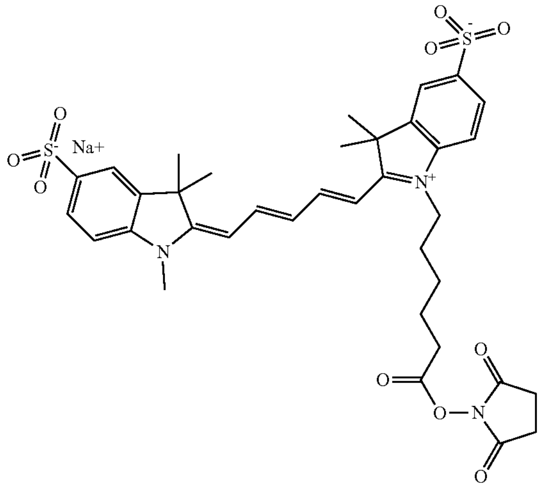

or

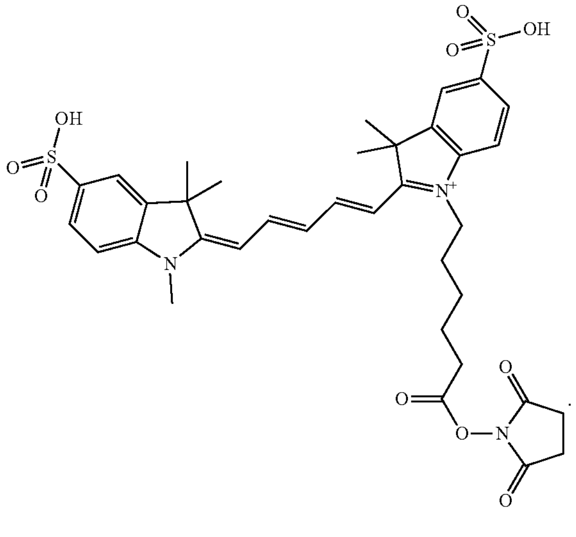

Figure 3:
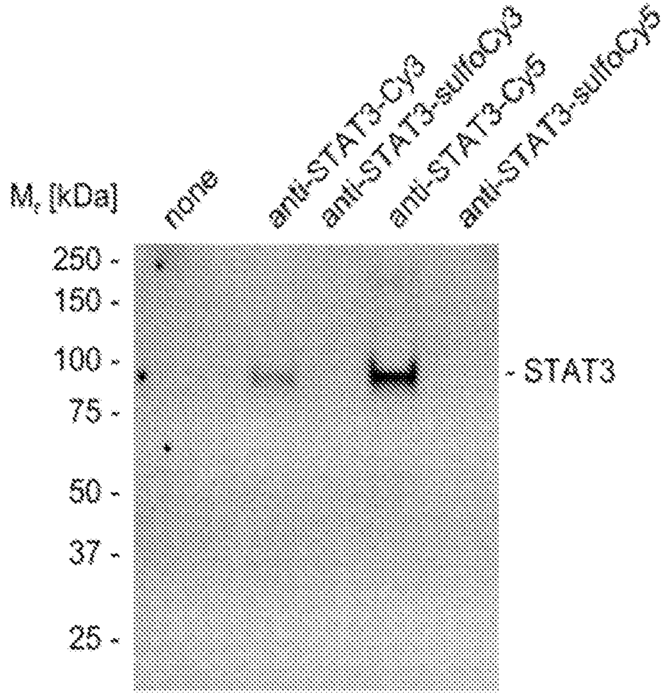
FIG. 3. Target recognition by anti-Stat3-Cy5 conjugate. Human B cell lymphoma Ly3 cells were incubated for 1 h at 10 μg/ml with cyanine- or sulfo-cyanine-Stat3-antibodies as indicated. Whole cell lysates were prepared and alternative immunoprecipitation was performed where protein-coupled agarose beads were added to lysates once cleared from cell debris. Target recognition was achieved exclusively by the anti-STAT3-Cy5 conjugate as shown by Western blot detection of Stat3 migration at predicted 89 kDa.

Purified anti-Stat3-Cy3 and anti-Stat3-Cy5 as well as their controls, anti-Stat3-sulfoCy3 and anti-Stat3-sulfoCy5, were incubated with human B cell lymphoma Ly3 cells to test recognition of their intracellular target Stat3. Once whole cell lysates were isolated and cleared from cell debris, alternative immunoprecipitation was performed to determine target recognition by cyanine-Stat3-antibodies (FIG. 3).

In embodiments, the anti-Stat3 antibody is covalently bound to Cy7, wherein the unbound Cy7 has the formula:

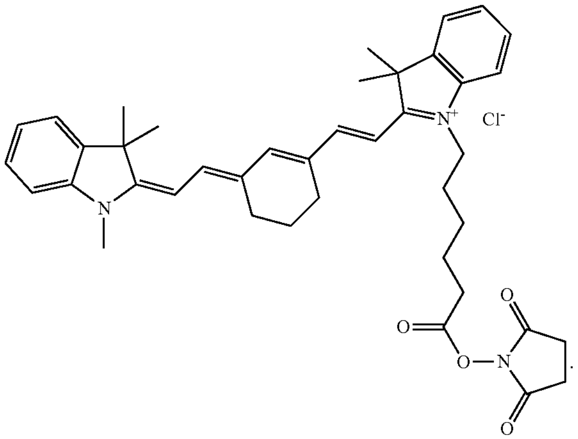 [SMILES: CN1/C(=C/C=C2C=C(/C=C/C3=[N+](CCCCCC(=O)ON4C(=O)CCC4=O)c4ccccc4C3(C)C)CCC/2)C(C)(C)c2ccccc21 ; [Cl-]]

In embodiments, the anti-Stat3 antibody is covalently bound to sulfoCy7, wherein the unbound sulfoCy7 has the formula:

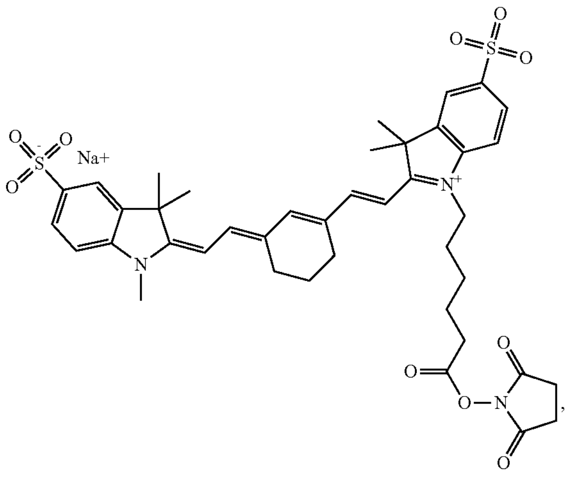

or

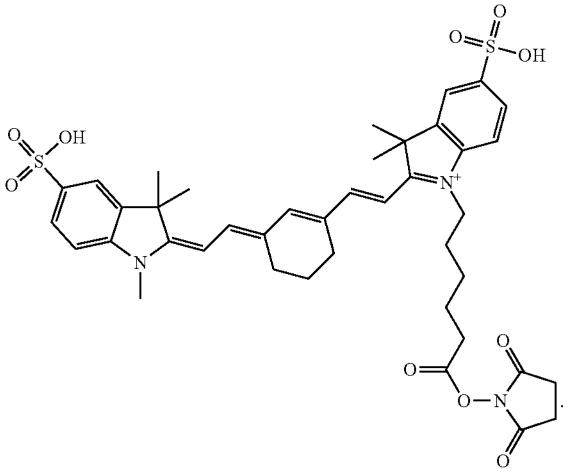 [SMILES: CN1/C(=C/C=C2C=C(/C=C/C3=[N+](CCCCCC(=O)ON4C(=O)CCC4=O)c4ccc(S(=O)(=O)O)cc4C3(C)C)CCC/2)C(C)(C)c2cc(S(=O)(=O)O)ccc21]

Figure 4A:
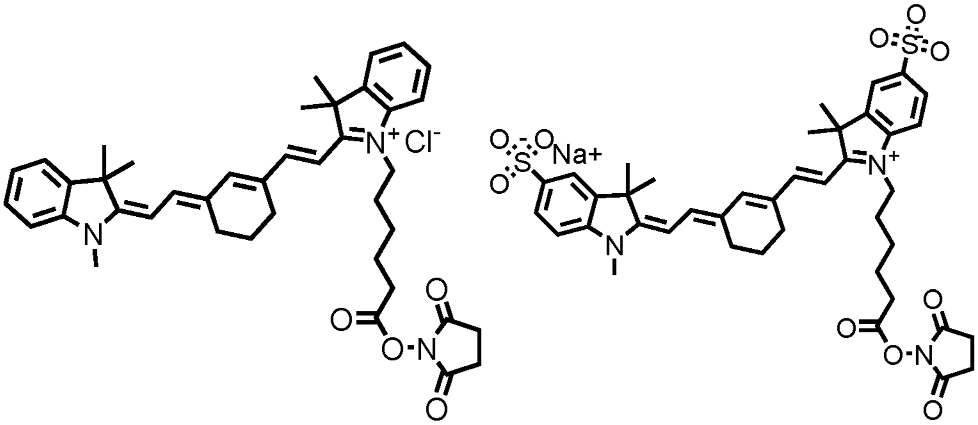
FIGS. 4A-4B. Target recognition by anti-Stat3-Cy7 conjugate.
Figure 4B:
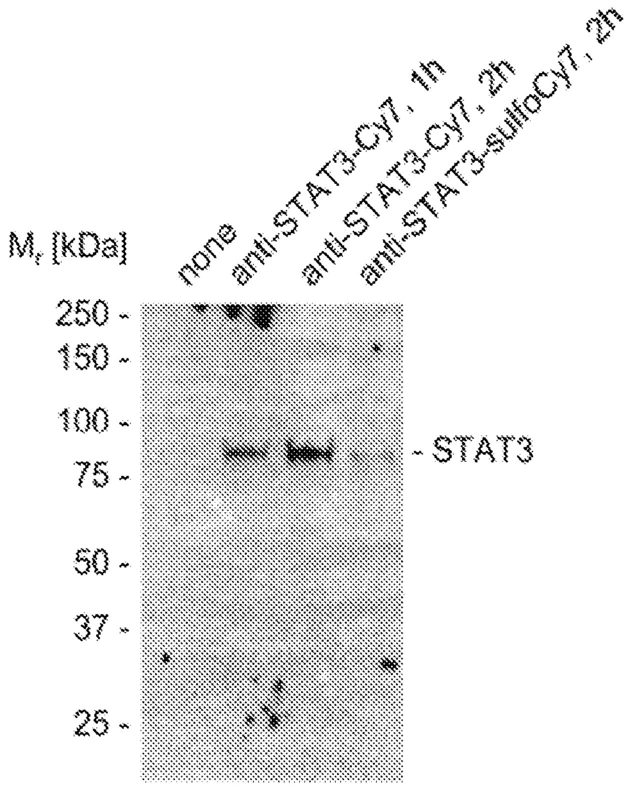

Anti-Stat3-Cy7 antibodies were used to test for recognition of strictly intracellular antigen STAT3 in human U251 glioma cells. Anti-Stat3-sulfoCy7 antibodies served as a negative control. Cells were incubated for 2 hrs at 10 mg/ml. Once whole cell lysates were isolated and cleared from cell debris, alternative immunoprecipitation was performed to determine target recognition by cyanine-Stat3-antibodies (FIG. 4).

What is claimed is:

1. A method of delivering a cell penetrating conjugate into a cell comprising administering to a cell a cell-penetrating conjugate of formula:

(II)

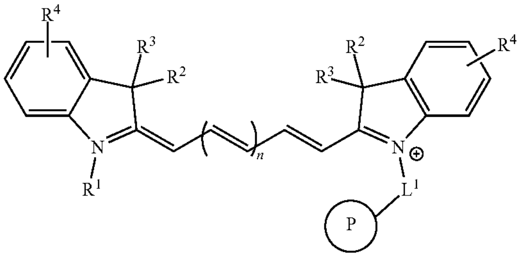

or (V)

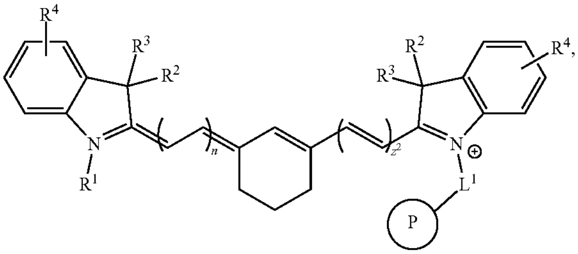

wherein $R^1$, $R^2$, $R^3$ and $R^4$ are independently hydrogen, halogen, $—CX_3$, —CN, —C(O)OH, $—CH_2C(O)OH$, $—C(O)NH_2$, —OH, —SH, $—NO_2$, $—NH_2$, $—NHNH_2$, $—ONH_2$, $—NHC{=}(O)NHNH_2$, $—SO_3H$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

X is —F, —Cl, —Br, or —I;

$L^1$ is substituted or unsubstituted alkylene or substituted or unsubstituted heteroalkylene;

P is a STAT3 antibody, wherein said STAT3 antibody is non-cell penetrating if not attached to the remainder of the compound of formula (II) or (V);

n is 1 or 2;

$z^1$ and $z^2$ are independently 1 or 2;

wherein said cell is an intact cell;

wherein said antibody binds an intracellular target in said intact cell;

wherein said intracellular target is a therapeutic target of cancer located intracellularly; and wherein said intracellular target is not HER2, thereby delivering said cell penetrating conjugate into said cell.

2. The method of claim 1, wherein $R^1$, $R^2$, $R^3$ and $R^4$ are independently hydrogen or substituted or unsubstituted alkyl.

3. The method of claim 2, wherein $R^1$, $R^2$ and $R^3$ are independently unsubstituted methyl.

4. The method of claim 3, wherein $R^4$ is hydrogen.

5. The method of claim 1, wherein $L^1$ is unsubstituted heteroalkylene.

6. The method of claim 5, wherein $L^1$ is

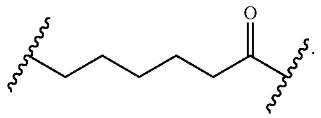 [SMILES: *CCCCCC(*)=O]

7. The method of claim 6, wherein $L^1$ is covalently attached to a lysine of said antibody.

8. The method of claim 7, wherein n is 1.

* * * * *